US008182581B2

(12) United States Patent
Armstrong et al.

(10) Patent No.: US 8,182,581 B2
(45) Date of Patent: May 22, 2012

(54) HIGH STABILITY DIIONIC LIQUID SALTS

(75) Inventors: Daniel W. Armstrong, Ames, IA (US);
Jared Anderson, Ames, IA (US)

(73) Assignee: Sigma-Aldrich Co. LLC, St. Louis, MO (US)

( * ) Notice: Subject to any disclaimer, the term of this patent is extended or adjusted under 35 U.S.C. 154(b) by 1089 days.

(21) Appl. No.: 11/187,389

(22) Filed: Jul. 22, 2005

(65) Prior Publication Data

US 2006/0025598 A1 Feb. 2, 2006

Related U.S. Application Data

(60) Provisional application No. 60/590,857, filed on Jul. 23, 2004.

(51) Int. Cl.
*B01D 53/02* (2006.01)
*C07D 233/00* (2006.01)
*C07D 207/18* (2006.01)
(52) U.S. Cl. .......................... 95/83; 548/335.1; 548/565
(58) Field of Classification Search .................. None
See application file for complete search history.

(56) References Cited

U.S. PATENT DOCUMENTS

| | | | | |
|---|---|---|---|---|
| 2,865,964 A | 12/1958 | Dornfeld et al. | ........... | 260/606.5 |
| 4,557,919 A | 12/1985 | Sumitani et al. | ............... | 423/329 |
| 4,948,395 A | 8/1990 | Armstrong | .......................... | 95/88 |
| 5,064,944 A | 11/1991 | Armstrong | ................. | 536/123.1 |
| 5,827,602 A | 10/1998 | Koch et al. | ..................... | 429/194 |
| 6,437,149 B1 | 8/2002 | Genet et al. | | |
| 6,531,241 B1 * | 3/2003 | McEwen | ......................... | 429/46 |
| 6,900,313 B2 * | 5/2005 | Wasserscheid et al. | ......... | 544/59 |
| 8,097,721 B2 | 1/2012 | Armstrong et al. | | |
| 2001/0031875 A1 | 10/2001 | Kitazume | ..................... | 546/347 |
| 2004/0254147 A1 | 12/2004 | Lo et al. | | |
| 2006/0014955 A1 | 1/2006 | Armstrong et al. | ................ | 546/2 |
| 2006/0025598 A1 | 2/2006 | Armstrong et al. | ............ | 548/101 |
| 2008/0027231 A1 | 1/2008 | Armstrong et al. | ........ | 548/313.7 |
| 2008/0210858 A1 | 9/2008 | Armstrong et al. | ............ | 250/282 |
| 2009/0145197 A1 | 6/2009 | Armstrong et al. | ........... | 72/23.41 |
| 2009/0266230 A1 * | 10/2009 | Radosz et al. | ..................... | 95/51 |

FOREIGN PATENT DOCUMENTS

| | | |
|---|---|---|
| CN | 1383920 | 5/2004 |
| CN | 1383921 | 6/2004 |
| DE | 39618 | 6/1965 |
| DE | 2031213 | 12/1971 |
| DE | 3333124 | 5/1985 |
| EP | 0 137 241 | 4/1985 |
| FR | 2372826 | 6/1978 |
| GB | 633158 | 12/1949 |
| GB | 711654 | 7/1954 |

(Continued)

OTHER PUBLICATIONS

Liu et al., Talanta (2005), 65(3), 705-.*

(Continued)

*Primary Examiner* — Karl J Puttlitz
(74) *Attorney, Agent, or Firm* — Harness, Dickey & Pierce, P.L.C.; J. Timothy Keane; Kisuk Lee

(57) ABSTRACT

The present invention relates to diionic liquid salts of dicationic or dianionic molecules, as well as solvents comprising diionic liquids and the use of diionic liquids as the stationary phase in a gas chromatographic column.

26 Claims, 9 Drawing Sheets

FOREIGN PATENT DOCUMENTS

| | | |
|---|---|---|
| GB | 821242 | 10/1959 |
| GB | 1344839 | 6/1971 |
| JP | 59190213 | * 10/1984 |
| JP | 62280733 | 12/1987 |
| JP | 08301703 | 11/1996 |
| JP | 2000-229947 | 8/2000 |
| JP | 2003/017148 | 1/2003 |
| JP | 2004269414 A | 9/2004 |
| JP | 2004277351 | 10/2004 |
| JP | 2003-364894 | 1/2005 |
| SU | 1727789 | 7/1965 |
| WO | 199104668 | * 4/1991 |
| WO | WO 91/04668 | 4/1991 |
| WO | WO 9104668 | 4/1991 |
| WO | WO 97/05182 | 2/1997 |
| WO | WO 00/32658 | 6/2000 |
| WO | WO 01/85093 | 11/2001 |
| WO | WO 2005/054241 | 6/2005 |
| WO | WO 2006/012513 | 2/2006 |
| WO | WO 2007/124397 | 11/2007 |
| WO | WO 2008/110007 | 9/2008 |
| WO | WO 2009/103062 | 8/2009 |
| WO | WO 2009103064 | 8/2009 |

OTHER PUBLICATIONS

Vasserman, Sbornik Nauch. Rabot, Rizhskii Med. Inst. (1956), (No. 5), 23-36.*
Vasserman, Sbornik Nauch. Rabot, Rizhskii Med. Inst. (1956), (No. 5), 23-36 (CAS Abstract).*
JP 59190213 (CAS Abstract), Oct. 1984.*
Anderson et al., Anal. Chem. 2003, 75, 4851-4858.*
Anderson et al., Anal. Chem. 1999, 71, 3873-3876.*
Anderson et al., J. Am. Chem. Soc. 2005, 127, 593-604.*
International Search Report, PCT/US05/26036, Dated May 3, 2006.
U.S. Appl. No. 12/023,468, filed Jan. 31, 2008, Armstrong et al.
Welton, T. *Chem. Rev.* 1999, 99, 2071-2083.
Cadena, C.; Anthony, J.L.; Shah, J.K.; Morrow, T.I.; Brennecke, J.F.; Maginn, E.J. *J. Am. Chem. Soc.* 2004, 126, 5300-5308.
Visser, A.E.; Swatloski, R.P.; Reichert, W.M.; Mayton, R.; Sheff, S.; Wierzbicki, A.; Davis, J.H.; Rogers, R.D. *Environ. Sci. Technol.* 2002, 36, 2523-2529.
Anderson, J.L.; Armstrong, D.W., *Anal. Chem.* 2003, 75, 4851-4858.
Anderson, J.L.; Pino, V.; Hagberg, E.C.; Sheares, V.V.; Armstrong, D.W., *Chem. Commun.* 2003, 2444-2445.
Fletcher, K.A.; Pandey, S. *Langmuir* 2004, 20, 33-36.
Zhou, Y.; Antonietti, M., *J. Am. Chem. Soc.* 2003, 125, 14960-14961.
Luo, H.; Dai, S.; Bonnesen, P.V.; Buchanan, A.C.; Holbrey, J.D.; Bridges, N.J.; Rogers, R.D. *Anal. Chem.* 2004 (76)3078-83.
Wu, J.; Zhang, J.; Zhang, H.; He, J.; Ren, Q.; Guo, M., *Biomacromolecules* 2004, 5, 266-268.
Vijayaraghavan, R.; MacFarlane, D.R., *Chem. Commun.* 2004, 700-701.
Boxall, D.L.; Osteryoung, R.A., *J. Electrochem. Soc.* 2004, 151, E41-E45.
Earle, M.J.; Katdare, S.P.; Seddon, K.R., *Org. Lett.* 2004, 6, 707-710.
Carter, E.B.; Culver, S.L.; Fox, P.A.; Goode, R.D.; Ntai, I.; Tickell, M.D.; Traylor, R.K.; Hoffman, N.W.; Davis, J.H. *Chem. Commun.* 2004, 630-631.
Wasserscheid, P.; Hilgers, C.; Keim, W., *Journal of Molecular Catalysis A* 2004, 214, 83-90.
Gao, H.; Jiang, T.; Han, B.; Wang, Y.; Du, J.; Liu, Z.; Zhang, J., *Polymer* 2004, 45, 3017-3019.
Kaar, J.L.; Jesionowski, A.M.; Berberich, J.A.; Moulton, R.; Russell, A.J., *J. Am. Chem. Soc.* 2003, 125, 4125-4131.
Zhao, H.; Malhotra, S.V. *Biotechnology Letters* 2002, 24, 1257-1260.
Lee, J.K.; Kim, M-J., *J. Org. Chem.* 2002, 67, 6845-6847.
Wilkes, J.S., *Journal of Molecular Catalysis A: Chemical* 2004, 214, 11-17.
Bonhote, P.; Dias, A.-P.; Papageorgiou, N.; Kalyanasundaram, K.; Gratzel, M. *Inorg Chem.* 1996, 35, 1168.
Wei, G-T.; Yang, Z.; Lee, C-Y.; Yang, H-Y.; Wang, C.R., *J. Am. Chem. Soc.* 2004, 126, 5036-5037.
Itoh, H.; Naka, K.; Chujo, Y., *J. Am. Chem. Soc.* 2004, 126, 3026-3027.
Katritzky, A.R.; Jain, R.; Lomaka, A.; Petrukhin, R.; Karelson, M.; Visser, A.E.; Rogers, R.D, *J. Chem. Inf. Comput. Sci.* 2002, 42, 225-231.
Eike, D.; Brennecke, J.F.; Maginn, E.J., *Green Chem.* 2003, 5, 323.
Forsyth, S.A.; Pringle, J.M.; MacFarlane, D.R., *Aust. J. Chem.* 2004, 57, 113-119.
Dzyuba, S.V.; Bartsch, R.A., *Chem. Phys. Phys. Chem.* 2002, 3, 161-166.
Seddon, K.R.; Stark, A.; Torres, M-J., ACS Symposium Series 2002, 819 (Clean Solvents: Alternative Media for Chemical Reactions and Processing), 34-49.
Carda-Broch, S.; Berthod, A.; Armstrong, D.W., *Anal. Bioanal. Chem.* 2003, 375, 191.
Baranyai, K.J.; Deacon, G.B.; MacFarlane, D.R.; Pringle, J.M.; Scott, J.L., *Aust. J. Chem.* 2004, 57, 145-147.
Van Valkenburg, M.E.; Vaughn, R.L.; Williams, M.; Wilkes, J.S. Proceedings—Electrochemical Society 2002, 2002-19 (Molten Salts XIII), 112-123.
Anderson, J.L.; Ding, J.; Welton, T.; Armstrong, D.W., *J. Am. Chem. Soc.* 2002, 124, 14247-14254.
Blessing, R.H., *Acta Cryst.* 1995, A51, 33-38.
Law, G.; Watson, P.R., *Langmuir* 2001, 17, 6138-6141.
Ngo, H.L.; LeCompte, K.; Hargens, L.; McEwen, A.B., *Thermochimica Acta* 2000, 357-358, 97-102.
Hu, X.; Tang, Y.; Gantzel, P.; Meyer, K., *Organometallics* 2003, 22, 612-614.
Bryce, M.R., *Chem. Soc. Rev.* 1991, 20, 355-390.
Holbrey, J.D.; Reichert, W.M.; Nieuwenhuyzen, M.; Johnston, S.; Seddon, K.R.; Rogers, R.D., *Chem. Commun.* 2003, 1636-1637.
Dearden, J.C., *Sci. Total Environ.* 1991, 59, 109-110.
Bondi, A.-J., *J. Phys. Chem.* 1964, 68, 441-453.
Anderson, J.L.; Ding, R.; Ellem, A,; Armstrong, D.W. *J Am. Chem. Sac.* 2005, 127, 593-604.
Terazima, M.; Nogami, Y.; Tominaga, T. *Chemical Physical Letters* 2000,332, 503-507.
Van Hook, J.P.; Tobolsky, A.V. *J. Am. Chem. Soc.* 1958,80,779-782.
Abraham, M. H. *Chem. Soc. Rev.* 1993, 22, 73.
Abraham, M. H.; Whiting, G. S.; Doherty, R. M.; Shuely, W. J. *J Chromatogr.* 1991,587,229-236.
Bouche, J.; Verzele, M. *J Gas Chromatogr.* 1968, 6, 501.
Muldoon, M.J.; Gordon, C.M. *J Polym. Sci. Part A: Polym. Chem.* 2004, 42, 3865-3869.
Marcilla, R.; Blazquez, J.A.; Rodriguez, J.; Pomposo, J.A.; Mecerreyes, D. *J Polym. Sci. Part A: Polym. Chem.* 2004,42,208-212.
Armstrong, D. W.; He, L.; Liu, L.-S. *Anal. Chem.* 1999, 71, 3873-3876.
Anderson, J.L.; Armstrong, D.W. *Anal. Chem.* 2003, 75,4851-4858.
Lord & Pawliszym, *J. Chromatogr.* A 885 (2000) 153-193.
Liu et al. "Disposable ionic liquid coating for headspace solid-phase microextraction of benzene, toluene, ethyl benzene, and xylenes in plants followed by gas chromatography—flame ionization detection," *J. Chromatogr.* A (2005), 1066 (1-2), 27-32.
Vas, G.; Vekey, K., J. Mass Spectrometery (2004) 39, 233-254.
Abraham M H, et al., "XVII. The Characterisation of 24 Gas-Liquid Chromatographic Stationary Phases Studied by Poole and Co-Workers, Including Molten Salts, and Evaluation of Solute-Stationary Phase Interactions",*J. Chromatogr.*, 587:229-236 (1991).
Anderson J L, et al., "High-Stability Ionic Liquids. A New Class of Stationary Phases for Gas Chromatography", *Anal. Chem.*, 75:4851-4858 (2003).
Bitterer F, et al., "Tertiary Alkylphosphanes with Ammonium Groups in the Side Chains—Amphiphiles with Basic P Atoms", *Chem. Ber.*, 128:275-279 (1995).
Brophy J J, et al., "The Cleavage of Bisphosphonium Salts by Sodium Hydride", *Chem. Comm.*, 15:531-532 (1966).
Grob K Jr., et al., "Comprehensive, Standardized Quality Test for Glass Capillary Columns", *J. Chromatogr.*, 156:1-20 (1978).
Grob K, et al., "Testing Capillary Gas Chromatographic Columns", *J. Chromatogr.*, 219:13-20 (1981).

Han X and Armstrong D W, "Using Geminal Dicationic Ionic Liquids as Solvents for High-Temperature Organic Reactions," *Org. Lett.*, 7(19):4205-4208 (2005).

Horn P E, et al., "The Reactions of Organic Derivatives of Elements Capable of Valency-shell Expansion. Part VII. Further Experiments with Quaternary Phosphonium Salts", *J. Chem. Soc.*, 1036-1044 (1963).

International Search Report for PCT/US2008/052583 dated Mar. 25, 2009.

Jin C M, et al., "Polyethylene Glycol Functionalized Dicationic Ionic Liquids With Alkyl or Polyfluoroalkyl Substituents as High Temperature Lubricants", *J. Mater. Chem.*, 16:1529-1535 (2006).

Kostyanovskii R G, et al., "Geminal Systems. $19^{th}$ Reactions of Aminomethylphosphines with Electrophilic Reagents", *Bull. Acad. Sci. USSR*, 31:1433-1441 (1982).

Lundberg K L, et al., "gem-Dibasic Ligands with Phosphorus, Sulfur, and Nitrogen Sites, and Some Borane Derivatives", *Inorg. Chem.*, 8:1336-1340 (1969).

Martinelango P K et al., "Gas-Phase Ion Association Provides Increased Selectivity and Sensitivity for Measuring Perchlorate by Mass Spectrometry", *Anal. Chem.*, 77:4829-4835 (2005).

Payagala T, et al., "Unsymmetrical Dicationic Ionic Liquids: Manipulation of Physicochemical Properties Using Specific Structural Architectures", *Chem. Mater.*, 19:5848-5850 (2007).

Remsburg J W, et al., "Evaluation of Dicationic Reagents for Their Use in Detection of Anions Using Positive Ion Mode ESI-MS Via Gas Phase Ion Association", *J. Am. Chem. Soc.*, 19:2, 261-269 (2007).

Adams CJ, et al., "Friedel-Crafts reactions in room temperature ionic liquids", *Chem. Comm.*, 2097-2098 (1998).

Allen CR, et al., Facile synthesis of ionic liquids possessing chiral carboxylates, Tetrahedron Lett. 47:7367-7370 (2006).

Arimura T, et al.,*Template Effects on Calixarene Conformations Through Host-Guest Type Interactions*, Tetrahedron Lett. 30(19):2563-2566 (1989).

Bao W, et al., "Synthesis of chiral ionic liquids from natural amino acids", *J. Org. Chem.*, 68:591-593 (2003).

Barber DW, et al., "The chromatography of gases and vapours. Part VI. Use of the stearates of bivalent manganese, cobalt, nickel, copper, and zinc as column liquids in gas chromatography", *Am. J. Chem. Soc.*, 18-24 (1959).

Baudequin C, et al., "Ionic liquids and chirality: oppportunities and challenges", *Tet. Asym.*, 14:3081-3093 (2003).

Berthod A, et al., "Ionic liquids as stationary phase solvents for methylated cyclodetrins in Gas Chromatography", *Chromatographia*, 53:63 (2001).

Biedron et al., "Ionic liquids as reaction media for polymerization processes; atomic transfer radical polymerization (ATRP) of acdrylates in ionic liquids", *Polym. Int.*, 52:1584-1588 (2003).

Branco LC, et al., "Highly selective transport of organic compounds by using supported liquid membranes based on ionic liquids", *Angew. Chem. Int. Ed. Engl.*, 41(15):2771-2773 (2002).

Brovtsyna NB, et al, *Biologicheskie Membrany*, (1996), 13(1):57-70.

Carmichael AJ, et al., "Ionic Liquids: Improved syntheses and new products", *ACS Symposium Series*, 856:14-31 (2003).

Cavallito CJ, et al., *Archives Internationales de Pharmacodynamie et de Therapie*, (1955), 101:38-48.

Chauvin Y, et al., "A novel class of versatile solvents for two-phase catalysis: hydrogenation, isomerization, and hydroformylation of alkenes catalyzed by rhodium complexes in liquid 1,3-dialkylimidazolium salts", *Angew. Chem. Int. Ed. Engl.*, 34:2698-2700 (1995).

Chellappan K, et al., *A Calix[4]Imidazolium[2] Pyridine as an Anion Receptor*, Angew. Chem. Int. Ed. 44(19):2899-2903 (2005).

Cornils B, et al., *Aqueous-Phase Organometallic Catalysis: Concepts and Applications*, Wiley-VCH: Weinheim, (1998), 555-563.

"Cyclodextrin stationary phases for chiral separations and highly selective achiral separations", *Chiraldex Handbook*, $6^{th}$ Ed., Advanced Separation Technologies, 8 (2002).

Earle MJ, et al., "Diels-Alder reactions in ionic liquids: A safe recyclable alternative to lithium perchlorate-diethyl ether mixtures", *Green Chem.*, 23-25 (1999).

Fischer T, et al., "Diels-Alder reactions in room-temperature ionic liquids", *Tet. Lett.*, 40:793-796 (1999).

Furton KG, et al., "Solute-solvent interactions in liquid alkylammonium 4-toluenesulfonate salts studied by gas chromatography", *Anal. Chem.*, 59(8):1170-1176 (1987).

Handy ST, "Greener solvents: room temperature ionic liquids from biorenewable sources", *Chemistry—A European Journal*, 9(13):2938-2944 (2003).

Haramoto Y, et al., "Liquid crystal properties of new ionic liquid crystal compounds having a 1,3-dixane ring", *Liquid Crystals*, 29(1):87-90 (2002).

Herrmann WA, et al., "Chiral heterocyclic carbenes in asymmetric homogenous catalysis", *Angew. Chem. Int. Ed. Engl.*, 35:2805-2807 (1996).

Hideg K and Hankovszky OH, *Benzazoles, III. Alkylation of Benzimidazoles*, ACTA Chimica Academiae Scientarum Hungaricae 49(3):303-310 (1966).

Hong-Yang et al, *Design and synthesis of novel chiral liquids and their application in free radical polymerization of methyl methacrylate* Chinese Journal of Polymer Science (2003) 21(3) 265-270.

Howell BA, et al., *High phosphorus/bromine content compounds as polyolefin flame retardants*, Recent Advances in Flame Retardancy of Polymeric Materials, 7:119-126 (1997).

Howarth J, et al., "Moisture stable dialkylimidazolium salts as heterogeneous and homogeneous lewis acids in the Diels-Alder reaction", *Tet. Lett.*, 38(17):3097-3100 (1997).

Hu X, et al., *A Bis-Carbenealkenyl Copper(I) Complex from a Tripodal Tris-Carbene Ligand*, Organometallics 22(15):3016-3018 (2003).

Hu X, et al., *Copper Complexes of Nitrogen-Anchored Tripodal N-Heterocyclic Carbene Ligands*, J. Am. Chem. Soc. 125(40):12237-12245 (2003).

Hu X, et al., *Dioxygen Activation by a Low-Valent Coblat Complex Employing a Flexible Tripodal N-Heterocyclic Carbene Ligand*, J. Am. Chem. Soc. 126(41):13464-13473 (2004).

Hu X, et al., *Group 11 Metal Complexes of N-Heterocyclic Carbene Ligands: Nature of the Metal-Carbene Bond*, Organometallics 23(4):755-764 (2004).

Hu X, et al., *Terminal Cobalt(III) Imido Complexes Supported by Tris(Carbene) Ligands: Imido Insertion into the Cobalt-Carbene Bond*, J. Am. Chem. Soc. 126(50):16322-16323 (2004).

Huddleston JG, et al., "Room temperature ionic liquids as novel media for "clean" liquid-liquid extraction", *Chem. Comm.*, 1765-1766 (1998).

Ilies MA, et al., *Lipophilic Pyrylium Salts in the Synthesis of Efficient Pyridinium-Based Cationic Lipids, Gemini Surfactants, and Lipophilic Oligomers for Gene Delivery*, J. Med. Chem. 49(13):3872-3887 (2006).

Ishida Y, et al., "Design and synthesis of a novel imidazolium-based ionic liquid with planar chirality", *Chem. Comm.*, 2240-2241 (2002).

Jodry JJ, et al., "New chiral imidazolium ionic liquids: 3D-network of hydrogen bonding", *Tet. Lett.*, 45:4429-4431 (2004).

Kawahara S and Uchimaru T, *One-Pot Preparation of o-Xylylene Diamine and its Related Amines*, Zfitschrift Fuer Naturforschung, B: Chemical Sciences, 55(10):985-987 (2000).

Kim H and Kang J, *Iodide Selective Fluorescent Anion Receptor with Two Methylene Bridged Bis-Imidazolium Rings on Naphthalene*, Tetrahedron Lett. 46(33):5443-5445 (2005).

Kiss L, et al., "Further insight into the mechanism of Heck oxyarylation in the presence of chiral ligands", *ARKIVOC*, v:69-76 (2003).

Kwon JY, et al., *Fluorescent GTP-Sensing in Aqueous Solution of Physiological pH*, J. Am. Chem. Soc. 126(29):8892-8893 (2004).

Lane ES, et al., *Quaternary ammonium nitrates. Part II. Reaction of nitratoalkyl ethers, amines, amides, and urethanes with tertiary amines and related compounds* J. Chem. Soc. 2006-2010 (1956).

Lee CW, "Diels-Alder reactions in chloroaluminate ionic liquids acceleration and selectivity enhancement", *Tet. Lett.*, 40:2461-2462 (1999).

Levillain J, et al., "Synthesis and properties of thiazoline based ionic liquids derived from the chiral pool", *Chem. Comm.*, 2914-2915 (2003).

Liu J, et al., *Imidazolylidene Carbene Ligated Palladium Catalysis of the Heck Reaction in the Presence of Air*, Org. Biomol. Chem. 1(18):3227-3231 (2003).

Löhr HG, et al., *Organylammonium-Wirtsubstanzen als vielseitige Clathratbildner*, Chem. Ber. 117(4):1487-1496 (1984).

Ludley P, et al., "Phosphonium tosylates as solvents for the Diels-Alder reaction", *Tet. Lett.*, 42:2011-2014 (2001).

Mamane V, et al., *Palladium-Catalyzed Cross-Coupling Reaction of a Chiral Ferrocenyl Zinc Reagent with Aromatic Bromides: Application to the Design of Chiral Octupoles for Second Harmonic Generation*, Synthesis 3:455-467 (2003).

Mas-Marzá E, et al., *Carbene Complexes of Rhodium and Iridium from Tripodal N-Heterocyclic Carbene Ligands: Synthesis and Catalytic Properties*, Inorg. Chem. 43(6):2213-2219 (2004).

Mas-Marzá E, et al., *Synthesis and Catalytic Properties of Two Trinuclear Complexes of Rhodium and Iridium with the N-Heterocyclic Tris-carbene Ligand TIMEN$^{iPr}$*, Organometallics 24(13):3158-3162 (2005).

McCullough D, et al., *Glued Langmuir-Blodgett Bilayers from Porous Versus Nonporous Surfactants*, J. Am. Chem. Soc. 126(32):9916-9917 (2004).

Mizzoni RH, et al., *Polyamine Salts with Autonomic Blocking Properties*, J. Am. Chem. Soc. 76:2414-2417 (1954).

Molodykh ZV, et al., *Antimicrobial Activity of Ortho-Aminomethylphenols and Their Derivatives*, Pharm. Chem. J. 21(2):110-114 (1987).

Moody EW, et al., *Journal of Radioanalytical and Nuclear Chemistry*, (2001), 248(2):431-437.

Ohki A, et al., *Sensing of Poly(Styrenesulfonate)s by Polymeric Membrane Electrodes Based on Liquid Anion-Exchangers*, Bull. Chem. Soc. JPN., 70(4):799-804 (1997).

Pacholec F, et al., "Molten organic salt phase for gas-liquid chromatography", *Anal. Chem.*, 54(12):1938-1941 (1982).

Parenty ADC, et al., *General One-Pot, Three-Step Methodology Leading to an Extended Class of N-Heterocyclic Cations: Spontaneous Nucleophilic Addition, Cyclization, and Hydride Loss*, J. Org. Chem. 69(18):5934-5946 (2004).

Patinec V, et al., *The Use of Triquaternary Alkylammonium Ions in the Synthesis of STA-5, a Magnesioaluminophosphate with the BPH Framework* Topology, Chemistry of Materials 11(9):2456-2562 (1999).

Patrascu C, et al., "New pyridinium chiral ionic liquids", *Heterocycles*, 63:2033-2041 (2004).

Pégot B, et al., "First application of chiral ionic liquids in asymmetric Baylis-Hillman reaction", *Tet. Lett.*, 45:6425-6428 (2004).

Pomaville RM, et al., "Solute-solvent interactions in liquid tetrabutylammonium sulfonate salts studied by gas chromatography", *Anal. Chem.*, 60(11):1103-1108 (1988).

Poole CF, et al., "Chemometric evaluation of the solvent properties of liquid organic salts", Analyst, 120:289-294 (1995).

Poole CF, et al., "Survey of organic molten salt phases for gas chromatography", *J. Chromatography*, 289:299-320 (1984).

Rehse K and Kämpfe M, *Oligotertiäre Amine und Oligoquartäre Ammoniumsalze*, Archiv Der Pharmazie 322:811-815 (1989).

Schilf W, et al., *NMR and X-ray Investigations of Model Tris- and Bis-Pyridinium Fluoroborates*, J. Mol. Struct. 707(1-3):115-121 (2004).

Shinkai S, et al., *Ion Template Effects on the Conformation of Water-Soluble Calixarenes*, J. Org. Chem. 56(1):295-300 (1991).

Soai K, et al., "Chiral quaternary ammonium salts as solid-state catalysts for the enantioselective addition of diethylzinc to aldehydes", *Chem. Comm.*,. 1:43-44 (1990).

Soukup-Hein RJ, et al., *Evaluating the Use of Tricationic Reagents for the Detection of Doubly Charged Anions in the Positive Mode by ESI-MS*, Anal. Chem.80(7):2612-2616 (2008).

Stark A, et al., "1-Ethyl-3-methylimidazolim halogenoaluminate ionic liquids as solvents for Friedel-Crafts acylation reactions of ferrocene", *J. Chem. Soc., Dalton Trans.*, 63-66 (1999).

Suarez PAZ, et al., "The use of new ionic liquids in two-phase catalytic hydrogenation reaction by rhodium complexes", *Polyhedron*, 15(7):1217-1219 (1996).

Thanh G, et al., Solvent-free microwave-assistant preparation of chiral ionic liquids from (-)-N-methylephedrine, *Eur. J. Org. Chem.*, 5:1112-1116 (2004).

Tosoni M, et al., "Synthesis of novel chiral ionic liquids and their phase behavior in mixtures with smectic and nematic liquid crystals", *Helv. Chim. Acta*, 87:2742-2749 (2004).

Ujiie S, et al., "Ion complex type of novel chiral smectic C* liquid crystal having chiral hydrogen tartrate counterion", *Chem. Lett.*, 23(1):17-20 (1994).

Vasserman, *Sbornik Nauch. Rabot, Rizhskii Med. Inst.*, (1956), 5:23-36, Abstract.

Wang Y, *Synthesis and application of novel chiral ionic liquids derived from α-Pinene*, Masters Thesis, (2003), New Jersey Institute of Technology, Department of Chemistry and Environmental Science.

Wasserscheid P, et al., "Synthesis and properties of ionic liquids derived from the chiral pool", *Chem. Comm.*, 200-201 (2002).

Wong WWH, et al., *Tetrakis(imidazolium)Macrocyclic Receptors for Anion Binding*, Org. Biomol, Chem. 3(23):4201-4208 (2005).

Zhao et al., *Suzuki Cross-Coupling Mediated by Tetradentate N-Heterocyclic Carbene (NHC)-Palladium Complexes in an Environmentally Benign Solvent*, Org. Biomol. Chem. 1(10):1643-1646 (2003).

Office Action, dated Sep. 9, 2008 issued in U.S. Appl. No. 11/177,093.

Office Action, dated Sep. 17, 2008 issued in U.S. Appl. No. 11/701,537.

Office Action, dated May 6, 2009 issued in U.S. Appl. No. 11/701,537.

Office Action, dated Sep. 9, 2009 issued in U.S. Appl. No. 11/701,537.

Office Action, dated Oct. 20, 2009 issued in the U.S. Appl. No. 12/331,108.

International Search Report, PCT/US2005/26036, dated Jun. 16, 2006.

International Search Report, PCT/US2005/24188, dated Feb. 5, 2007.

International Search Report, PCT/US2008/052590, dated Mar. 3, 2009.

International Search Report, PCT/US2009/034293, dated Apr. 15, 2009.

International Search Report, PCT/US2009/034290, dated Apr. 21, 2009.

International Search Report, PCT/US2008/052583, dated Sep. 18, 2009.

Brune, et al. (1970) "Chlorophyllin a-catalyzed photoreduction of viologen dyes (Krasnovsky Reaction)" Archives of Biochemistry and Biophysics, 141:371-373.

Kordosky, et al. (1973) "Tetramethyldiphosphine and flexible aliphatic (dimethylphosphino) ligands" Inorganic Synthesis, vol. XIV, 14-23.

Oshikiri, et al. (2005) "Kinetic control of threading of cyclodextrins onto axle molecules" Journal of the Chemical Society, 127:12186-12187.

Rothstein, et al. (1953) "The reactions of organic derivatives of elements capable of valency-shell expansion. Part II Unsaturated quaternary phosphonium salts" 3994-4004.

Vasserman (1956) Sbornik Nauch. Rabot, Rizhskii Med. Inst., 5:23-36.

Office Action, dated Jul. 26, 2010 issued in U.S. Appl. No. 11/701,537.

Office Action, dated Sep. 9, 2010 issued in U.S. Appl. No. 11/701,537.

Anderson, et al. (2006) "Ionic Liquids in analytical chemistry" American Chemical Society, Analytical Chemistry, 2893-2902.

Berthod, et al. (2008) "Ionic liquids in separation techniques" Journal of Chromatography A 1184:6-18.

Breitbach, et al. (2008) "Characterization of phosphonium ionic liquids through a linear solvation energy relationship and their use as GLC stationary phases" Anal Bioanal Chem 390:1605-1617.

Han, et al. (2007) "Ionic liquids in separations" Acc. Chem. Res. 40:1079-1086.

Huang, et al. (2007) "PEG-linked geminal dicationic ionic liquids as selective, high-stability gas chromatographic stationary phases" Anal Bioanal Chem 389:2265-2275.

Office Action, dated Feb. 8, 2011 issued in U.S. Appl. No. 11/701,537.

Vasudevan V. Namboodiri, et al., Organic Letters, "*Solvent-Free Sonochemical Preparation of Ionic* Liquids" 2002 4(18), pp. 3161-3163.

Office Action, dated Jan. 3, 2012 issued in U.S. Appl. No. 11/701,537.

Georges et al. (2004) Organic & Biomolecular Chemistry 2(19), 2751-2756.

Hu, X. (2003) "Copper complexes of nitrogen-anchored tripodal N-Heterocyclic carbene ligands" J. Am. Chem. Soc. 2003, 125.

Kasa (1998), Acta Medica (Hradec Kralove, Czech Republic) 41(1), 19-21.

Sunggoo, Y. (2003) "Molecular Recognition of Fluoride Anion: Benzene-Based Tripodal Imidazolium Receptor" J. Org. Chem. 68, 2467-2470.

Abstract of Weiss et al.: Zeitschrift fuer Naturforschung, B: Chemical Sciences (1998), 53(8), 916-926 Database Caplus Chemical Abstracts Service, Columbus, Ohio, US; Database Accession No. 1998:576962.

Zhao, Y. (2003) "Suzuki cross-coupling mediated by tetradentate N-heterocyclic carbene (NHC)-palladium complexes in an environmentally benign solvent" Org. Biomol. Chem., 1, 1643-1646.

Office Action, dated Mar. 11, 2010 issued in U.S. Appl. No. 11/701,537.

Office Action, dated May 9, 2011 issued in U.S. Appl. No. 12/023,468.

Office Action, dated Aug. 18, 2011 issued in U.S. Appl. No. 11/701,537.

\* cited by examiner

HIGH STABILITY DIIONIC LIQUID SALTS

CROSS-REFERENCE TO RELATED APPLICATIONS

This application claims the benefit of the filing date of U.S. Provisional Patent Application No. 60/590,857 filed Jul. 23, 2004, the disclosure of which is hereby incorporated herein by reference.

BACKGROUND OF THE INVENTION

One of the more rapidly growing areas of chemistry research involves room temperature ionic liquids (RTILs). The wide range of possible cation and anion combinations allows for a large variety of tunable interactions and applications.[1-18] The uses and applications of RTILs have traversed many areas of chemistry[1-15] and even areas of biochemistry.[16-18] Reported thermal stability ranges of 300° C. in some cases,[19-20] their ability to solubilize a variety of disparate molecules, and the fact that ionic liquids can be synthesized that are immiscible with both water and nonpolar organic solvents further add to their usefulness.[21-22] While much work involving RTILs deals with their use as "green" solvents in organic synthesis, their characterization and the understanding of their unique physico-chemical and solvation properties are important areas of ongoing investigation. Although the number of ionic liquids described in the literature is growing rapidly, the relationship between their structure/make-up and their physico-chemical properties and solvation properties is not well understood. Some research in the field of ionic liquids has explored their fundamental properties in hopes that it would become apparent which cation-anion combinations give rise to specific and/or desired qualities.[23-24] Thus far, this approach has met with only limited success.

Early work seemed to indicate that the anionic constituents of ionic liquids may have a greater influence on their physical and chemical properties.[25] However, this notion may be due, in part, to the fact that the ionic liquids studied contained not only a variety of different anions, but closely related, structurally similar cations. Indeed, anions such as halides possess higher hydrogen bond basicity character (Cl>Br>I) and readily hydrogen bond to generally form viscous liquids. This is not to say that only coordinating anions produce viscous liquids; it is well known the viscosity of 1-alkyl-3-methylimiazolium ionic liquids are found to increase with increasing alkyl chain length even when paired with non-coordinating anions such as hexafluorophosphate ($PF_6^-$) and bis(trifluoromethylsulfonyl)imide ($NTf_2^-$).[26-27] While the cation and its structure can certainly influence the surface tension, melting point, viscosity, density, and thermal stability as well as interact via dipolar, $\pi$-$\pi$, and n-$\pi$ interactions with dissolved molecules, its range of effects has not been studied as extensively as it has for anions.

Despite their touted stability, many of the more common ionic liquids are susceptible to chemical and thermal degradation.[4, 28-30] Recently, it was reported that when 1-butyl-3-methylimidazolium chloride (BMIM-Cl) is exposed to the atmosphere and heated, it begins to turn from a pale yellow to amber color at 120° C.[28] When heated further, the ionic liquid begins to show obvious signs of decomposition at and above 150° C.[28] Most recently, a new class of "high stability ionic liquids" based on bulky cations and triflate anions were introduced and it was reported that the robustness of some of the more traditional ionic liquids appear to be less than previously thought (in terms of both lower thermal stability and higher volatility).[4] MacFarlane and co-workers reached similar conclusions via use of the 'step tangent method' for thermogravimetric analysis (TGA) to more accurately determine degradation temperatures of imidazolium-based cations.[29] They point out that significant evolution of volatile degradation products takes place well below previously reported degradation temperatures. A maximum operating temperature parameter was proposed to provide a more appropriate estimate of thermal stability using TGA.[29]

The techniques of solid phase extraction and solid phase microextraction are known.[52, 54] However, the use of diionic liquid salts and immobilized ionic liquids have not been disclosed in connection with these techniques. Ionic liquids have been used in task-specific liquid-liquid extraction for use in extraction of $Hg^{2+}$ and $Cd^{2+}$ from water.[53] However, diionic liquid salts have not been used in task-specific solid phase extraction/microextraction, nor have absorbed, adsorbed or immobilized ionic liquids been used in these techniques.

SUMMARY OF THE INVENTION

In one embodiment, the present invention comprises a stable liquid salt of a dication or dianion having a solid/liquid transformation temperature at 400° C. or less. In another embodiment, the present invention comprises a stable liquid salt of a dication or dianion having a solid/liquid transformation temperature at about 100° C. or less. In another embodiment, the present invention comprises a stable liquid salt of a dication or dianion having a solid/liquid transformation temperature at about 60° C. or less. In another embodiment, the present invention comprises a stable liquid salt of a dication or dianion having a solid/liquid transformation temperature at about 25° C. or less.

In one embodiment, the present invention comprises a liquid salt of a dication or dianion which will not substantially decompose or volatilize at a temperature below 200° C. In another embodiment, the present invention comprises a liquid salt of a dication or dianion which will not substantially decompose or volatilize at a temperature below 300° C.

In one embodiment, the present invention comprises a stable liquid salt of a dication or dianion having a liquid range of about 200° C. or more. In another embodiment, the present invention comprises a stable liquid salt of a dication having a liquid range of about 300° C. or more, and even more preferably 400° C. or more.

In one embodiment, the present invention comprises a stable liquid salt of a dianion or dication having a solid/liquid transformation temperature at about 100° C. or less, which will not substantially decompose and is substantially nonvolatile at a temperature below 200° C. or has a liquid range of about 200° C. or more. In another embodiment, the stable liquid salt of a dianion or dication has a solid/liquid transformation temperature at about 100° C. or less, will not substantially decompose and is substantially nonvolatile at a temperature below 200° C. and has a liquid range of about 200° C. or more. In another embodiment, the present invention comprises a stable liquid salt of a dianion or dication having a temperature of solid/liquid transformation temperature at 25° C. or less, which will not substantially decompose and is substantially nonvolatile at a temperature below 300° C. or has a liquid range of about 300° C. or more. In another embodiment, the stable liquid salt of a dianion or dication has a solid/liquid transformation temperature at 25° C. or less, will not substantially decompose and is substantially nonvolatile at a temperature below 300° C. and has a liquid range of about 300° C. or more.

In another embodiment, the present invention provides a stable diionic liquid comprising at least one liquid salt of dianionic molecule or dicationic molecule of the structure of formula I or II:

C-A-B-A'  (I)

or

C'-A-B-A'-C''  (II)

wherein A and A' are ether both anions or both cations, or are both groups which overall have an anionic or cationic charge and which may be the same or different, so long as they both have the same charge (positive or negative); B is a bridging group (also referred to as a chain or bridging moiety) that may be substituted or unsubstituted, saturated or unsaturated, aliphatic, including straight or branched chains, cyclic or aromatic, and which may contain, in addition to carbon atoms and hydrogen, N, O, S and Si atoms; and C, C' and C'' are counter ions having a charge which is opposite that of A and A'. C' and C'' are ether both mono-anionic or mono-cationic or groups which have a single anionic or cationic charge and may be the same or different so long as they both have the same charge (positive or negative) and C is ether dianionic or dicationic or contains two groups which each have a single anionic or cationic charge (while C is not shown as ionically bound to both A and A', in a preferred embodiment, it is the counter ion for both).

In another embodiment, A and A' are cationic and are, without limitation, substituted or unsubstituted, saturated or unsaturated, aliphatic including straight or branched chain, cyclic or aromatic, quaternary ammonium, protonated tertiary amine, phosphonium or arsonium groups. When A and A' are cationic, C' and C'' are anionic counterions which, without limitation, include halogens, mono-carboxylates mono-sulfonates, mono-sulphates, $NTf_2^-$, $BF_4^-$, trifilates or $PF_6^-$, and C is a dianionic molecule having two anionic groups each selected from, without limitation, carboxylate, sulfate or sulfonate groups. In another embodiment, A and A' are anionic and are, without limitation, substituted or unsubstituted, saturated or unsaturated, aliphatic including straight or branched chain, cyclic or aromatic, carboxylates, sulfonates, and sulphates. When A and A' anionic, C' and C'' are cationic counterions which, without limitation, include quaternary ammonium, protonated tertiary amine, phosphonium or arsonium groups. C is a dicationic molecule which can be, without limitation, a compound having two cationic groups each selected from quaternary ammonium, protonated tertiary amine, phosphonium or arsonium groups. In another embodiment, these dianionic ionic liquids will have both a solid/liquid transformation temperature at about 100° C. or less and a liquid range of at least 200° C. In a particularly preferred embodiment, these liquid salts of formula I or II have a solid/liquid transition temperature at about 100° C. or less and/or a liquid range of 200° C. or more and/or are substantially non-volatile and non-decomposable at temperatures below 200° C. Diionic liquid salts in accordance with one aspect of the invention may have one or more stereogenic centers and may be optically enhanced. The counterions may, instead or in addition, have one or more stereogenic centers and may be optically enhanced.

The present invention also contemplates polymers of diionic liquid salts, cross-linked diionic materials and the use of cross-linked and non-cross-linked diionic materials as the stationary phase in columns used in chromatography and extraction. Chromatographic columns including a stationary phase of cross-linked or non-cross-linked diionic materials are also contemplated. In certain columns, diionic liquid salts may be mixed with monoionic materials.

Indeed, in one aspect of the present invention, there are provided immobilized ionic liquids including high stability diionic liquid salts (with or without monoionic materials) as stationary phases, particularly in gas chromatography. These stationary phases are highly selective, highly stable, and highly resistant to temperature degradation. These materials can be non-cross-linked (which often means that they are absorbed or adsorbed on a solid support or column), can be "partially" cross-linked or "more highly" cross-linked (which often means that they are "immobilized" on a solid support or column) and can be composed of a mixture of diionic liquid salts and mono-ionic materials or can be made completely of diionic liquid salts in accordance with the present invention. In the case of non-cross-linked stationary phases, the diionic salts used may be saturated, unsaturated or a mixture of both. It should be understood, however, particularly if some amount of unsaturated diionic liquid salts are used, and especially where heat is used to fix the stationary phase, or the stationary phase is heated during use, as in GC, some degree of cross-linking is possible. "Partially" cross-linked stationary phases in accordance with the present invention permit production of a more stable, highly selective stationary phase, allowing for high efficiency separations at temperatures up to approximately 280° C. In "partially cross-linked" stationary phases, there will be a mixture of mono and diionic species and the amount of diionic liquid salts used will be equal to or less than the amount of monoionic species used. "More highly" cross-linked stationary phases in accordance with the present invention can provide superior efficiency and stability even at temperatures up to 350° C. and higher. In "more highly cross-linked" stationary phases, the amount of diionic species (diionic liquids/salts) will surpass that of any monoionic species. Indeed, preferably, more highly cross-linked stationary phases will be composed substantially exclusively (90% or more) of immobilized diionic liquid salts in accordance with the invention. Indeed, they are most preferably purely diionic liquid salts. In either case, the monoionic species and the diionic species used should include unsaturation. The monoionic species will generally have a single multiple bond while the diionic liquid salts will generally have two or more multiple bonds (double bonds/ triple bonds). These unsaturated bonds not only allow cross-linking, but also facilitate immobilization. Mixtures of saturated and unsaturated species may also be used, particularly in the case of non-cross-linked stationary phases. In one preferred embodiment, the stationary phases are made from a diionic species which is chiral and optically enhanced. Moreover, cross-linking and/or immobilization of the ionic liquids in a column as a stationary phase, or to a solid support for SPE, SPME, task-specific SPE or SPME, SPME/MALDI or other analytical or separation technique, does not appear to affect the selectivity of the stationary phase, thereby preserving its dual nature retention behavior.

And while stationary phases for gas chromatography and in particular capillary GC are one preferred aspect of the present invention, the diionic liquid salts, either alone or in combination with mono-ionic liquids, can be used as a stationary phase in other forms of chromatography including, for example, liquid chromatography ("LC") and high performance liquid chromatography ("HPLC"). Not only are the methods of creating stationary phases, solid supports and/or columns containing same contemplated, the stationary phases, solid supports and columns themselves and the use of columns and solid supports containing these stationary phases in chromatography, another analytical or separation techniques are contemplated as specific aspects of the invention.

Thus, ionic liquids, and in particular diionic liquid salts in accordance with the present invention can be used in analytical and separation technologies other than chromatography, all of which are considered as part of the present application. For example, ionic liquids and diionic liquid salts in accordance with the present invention can be used in, without limitation, solid phase extraction ("SPE"), solid phase microextraction ("SPME"), task-specific SPME ("TSSPME"), and certain types of mass spectrometry known as solid phase microextraction/MALDI. The invention includes not only the use of ionic liquids and, in particular, diionic liquid salts in these techniques, but also solid supports to which ionic liquids, and in particular, diionic liquid salts, are absorbed, adsorbed or immobilized as well as sampling device such as, for example, pipettes, automatic pipettes, syringes, microsyringes and the like incorporating ionic liquids and diionic liquid salts which can be used in such analytical and separation techniques.

Another embodiment of the present invention is the individual salt molecules or diionic salts which form the diionic liquids (both dicationic ionic liquids and dianionic ionic liquids) of the present invention. One particularly preferred diionic salt is

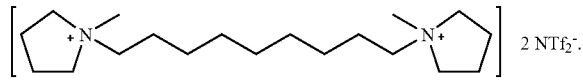

However, any anion may be used to form the salt. Other preferred diionic liquid salts in accordance with the invention are illustrated in Tables 1, 2, 3, and A. Solvents comprising this diionic salt, and thus comprised a dicationic ionic liquid of this salt are also preferred.

In yet another embodiment, the present invention provides a diionic liquid salt ("liquid" meaning liquid salts at either room temperature (25° C.) or at a temperature above the solid/liquid transformation temperature, which may be 400° C. or less, unless otherwise indicated) having a solid/liquid transformation temperature which is about 400° C. or less, said diionic liquid salt including two monoionic groups separated by a bridging group and either two monoionic counter ions or at least one diionic counter ion. Preferably, the two monoionic groups are both cationic or anionic and in another embodiment, they are germinal (the same). When cationic, it is preferred that the groups are quaternary ammonium, protonated tertiary amine, thionium phosphonium or arsonium groups which may be substituted or unsubstituted, saturated or unsaturated, linear, branched, cyclic or aromatic. When anionic, the groups are preferably carboxylate, sulfate or sulfonate groups which may be substituted or unsubstituted, saturated or unsaturated, linear, branched, cyclic or aromatic. In a particularly preferred embodiment, these diionic liquid salts include at least one unsaturated bond which can facilitate cross-linking and/or immobilization.

In another embodiment, these diionic liquids as just described can be used as a solvent for dissolution, suspension or dispersion of solids or liquid mixed therewith or as a reaction solvent for chemical reactions. Both are intended by the term solvent. Preferably, a solvent comprising: a diionic liquid salt as noted above having a solid/liquid transition temperature is about 400° C. or less and having a liquid range of about 200° C. or more and in another embodiment, a stability as measured by being substantially non-volatile at a temperature of about 200° C. or below. Both diionic liquid salts and the solvents made there from may be chiral and optically enhanced.

Another embodiment of the present invention is a device useful in chemical separation or analysis comprising: a solid support and at least one diionic liquid salt as described above adsorbed, absorbed or immobilized thereon. The device may be a column used in HPLC or GC wherein the solid support is packed in a chromatographic column or wherein the solid support is a capillary column useful in gas chromatography.

The device may also be a syringe having a hollow needle defining an inner space, the needle being disposed at an end of a barrel and a plunger disposed within the barrel, the solid support being attached, mounted or affixed, irremovably or removably, (collectively "attached") to the syringe such that it may be retracted into the inner space of the needle when the plunger is retracted from the barrel and exposed from within the needle when the plunger is inserted into the barrel. In one embodiment, the syringe is a microsyringe. In some embodiments the diionic liquids used in these devices also include monoionic materials which may be simply mixed therewith or which may be cross-liked to the diionic liquid salts of the invention. These may be absorbed, adsorbed or immobilized on the solid support. When immobilized, it is preferred that these ionic species include unsaturated groups. In another aspect of the invention, especially where the device is a syringe or is used in SPE or any type of SPME, it is possible to use monoionic liquids which do not include diionic liquid salts. However, in such instances, they are preferably immobilized on the solid support.

In one other embodiment, there is provided a method of separating one chemical from a mixture of chemicals comprising the steps of: providing a mixture of at least one first and at least one second chemical, exposing that mixture to at least one solid support including ionic liquids and in particular a diionic liquid salt as described above using a device as described above and retaining at least a portion of the first chemical on the solid support for some period of time. "Retaining" in this context does not mean permanently. Separation can occur in a syringe device by removal of the device from the sample or ejection of the second chemical. In the case of a chromatography column, the first chemical will be absorbed or adsorbed at a different rate than the second chemical, which may be at a greater rate or a lower rate, thus resulting in separation. Both are moved through the column by a mobile phase, which can be a liquid or a gas and their interaction with the stationary phase (the ionic liquid materials on the solid support) at different rates causes separation. This is what is meant by "retention" in the context of chromatography. However, in certain types of chromatography, it is also possible that the first chemical is bound to the stationary phase while the second chemical is not and is carried through the column by the mobile phase until it elutes. The first chemical can be eluted or removed separately and this is also embraced by the word "retained."

DETAILED DESCRIPTION

Figure 1:
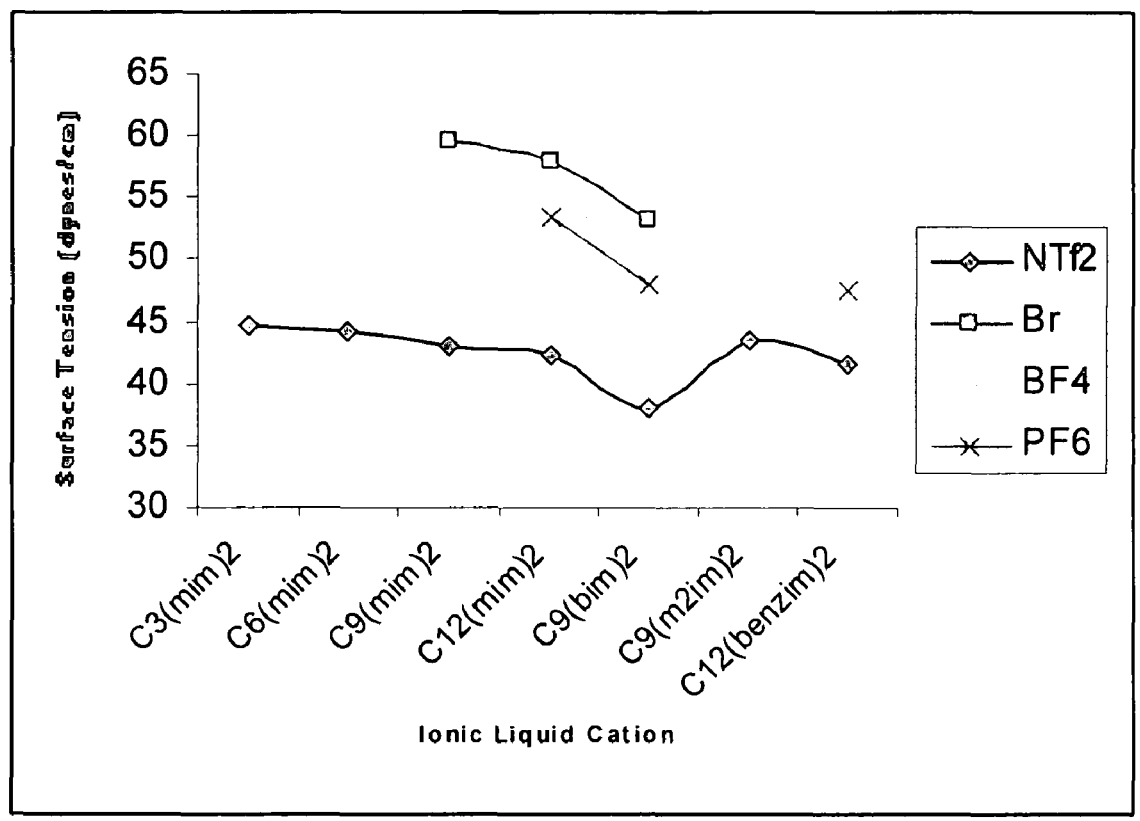
FIG. 1 illustrates the effect of the cation and anion on the surface tension for dicationic ionic liquids.

While the specification concludes with the claims particularly pointing and distinctly claiming the invention, it is believed that the present invention will be better understood from the following description. All percentages and ratios used herein are by weight of the total composition and all measurements made are at 25° C. and normal pressure unless otherwise designated. All temperatures are in Degrees Celsius unless specified otherwise. The present invention can comprise (open ended) or consist essentially of the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise. As used herein, "consisting essentially of" means that the invention may include ingredients in addition to those recited in the claim, but only if the additional ingredients do not materially alter the basic and novel characteristics of the claimed invention. Preferably, such additives will not be present at all or only in trace amounts. However, it may be possible to include up to about 10% by weight of materials that could materially alter the basic and novel characteristics of the invention as long as the utility of the compounds (as opposed to the degree of utility) is maintained. All ranges recited herein include the endpoints, including those that recite a range "between" two values. Terms such as "about," "generally," "substantially," and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value.

A "diionic salt" or "DIS" is a salt formed between a dication as described herein and a dianion or two anions or between a dianion as described herein and a dication or two cations. This term is not meant to embrace a single species that has a +2 or −2 charge such as Mg$^{+2}$ or SO$_4^{-2}$. Rather it contemplates a single molecule with two discreet mono-ionic groups, usually separated by a bridging group. The two ionic species should be of the same charge. They may be different types of groups or the diionic liquid salts may be "geminal" which means both ionic groups are not only the same charge, but also the same structure. The counterions need not be identical either. In one embodiment, either the diion or the salt forming species is chiral, having at least one stereogenic center. In such instances, the diionic liquid salts may be racemic (or in the case of diastereomers, each pair of enantiomers is present in equal amounts) or they may be optically enhanced. "Optically enhanced" in the case of enantiomers means that one enantiomer is present in an amount which is greater than the other. In the case of diastereomers, at least one pair of enantiomers is present in a ratio of other than 1:1. Indeed, the diionic liquid salts may be "substantially optically pure" in which one enantiomer or, if more than one stereogenic center is present, at least one of the pairs of enantiomers, is present in an amount of at least about 90% relative to the other enantiomer. The diionic liquid salts of the invention may also be optically pure, i.e., at least about 98% of one enantiomer relative to the other. Usually, the term diionic salt is used to describe a salt molecule, although, as the context suggests, it may be used synonymously with "diionic liquid" ("DIL") and "diionic liquid salt" ("DILS"). A "diionic liquid" or "DIL" in accordance with the present invention is a liquid comprised of diionic salts. Thus, sufficient DS molecules are present such that they exist in liquid form at the temperatures indicated herein. This presumes that a single DS molecule is not a liquid. A DL is either a dicationic ionic liquid or a dianionic ionic liquid (a liquid comprising either dicationic salts or dianionic salts as described herein). A "dicationic ionic liquid" (used synonymously with "liquid salts of a dication") in accordance with the present invention is a liquid comprised of molecules which are salts of dicationic species. The salt forming counter-anions may be mono-ionic such as, for example only, Br-, or dianionic, such as, again for example only, succinic acid. Any dicationic ionic liquid which is stable and has a solid/liquid transformation temperature of 400° C. or less is contemplated. The same is true for "dianionic ionic liquids" also known as "liquid salts of a dianion," except the charges are reversed. Dicationic liquids and dianionic liquids can also be referred to herein as diionic liquid salts ("DILS" or "DCLS" and "DALS" depending upon charge).

Preferably, a dicationic ionic liquid or dianionic ionic liquid will not substantially decompose or volatilize (or remain substantially non-volatile) as measured by being immobilized as a thin film in a fused silica capillary or on a silica solid support as described herein, at a temperature of 200° C. or less. "Substantially" in this context means less than about 10% by weight will decompose or volatilize at 200° C. inside a capillary over the course of about one hour. Moreover, the dicationic ionic liquid in accordance with this embodiment will preferably have either a solid/liquid transformation temperature at about 100° C. or less or a liquid range (the range of temperatures over which it is in a liquid form without burning or decomposing) of at least 200° C.

In another embodiment, these dicationic ionic liquids will have both a solid/liquid transformation temperature at about 100° C. or less and a liquid range of at least 200° C.

In another aspect of the invention, a dicationic ionic liquid will not substantially volatilize or decompose, as discussed herein, at a temperature of less than about 300° C. "Substantially" in this context means that less than about 10% by weight will decompose or volatilize at 300° C. inside a capillary over the course of about one hour. Moreover, the dicationic ionic liquids in accordance with this embodiment will preferably have either a solid/liquid transformation temperature at 25° C. or less. In another embodiment, the dicationic ionic liquids will also have a liquid range of at least 200° C. In an even more preferred aspect of the invention, the liquid range will be 300° C. or above.

Preferably, a dianionic ionic liquid will not substantially decompose or volatilize as measured by being immobilized as a thin film in a fused silica capillary as described herein, at a temperature of 200° C. or less. Moreover, the dianionic ionic liquid in accordance with this embodiment will preferably have either a solid/liquid transformation temperature at about 100° C. or less or a liquid range of at least 200° C.

In another embodiment, these dianionic ionic liquids will have both a solid/liquid transformation temperature at about 100° C. or less and a liquid range (diionic molecule is stable over the entire temperature range) of at least 200° C.

In another aspect of the invention, a dianionic ionic liquid will not substantially volatilize or decompose, as discussed herein, at a temperature of less than about 300° C. Moreover, the dianionic ionic liquids in accordance with this embodiment will preferably have either a solid/liquid transformation temperature at about 25° C. or less. In another embodiment, the dianionic ionic liquids will also have a liquid range of at least 200° C. In an even more preferred aspect of the invention, the liquid range will be 300° C. or above.

Thus a diionic liquid in accordance with the present invention is either a dicationic ionic liquid salt or a dianionic ionic liquid salt which will neither substantially decompose nor substantially volatilize, as measured as described herein, as a temperature of 200° C. or less and will have a temperature of solid/liquid transformation temperature at 100° C. or a liquid range of at least 200° C.

In other aspects of the invention, these diionic liquids will have both solid/liquid transformation temperature at about 100° C. or more and a liquid range of at least 200° C.

In other embodiments in accordance with the present invention, the diionic liquids, either dicationic ionic liquids or dianionic ionic liquids will be stable, that is not substantially volatilized or decomposed, as discussed herein, at a temperature of less than about 300° C. and will have a solid/liquid transformation temperature at about 25° C. or less. A particular preferred embodiment of this aspect of the present invention, the diionic liquids will have a liquid range of at least 200° C. and even more preferably at least 300° C. Any diionic compound which can form a stable liquid salt that meets the broadest parameters is contemplated.

In another embodiment, the present invention provides a stable diionic liquid comprising at least one liquid salt of dianionic molecule or dicationic molecule of the structure of formula I or II:

C-A-B-A'                (I)

or

C'-A-B-A'-C"           (II)

wherein A and A' are ether both anions or both cations, or are both groups which overall have an anionic or cationic charge and which may be the same or different, so long as they both have the same charge (positive of negative); B is a bridging group (also referred to as a chain or bridging moiety) that may be substituted or unsubstituted, saturated or unsaturated, aliphatic, including straight or branched chains, cyclic or aromatic, and which may contain, in addition to carbon atoms and hydrogen, N, O, S and Si atoms; and C, C' and C" are counter ions having a charge which is opposite that of A and A'. C' and C" are ether both mono-anionic or mono-cationic or groups which have a single anionic or cationic charge and may be the same or different so long as they both have the same charge (positive or negative) and C is ether dianionic or dicationic or contains two groups which each have a single anionic or cationic charge.

In another embodiment, A and A' are cationic and are, without limitation, substituted or unsubstituted, saturated or unsaturated, aliphatic including straight or branched chain, cyclic or aromatic, quaternary ammonium, protonated tertiary amine, phosphonium or arsonium groups. When A and A' are cationic, C' and C" are anionic counterions which, without limitation, include halogens, mono-carboxylates mono-sulfonates, mono-sulphates, $NTf_2^-$, $BF_4^-$, triflates or $PF_6^-$, and C is a dianionic molecule having two anionic groups each selected from, without limitation, carboxylate, sulfate or sulfonate groups. In another embodiment, A and A' are anionic and are, without limitation, substituted or unsubstituted, saturated or unsaturated, aliphatic including straight or branched chain, cyclic or aromatic, carboxylates, sulfonates, and sulphates. When A and A' anionic, C' and C" are cationic counterions which, without limitation, include quaternary ammonium, protonated tertiary amine, phosphonium or arsonium groups. C is a dicationic molecule which can be, without limitation, a compound having two cationic groups each selected from quaternary ammonium, protonated tertiary amine, phosphonium or arsonium groups. In another embodiment, these dianionic ionic liquids will have both a temperature of solid/liquid transformation of about 100° C. or less and a liquid range of at least 200° C. In a particularly preferred embodiment, these liquid salts of formula I or II have a solid/liquid transition temperature of from about 100° C. or less and/or a liquid range of 200° C. or more and/or are substantially non-volatile and non-decomposable at temperatures below 200° C.

Typically, the structural considerations for diionic liquids are the same whether they are dianionic ionic liquids or dicationic ionic liquids. First, the diionic liquids will include a diionic species, either a dianionic or a dicationic molecule. The ionic species are normally separated by a chain or bridging moiety or group as discussed herein. Any anion or cation which can provide a dianionic ionic liquid or dicationic ionic liquid is contemplated. These include those that are identified above as A and A'. Possible cations include, without limitation, quaternary ammonium $[-N(R)_3]^+$, protonated tertiary amines $^{+[-N(R)}{}_2H]^+$, phosphonium and arsonium groups. These groups can be aliphatic, cyclic, or aromatic. Examples of aliphatic ammonium dications are found in Table 2 and examples aromatic ammonium dications are found in Table 1. Anions may include, for example, carboxylates, sulfates, or sulphonates. Examples of a dicarboxylic acid dianion include, without limitation, succinic acid, nonanedioic acid, and dodecanedioic acid. Other non-limiting examples of diionic species (dianions and dications including a generic bridging group) include:

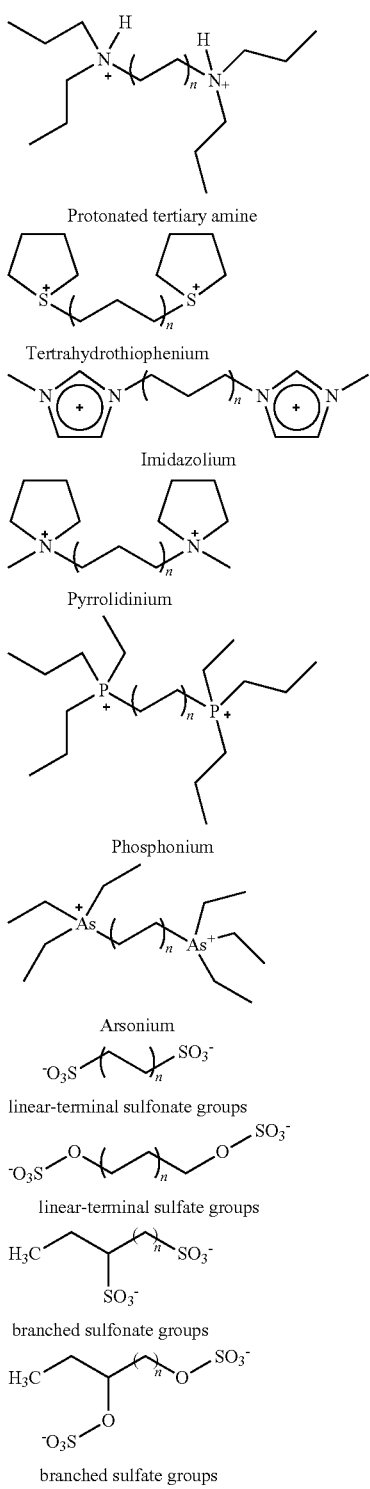

The value of n is discussed in connection with the length of the bridging group. In addition, hybrid dianions and dications are contemplated. Thus, for illustration only, a dication can be composed of a quaternary ammonium group and an arsonium group and a dianion can be composed of a carboxylate group and a sulphonate. The counter ions may also be different from each other.

The bridging group or chain interposed between the two ionic species can be any length or any composition which affords a diionic liquid of suitable properties. These include the groups identified as B above. There are certain factors that should be considered in selecting such a chain or bridging moiety. First, the larger the diionic molecule in general, the greater the chance that the melting point or temperature of solid/liquid transformation will be elevated. This may be less of a concern where the liquid range need not be extensive and the temperature of solid/liquid transformation need not be terribly low. If, however, one desires a liquid range of about 200° C. or more and/or a solid/liquid transformation temperature at 100° C. or less, the size of the overall molecule can become a larger and larger factor. Second, the chain should have some flexibility. An excessive degree of unsaturated groups, the use of very rigid and/or stericly bulky groups can adversely impact the ability of the resulting materials to act as solvents and reduce their overall and utility. Thus, multiple fused ring structures, such as those found in, for example, cholesterol, and polyunsaturated aliphatic groups with extensive unsaturation should generally be avoided.

In general, the length of the bridging group can range from a length equivalent to that of a saturated aliphatic carbon chain of between about 2 and about 40 carbon atoms (e.g., $n=C_2-C_{40}$ when bridging group is composed of carbon). More preferably, the length should be approximately that resulting from a saturated aliphatic carbon chain of about 3 to about 30 carbon atoms in length.

The chain or bridging group may be aliphatic, cyclic, or aromatic, or a mixture thereof. It may contain saturated or unsaturated carbon atoms or a mixture of same with, for example, alkoxy groups (ethoxy, propoxy, isopropoxy, butoxy, and the like). It may also include or be made completely from alkoxy groups, glycerides, glycerols, and glycols. The chain may contain hetero-atoms such as O, N, S, or Si and derivatives such as siloxanes, non-protonated tertiary amines and the like. The chain may be made from one or more cyclic or aromatic groups such as a cyclohexane, a immidazole, a benzene, a diphenol, a toluene, or a xylene group or from more complex ring-containing groups such as a bisphenol or a benzidine. These are merely representative and are not meant to be limiting. Generally, however, the bridging group will not contain an ionically charged species, other than the dianions or dications.

The diionic liquids of the present invention are generally salts, although they may exist as ions (+1, −1, +2, −2) in certain circumstances. Thus, in most instances, each ion should have a counterion, one for each anion or cation. Charge should be preserved. In the case of a dianionic ionic liquid, two cations (including those identified as C' or C") (or one dication) (including those identified as C) are required and in the case of a dicationic ionic liquid, two anions (including those identified as C' or C") (or one dianion) (including those identified as C) are required. The choice of anion can have an effect of the properties of the resulting compound and its utility as a solvent. And, while anions and cations will be described in the context of a single species used, it is possible to use a mixture of cations to form salts with a dianionic species to form a dianionic ionic liquid. The reverse is true for dications. For clarity sake, the salt-forming ions will be referred to as counterions herein.

Cationic counterions can include any of the dicationic compounds previously identified for use in the production of dicationic ionic liquids. In addition, monoionic counterparts of these may be used. Thus, for example, quaternary ammonium, protonated tertiary amines, phosphonium, and arsonium groups are useful as cationic counterions for dianionic molecules to form dianionic ionic liquids in accordance with the present invention.

Similarly, anionic counterions can be selected from any of the dianionic molecules discussed herein useful in the creation of dianionic ionic liquids. These would include dicarboxylates, disulphonates, and disulphates. The corresponding monoionic compounds may also be used including carboxylates, sulphonates, sulphates and phosphonates. Halogens may be used as can triflate, $NTf_2^-$, $PF_6^-$, $BF_4^-$ and the like. The counterions should be selected such that the diionic liquids have good thermal and/or chemical stability and have a solid/liquid transformation temperature and/or a liquid range as described herein. Finally, the ionic groups of the present invention can be substituted or unsubstituted. They may be substituted with halogens, with alkoxy groups, with aliphatic, aromatic, or cyclic groups, with nitrogen-containing species, silicon-containing species, with oxygen-containing species, and with sulphur-containing species. The degree of substitution and the selection of substituents can influence the properties of the resulting material as previously described in discussing the nature of the bridge or chain. Thus, care should be taken to ensure that excessive steric hindrance and excessive molecular weight are avoided, that resulting materials does not lose its overall flexibility and that nothing will interfere with the ionic nature of the two ionic species.

The diionic liquids of the present invention can be used in pure or in substantially pure form as carriers or as solvents. "Substantially" in this context means no more than about 10% of undesirable impurities. Such impurities can be either other undesired diionic salts, reaction by-products, contaminants or the like as the context suggests. In an intended mixture of two or more DILS, neither would be considered an impurity. Because they are non-volatile and stable, they can be recovered and recycled and pose few of the disadvantages of volatile organic solvents. Because of their stability over a wide liquid range, in some instances over 400° C., they can be used in chemical synthesis that require both heating and cooling. Indeed, these solvents may accommodate all of the multiple reaction steps of certain chemical syntheses. Of course, these diionic liquids may be used in solvent systems with cosolvents and gradient solvents and these solvents can include, without limitation, chiral ionic liquids, chiral non-ionic liquids, volatile organic solvents, non-volatile organic solvents, inorganic solvents, water, oils, etc. It is also possible to prepare solutions, suspensions, emulsions, colloids, gels and dispersions using the diionic liquids.

In addition to discrete diionic salts and diionic liquid salts, it is also possible to produce polymers of these materials. Polymers may include the diionic salts within the backbone or as pendant groups and they may be cross-linked or non-cross-linked.

In addition to being useful as solvents and reaction solvents, the dianionic liquids of the present invention can be used to perform separations as, for example, the stationary phase for gas-liquid chromatography. Dicationic ionic liquid salts, which may be used for exemplification include: (1) two vinyl imidazolium or pyrrolidinium dications separated by an alkyl linkage chain (of various length) or (2) one vinyl imidazolium or pyrrolidinium cation separated an alkyl linkage chain (of various length) and connected to a methyl, ethyl, propyl, or buylimidazolium cation or a methyl, ethyl, propyl, or butylpyrrolidinium cation. See below. Any anionic counterion discussed may be used. Note that the presence of unsaturated groups facilitates cross-linking and/or immobilization.

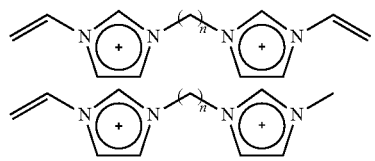

Dianionic anions can also be used with either monocations or dications to form a variety of different ionic liquid combinations. When a dication is used, anyone is used as charge balance must be preserved. The dianionic anions can be of the dicarboxylic acid type (i.e., succinic acid, nonanedioic acid, dodecanedioic acid, etc), as shown below.

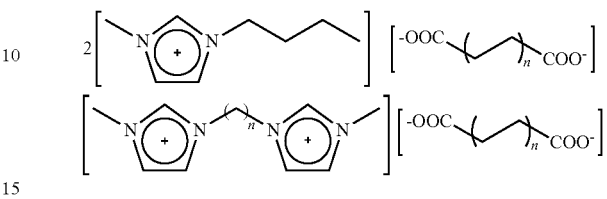

Diionic liquid salts can be coated on a capillary (or solid support) and optionally, subsequently polymerized and/or cross-linked by, for example, two general methods. In the first method, the ionic liquid are coated via the static coating method at 40° Celsius using coating solution concentrations ranging from 0.15-0.45% (w/w) using solutions of methylene chloride, acetone, ethyl acetate, pentane, chloroform, methanol, or mixtures thereof. After coating of the ionic liquid is complete, the column is purged with helium and baked up to 100° Celsius. The efficiency of naphthalene is then evaluated to examine the coating efficiency of the monomer ionic liquid stationary phase. If efficiency is deemed sufficient, the column is then flushed with vapors of azo-tert-butane, a free radical initiator, at room temperature. After flushing with the vapors, the column is then fused at both ends and heated in an oven using a temperature gradient up to 200° Celsius for 5 hours. The column gradually cooled and then re-opened at both ends, and purged with helium gas. After purging with helium gas overnight, the column is then heated and conditioned up to 200° Celsius. After conditioning, the column efficiency is then examined using naphthalene at 100° Celsius and the stationary phase coated layer examined under a microscope. Note that the cross-linking process can, and often does, also cause immobilization. "Immobilized" in the context of the invention means covalently or ionically bound to a support or to another ionic liquid (including diionic liquid salts) or both. This is to be compared with ionic liquids which may be absorbed or adsorbed on a solid support. Solid support in these particular instances were intended to include columns.

It is not necessary, however, to cross-link these materials prior to their use in GC. They may be adsorbed or absorbed in a column, or indeed on any solid support. However, at higher temperatures, their viscosity may decrease and they can, in some instances, flow and collect as droplets which can change the characteristics of the column.

Another method involves adding up to 2% of the monomer weight of 2,2'-azobisisobutyronitrile ("AIBN") free radical initiator to the coating solution of the monomer. The capillary column is then filled with this solution and coated via the static coating method. After coating, the capillary column is then sealed at both ends and placed in an oven and conditioned up to 200° Celsius for 5 hours. The column is gradually cooled and then re-opened at both ends, and purged with helium gas. After purging with helium gas overnight, the column is then heated and conditioned up to 200° Celsius. After conditioning, the column efficiency is then examined using naphthalene at 100° Celsius and the stationary phase coated layer examined under a microscope.

In addition to the free radical polymerization of an alkene, other polymerization reactions involving other functional groups either attached to the aromatic ring of the cation, the linkage chain connecting two cations (to form a dication), or the anion can be achieved. Examples of such reactions may include cationic and anionic chain growth polymerization reactions, Ziegler-Natta catalytic polymerization, and step-reaction polymerization. The use of two different monomers to form copolymers through addition and block copolymerization can also be achieved. Additionally, condensation polymerization can be used to connect through functional groups such as amines and alcohols. All polymerization and cross-linking reactions discussed in the following 2 references can be used: "Comprehensive Polymer Science—The synthesis, Characterization, Reactions and Applications of Polymers" by Sir Geoffrey Allen, FRS; "Comprehensive Organic Transformations: a guide to functional group preparations" by Richard C. Larock. 2nd Edition. Wiley-VCH, New York. Copyright, 1999. ISBN: 0471190314.

The production of these 39 dicationic liquid salts are described. The following materials were used: 1-methylimidazole; 1-methylpyrrolidine; 1-butylpyrrolidine; 1,2-dimethylimidazole; 1-butylimidazole; 1-benzylimidazole; 1,3-dibromopropane; 1,6-dibromohexane; 1,9-dibromononane; 1,12-dibromododecane; 1-bromo-3-chloropropane; hexafluorophosphoric acid, sodium tetrafluoroborate, N-lithiotrifluoromethylsulfonimide, silver nitrate, and phosphorus pentoxide were all purchased from Aldrich (Milwaukee, Wis.). Hexafluorophosphoric acid is toxic and corrosive and must be handled with care. Acetone, ethyl acetate, and 2-propanol were purchased from Fisher Scientific (Fair Lawn, N.J.). Untreated fused silica capillary tubing (0.25-mm i.d.) was purchased from Supelco (Bellefonte, Pa.).

The following diionic salts may be produced. (See Tables 1, 2 and 3.)

TABLE 1

Physicochemical properties of imidazolium-based dicationic ionic liquids[a]

| # | Ionic Liquid | Molecular Weight (g/mol) | Surface Tension (dynes/cm) | Density (g/cm$^3$) | Temperature of[b] Solid/Liquid Transformation (° C.) | Refractive Index | Miscibility with Heptane | Miscibility with Water |
|---|---|---|---|---|---|---|---|---|
| 1 | $C_3(mim)_2$-Br | 366.10 | — | — | 162[c] | — | Immiscible | Miscible |
| 2 | $C_3(mim)_2$-$NTf_2$ | 766.58 | 44.7 | 1.61 | −4 | 1.440 | Immiscible | Immiscible |
| 3 | $C_3(mim)_2$-$BF_4$ | 379.90 | — | — | 117 | — | Immiscible | Miscible |
| 4 | $C_3(mim)_2$-$PF_6$ | 496.22 | — | — | 131 | — | Immiscible | Immiscible |
| 5 | $C_6(mim)_2$-Br | 408.18 | — | — | 155 | — | Immiscible | Miscible |
| 6 | $C_6(mim)_2$-$NTf_2$ | 808.66 | 44.2 | 1.52 | >−14, <−4 | 1.441 | Immiscible | Immiscible |
| 7 | $C_6(mim)_2$-$BF_4$ | 421.98 | — | — | 92 | — | Immiscible | Miscible |
| 8 | $C_6(mim)_2$-$PF_6$ | 538.30 | — | — | 136 | — | Immiscible | Immiscible |
| 9 | $C_9(mim)_2$-Br | 450.26 | 59.6 | 1.41 | 6 | 1.549 | Immiscible | Miscible |
| 10 | $C_9(mim)_2$-$NTf_2$ | 850.74 | 43.1 | 1.47 | −14 | 1.442 | Immiscible | Immiscible |
| 11 | $C_9(mim)_2$-$BF_4$ | 464.06 | 61.2 | 1.33 | −4 | 1.469 | Immiscible | Miscible |
| 1 | $C_3(mim)_2$-Br | 366.10 | — | — | 162[c] | — | Immiscible | Miscible |
| 2 | $C_3(mim)_2$-$NTf_2$ | 766.58 | 44.7 | 1.61 | −4 | 1.440 | Immiscible | Immiscible |
| 3 | $C_3(mim)_2$-$BF_4$ | 379.90 | — | — | 117 | — | Immiscible | Miscible |
| 4 | $C_3(mim)_2$-$PF_6$ | 496.22 | — | — | 131 | — | Immiscible | Immiscible |
| 5 | $C_6(mim)_2$-Br | 408.18 | — | — | 155 | — | Immiscible | Miscible |
| 6 | $C_6(mim)_2$-$NTf_2$ | 808.66 | 44.2 | 1.52 | >−14, <−4 | 1.441 | Immiscible | Immiscible |
| 7 | $C_6(mim)_2$-$BF_4$ | 421.98 | — | — | 92 | — | Immiscible | Miscible |
| 8 | $C_6(mim)_2$-$PF_6$ | 538.30 | — | — | 136 | — | Immiscible | Immiscible |
| 9 | $C_9(mim)_2$-Br | 450.26 | 59.6 | 1.41 | 6 | 1.549 | Immiscible | Miscible |
| 10 | $C_9(mim)_2$-$NTf_2$ | 850.74 | 43.1 | 1.47 | −14 | 1.442 | Immiscible | Immiscible |
| 11 | $C_9(mim)_2$-$BF_4$ | 464.06 | 61.2 | 1.33 | −4 | 1.469 | Immiscible | Miscible |
| 12 | $C_9(mim)_2$-$PF_6$ | 580.38 | — | — | 88 | — | Immiscible | Immiscible |
| 13 | $C_{12}(mim)_2$-Br | 492.34 | 57.9 | 1.27 | −17 | 1.540 | Immiscible | Miscible |
| 14 | $C_{12}(mim)_2$-$NTf_2$ | 892.82 | 42.3 | 1.40 | −26 | 1.443 | Immiscible | Immiscible |
| 15 | $C_{12}(mim)_2$-$BF_4$ | 506.14 | 55.8 | 1.26 | −19 | 1.503 | Immiscible | Partially Miscible |
| 16 | $C_{12}(mim)_2$-$PF_6$ | 622.46 | 53.4 | 1.36 | 9 | 1.436 | Immiscible | Immiscible |
| 17 | $C_9(bim)_2$-Br | 534.42 | 53.1 | 1.27 | >0, <23 | 1.545 | Immiscible | Miscible |
| 18 | $C_9(bim)_2$-$NTf_2$ | 934.90 | 38.0 | 1.35 | >−42, <−8 | 1.446 | Immiscible | Immiscible |
| 19 | $C_9(bim)_2$-$BF_4$ | 548.22 | 50.4 | 1.20 | >−42, <−8 | 1.503 | Immiscible | Partially Miscible |
| 20 | $C_9(bim)_2$-$PF_6$ | 664.54 | 48.0 | 1.30 | >0, <23 | 1.439 | Immiscible | Immiscible |
| 21 | $C_3(m_2im)_2$-Br | 394.15 | — | — | 298 | — | Immiscible | Miscible |
| 22 | $C_3(m_2im)_2$-$NTf_2$ | 794.63 | — | — | 91 | — | Immiscible | Immiscible |
| 23 | $C_3(m_2im)_2$-$PF_6$ | 524.27 | — | — | 264 | — | Immiscible | Immiscible |
| 24 | $C_9(m_2im)_2$-Br | 478.31 | — | — | 174 | — | Immiscible | Miscible |
| 25 | $C_9(m_2im)_2$-$NTf_2$ | 878.79 | 43.5 | 1.47 | >−42, <−8 | 1.448 | Immiscible | Immiscible |
| 26 | $C_9(m_2im)_2$-$BF_4$ | 492.11 | 58.1 | 1.31 | >0, <23 | 1.456 | Immiscible | Miscible |
| 27 | $C_9(m_2im)_2$-$PF_6$ | 608.43 | — | — | 130 | — | Immiscible | Immiscible |
| 28 | $C_{12}(benzim)_2$-Br | 644.53 | — | — | 151 | — | Immiscible | Immiscible |
| 29 | $C_{12}(benzim)_2$-$NTf_2$ | 1045.01 | 41.5 | 1.37 | >−8, <0 | 1.482 | Immiscible | Immiscible |
| 30 | $C_{12}(benzim)_2$-$PF_6$ | 774.65 | 47.4 | 1.27 | −15 | 1.484 | Immiscible | Immiscible |

[a]Patents pending

[b]Difficulty arises in determining the melting points of some ionic liquids as they prefer the glass-state. Therefore, for some ionic liquids in which the exact melting point/glass transition temperature could not be easily determined, a temperature range is provided. A detailed discussion related to the polymorphic nature of many of these ionic liquids is provided in the section titled "*Crystal Structures of Geminal Dicationic Ionic Liquids*"

[c]This ionic liquid exhibited physico-chemical properties very similar to the 1-butyl-3-methylimidazolium chloride ionic liquid making it difficult to fully characterize.

TABLE 2

Physicochemical properties of pyrrolidinium-based dicationic ionic liquids[a]

| # | Ionic Liquid | Molecular Weight (g/mol) | Surface Tension (dynes/cm) | Density (g/cm$^3$) | Temperature of[b] Solid/Liquid Transformation (° C.) | Refractive Index | Miscibility with Heptane | Miscibility with Water |
|---|---|---|---|---|---|---|---|---|
| 31 | C$_3$(mpy)$_2$-Br | 372.18 | — | — | 51[c] | — | Immiscible | Miscible |
| 32 | C$_3$(mpy)$_2$-NTf$_2$ | 772.67 | — | — | 206 | — | Immiscible | Immiscible |
| 33 | C$_3$(mpy)$_2$-PF$_6$ | 502.30 | — | — | 359 | — | Immiscible | Immiscible |
| 34 | C$_9$(mpy)$_2$-Br | 456.34 | — | — | 257 | — | Immiscible | Miscible |
| 35 | C$_9$(mpy)$_2$-NTf$_2$ | 856.83 | 42.2 | 1.41 | >−8, <0 | 1.436 | Immiscible | Immiscible |
| 36 | C$_9$(mpy)$_2$-PF$_6$ | 586.46 | — | — | 223 | — | Immiscible | Immiscible |
| 37 | C$_9$(bpy)$_2$-Br | 540.50 | — | — | 216 | — | Immiscible | Miscible |
| 38 | C$_9$(bpy)$_2$-NTf$_2$ | 940.98 | — | — | 84 | — | Immiscible | Immiscible |
| 39 | C$_9$(bpy)$_2$-PF$_6$ | 670.62 | — | — | 249 | — | Immiscible | Immiscible |

[a]Patents pending
[b]Difficulty arises in determining the melting points of some ionic liquids as they prefer the glass-state. Therefore, for some ionic liquids in which the exact melting point/glass transition temperature could not be easily determined, a temperature range is provided. A detailed discussion related to the polymorphic nature of many of these ionic liquids is provided in the section titled "*Crystal Structures of Geminal Dicationic Ionic Liquids*"
[c]This ionic liquid exhibited physico-chemical properties very similar to the 1-butyl-3-methylimidazolium chloride ionic liquid making it difficult to fully characterize.

TABLE 3

Imidazolium-based Dicationic Ionic Liquids

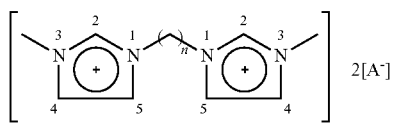

A = Br$^-$, NTf$_2^-$, BF$_4^-$, PF$_6^-$ n = 3, C$_3$(mim)$_2$-A
n = 6, C$_6$(mim)$_2$-A
n = 9, C$_9$(mim)$_2$-A
n = 12, C$_{12}$(mim)$_2$-A

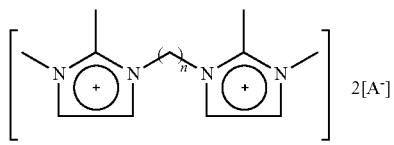

A = Br$^-$, NTf$_2^-$, BF$_4^-$, PF$_6^-$ n = 3, C$_3$(m$_2$im)$_2$-A
n = 9, C$_9$(m$_2$im)$_2$-A

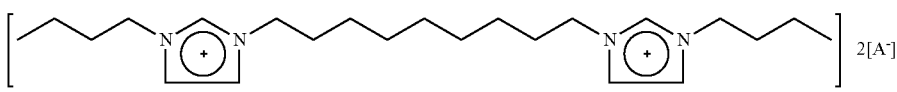

A = Br$^-$, NTf$_2^-$, BF$_4^-$, PF$_6^-$
C$_9$(bim)$_2$-A

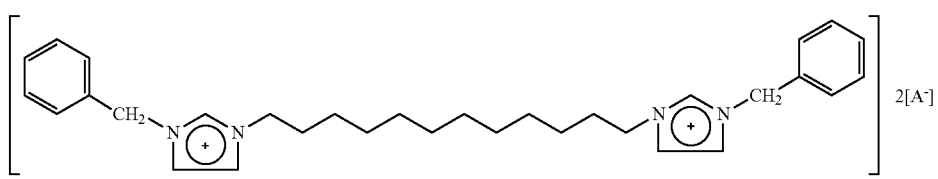

A = Br$^-$, NTf$_2^-$, PF$_6^-$
C$_{12}$(benzim)$_2$-A

Pyrrolidinium-based Dicationic Ionic Liquids

TABLE 3-continued
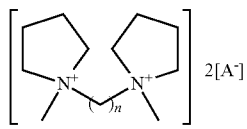
A = Br⁻, NTf₂⁻, PF₆⁻
n = 3, C₃(mpy)₂-A
n = 9, C₉(mpy)₂-A
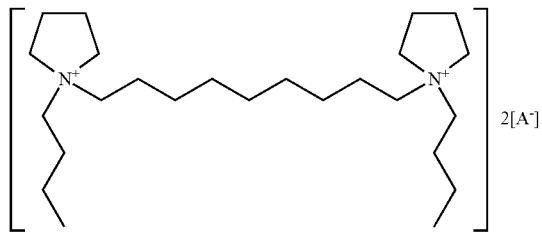
A = Br⁻, NTf₂⁻, PF₆⁻
C₉(bpy)₂-A
Also produced in accordance with the invention are:
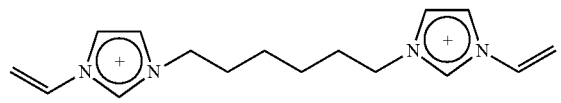
2NTf₂⁻
C₆(vim)₂-NTf₂
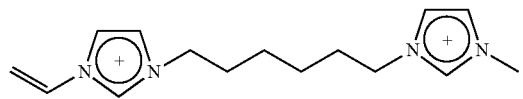
2NTf₂⁻
C₆vm(im)₂-NTf₂
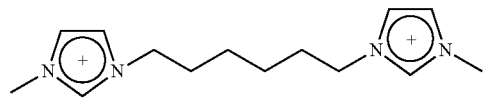
2NTf₂⁻
C₆(mim)₂-NTf₂
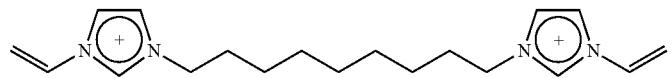
2NTf₂⁻
C₉(vim)₂-NTf₂
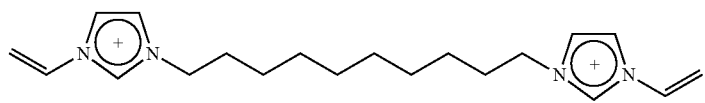
2NTf₂⁻
C₁₀(vim)₂-NTf₂*
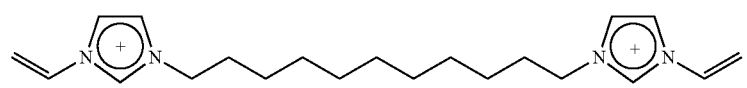
2NTf₂⁻
C₁₁(vim)₂-NTf₂

TABLE 3-continued

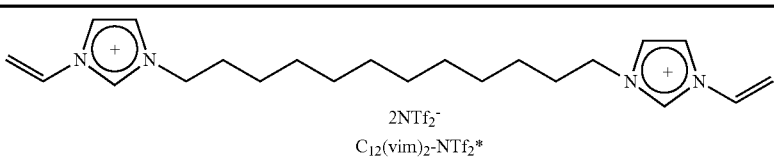

2NTf$_2^-$
C$_{12}$(vim)$_2$-NTf$_2$*

Examples of chiral ionic liquids include the following:
Chiral dicationic IL

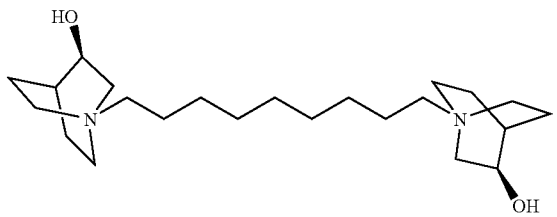

Chiral dianionic IL

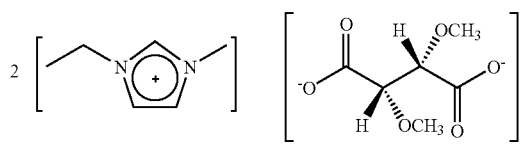

Polymerizable chiral IL

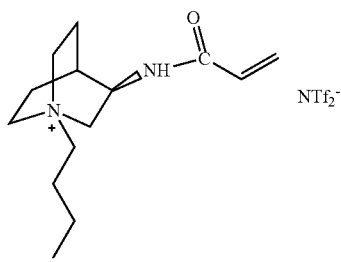

NTf$_2^-$

Polymerizable dicationic IL

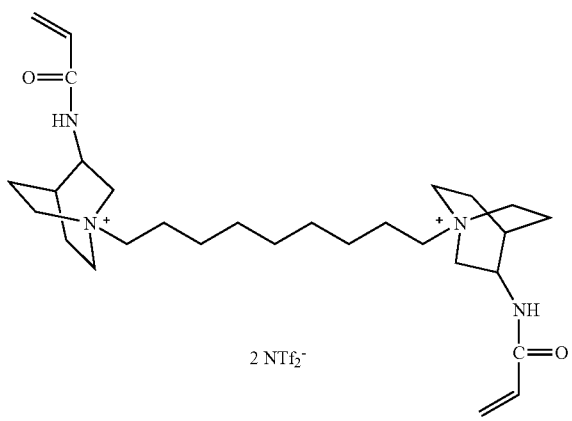

2 NTf$_2^-$

Note that some of the salts reflected in Tables 1 and 2 may not reflect the correct number of anions; usually 2 (see Table 3). Note that the names of the compounds found in Tables 1 and 2 are found in Table F. Compounds 1, 5, 9, and 13 were synthesized by reacting one molar equivalent of 1,3-dibromopropane; 1,6-dibromohexane; 1,9-dibromononane; and 1,12-dibromododecane, respectively, with two molar equivalents of 1-methylimidazole at room temperature. Compound 17 was synthesized by reacting one molar equivalent of 1,9-dibromononane with two molar equivalents of 1-butylimidazole at room temperature. Compounds 21 and 24 were synthesized by refluxing one molar equivalent of 1,3-dibromopropane and 1,9-dibromononane, respectively, with 1,2-dimethylimidazole dissolved in 125 mL 2-propanol for 24 hours. Compound 28 was synthesized by refluxing one molar equivalent of 1,12-dibromododecane with two molar equivalents of 1-benzylimidazole in 100 mL of 2-propanol for 24 hours. Following complete reaction (as monitored by NMR), the products were all purified by extraction with ethyl acetate and dried under a $P_2O_5$ vacuum.

Compounds 31 and 34 were produced by refluxing one molar equivalent amount of 1,3-dibromopropane and 1,9-dibromononane with two equivalents of 1-methylpyrrolidine in 100 mL of 2-propanol for 24 hours. Compound 37 was synthesized by refluxing two molar equivalents of 1-butylpyrrolidine with one equivalent of 1,9-dibromononane in 100 mL of 2-propanol for 24 hours. These salts were also extracted with ethyl acetate and dried under vacuum. All metathesis reactions involving N-lithiotrifluoromethylsulfonimide, hexafluorophosphoric acid, and sodium tetrafluoroborate were performed using previously published procedures. Ionic liquids formed via metathesis reactions were tested with silver nitrate to ensure no halide impurities remained.

All thirty-nine ionic liquid samples were characterized using $^1H$ NMR and electrospray ionization (ESI) mass spectrometry. $^1H$ NMR spectra (400 MHz) were recorded in deuterated DMSO.

Surface tension values were measured at room temperature (23° C.) using a Model 20 DuNuoy Tensiometer (Fisher Scientific, Fair Lawn, N.J.) equipped with a platinum-iridium ring with a mean circumference of 5.940 cm and a ring/wire radius of 53.21. The densities of the ionic liquids or, more correctly, the temperature of solid/liquid transformation (used synonymously except as indicated otherwise explicitly or by context) were determined at 23° C. by placing 2.0 mL of the ionic liquid in a 2.0 mL volumetric tube and weighing by difference. The melting points of the ionic liquids were determined using a Perkin Elmer Pyris 1 Differential Scanning Calorimeter (Boston, Mass.). Typical methods involved using a 10° C./min temperature ramp to determine and identify the first and second order thermal transitions. Melting points could not be easily determined for all compounds. For solid compounds, the melting points were verified using a capillary melting point apparatus. Refractive index measurements were conducted at 23° C. using a Bausch & Lomb Abbe-3L refractometer.

The preparation of the capillary columns for inverse gas-liquid chromatographic analysis was performed using a previously described procedure.[31] All capillary columns had efficiencies between 2100 to 2500 plates/meter. Characterization of the capillary columns and probe molecule descriptions are listed in supplemental information. Multiple linear regression analysis (MLRA) and statistical calculations were performed using the program Analyse-it (Microsoft, USA).

Tables 1, 2, and 3 give the structures of the two classes (39 compounds) of geminal dicationic ionic liquids synthesized and characterized. Ionic liquids containing imidazolium-based dications with different alkyl linkage chain lengths connecting the cations and/or different alkyl substituents on the imidazolium moiety comprise one group of ionic liquids. In most cases, each geminal dicationic entity was paired with four different anions ($Br^-$, $NTf_2^-$, $BF_4^-$, and $PF_6^-$, Table 3). Pyrrolidinium-based geminal dications with different alkyl linkage chain lengths connecting the cationic and/or different alkyl substituents on the pyrrolidinium group are also shown in Table 3. For each dication in this class, separate ionic liquids containing three anions ($Br^-$, $NTf_2^-$, and $PF_6^-$) were synthesized. Tables 1 and 2 give the physicochemical properties for these thirty-nine geminal ionic liquids. Surface tension, density, melting point, and refractive index values were recorded for those samples that were liquids at room temperature. For samples that were solids at room temperature, only the melting point was determined. The miscibility/solubility of all ionic liquids in both heptane and water are indicated as well.

Surface Tension. Plots of surface tension data are shown in FIG. 1 for several geminal room temperature ionic liquids. The length of the alkyl linkage chain separating the dications is observed to have only small effects on the surface tension. Considering ILs 2, 6, 10, and 14 (Tables 1, 2, and/or 3) which all contain the bis(trifluoromethylsulfonyl)imide ($NTf_2^-$) anion and 3-methylimidazolium cations separated by 3, 6, 9 and 12 carbon linkage chains, respectively, it is apparent that increasing the length of the connecting linkage chain slightly decreases the surface tension (~2.4 dynes/cm). A similar trend is observed for the ionic liquids containing other anions (e.g. $BF_4^-$, $Br^-$, $PF_6^-$). These results are quite different from those obtained for monocationic ionic liquids by Law, et. al.[34] It was reported that the surface tension for a series of 1-alkyl-3-methylimidazolium-based ionic liquids containing 4, 8, and 12 carbon alkyl groups in the one position of the imidazole ring (refer to Table 3 for the ring numbering of the imidazolium cation) significantly decreased with increasing alkyl chain length.[34] The largest decrease in surface tension was observed between 1-butyl-3-methylimidazolium hexafluorophosphate and 1-dodecyl-3-methylimidazolium hexafluorophosphate in which the total decrease in surface tension was nearly 20 dynes/cm at 330 K. It was also proposed that for a fixed cation at a specific temperature, the compound with the larger anion would possess a higher surface tension. However, our data indicates that this is not true for the geminal dicationic ionic liquids, and if anything, is opposite to what was observed previously for the monocationic-type ionic liquids (Tables 1 and 2).

Diionic liquids 17-20 contain nonpolar butyl groups in the three position of the imidazolium rings. The surface tension values are significantly smaller (11%-17%) than those of diionic liquids 9-12 and 13-16 which contain the 3-methylimidazolium dications separated by a nonane and dodecane linkage chain, respectively. This data seems to indicate that the alkyl substituent located on the three position of the imidazolium ring plays a more important role in lowering the surface tension than the alkyl linkage chain that separates the geminal dications.

Replacing hydrogen with a methyl group on the two position of the imidazolium ring (refer to Tables 1, 2, and 3) has little effect on the surface tension. In the case of diionic liquids 25 and 26 containing the 2,3-dimethylimidazolium geminal dications separated by a nonane linkage chain with $NTf_2^-$ and $BF_2^-$ anions, respectively, the surface tension values are similar to the corresponding 3-methylimidazolium dications (diionic liquids 10 and 11) also containing the nonane connecting chain. Overall, this data indicates that as the alkyl chain in the 3-position of the imidazolium ring increases in length, the surface tension decreases much more drastically than corresponding increases in the length of the connecting linkage chain.

Figure 2:
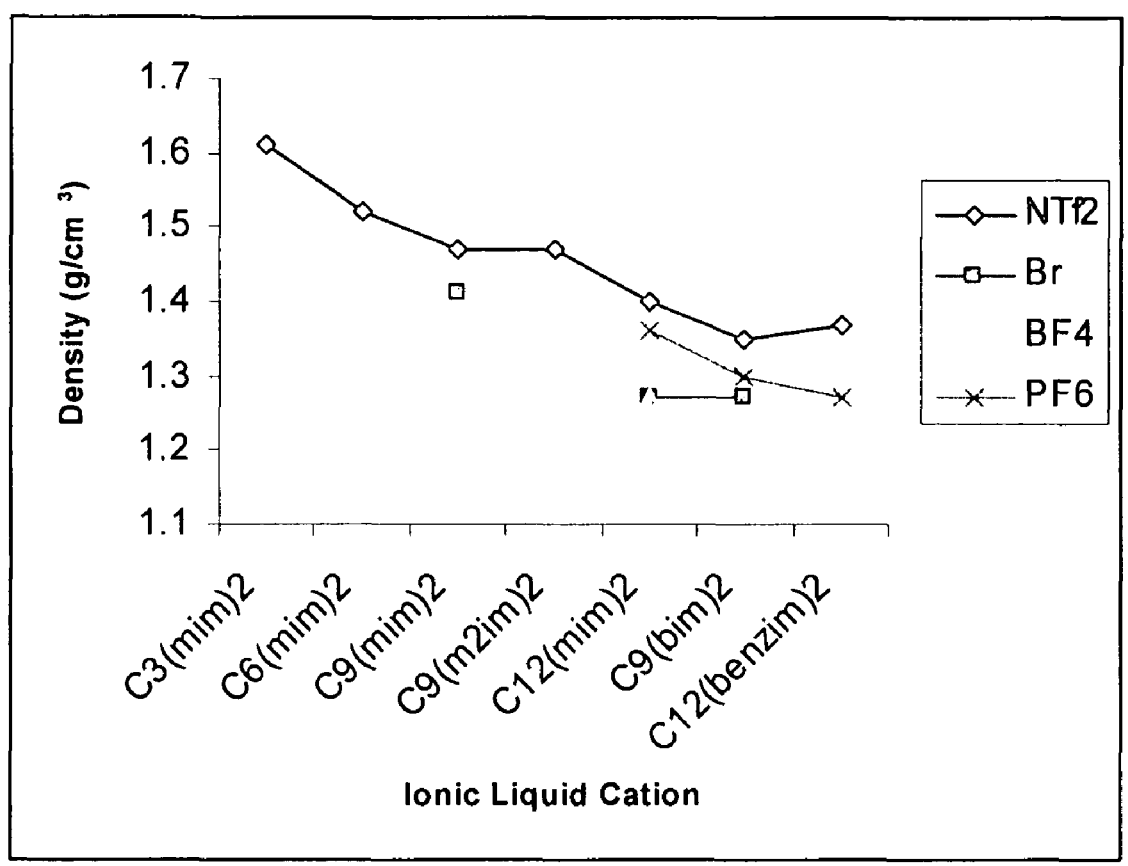
FIG. 2 illustrates the effect of the cation and anion on the density for dicationic ionic liquids.

Density. As shown in FIG. 2, the densities of the 3-methylimidazolium geminal dicationic ionic liquids were found to be anion dependent and to decrease with increasing length of the hydrocarbon linkage chain. While increases in the linkage chain decreases the density of these ionic liquids, the nature of the anion has a greater influence, with densities in the order of $NTf_2^{31}$ >$PF_6^-$>$Br$>$BF_4$ (Tables 1, 2, and FIG. 2). The decrease in density with increasing alkyl chain length has been reported previously for a large series of 1-alkyl-3-methylimidazolium ionic liquids.[26-27]

When the methyl group on the three position of the imidazolium ring is replaced with a butyl group, the density decreases for all ionic liquids in the series, regardless of the anion (compare 9-12 to 17-20, Table 1). However, by replacing the hydrogen at the two position of the ring with a methyl group, the density does not appear to change (see 10-11 and 25-26, Table 1).

Melting Points. From this study, four main factors were found to affect the melting points of these geminal-dicationic ionic liquids. These factors which apply to dianions as well are: (1) the length and type of the linkage chain or bridge separating the geminal diions, (2) the nature of the diions (e.g., imidazolium versus pyrrolidinium), (3) the substituents and their placement on the dianions, and (4) the nature of the counterion.

Considering first the 3-methylimidazolium-based dicationic ionic liquids, longer bridging groups generally result in a lowering of the melting points. This observation applies to diionic liquids generally. In all of the above-noted cases except for the geminal dications with $NTf_2^-$ anions, which were all liquids regardless of the linkage chain used, compounds containing three and six carbon linkage chains were salts with relatively high melting points. By connecting the 3-methylimidazolium dications with a nonane linkage chain, all samples were room temperature ionic liquids except for the hexafluorophosphate salt, which had a melting point of 88° C. When the dications were connected by a dodecane linkage chain, however, all compounds were room temperature ionic liquids. Looking more generally at the dianions and dications that can be used to make diionic liquids in accordance with the present invention, the chain length between the ionic species should be longer than the length of a 2 carbon chain, and no longer than a 40 carbon chain. Preferably, chain lengths are equivalent to the length of a 3 to 30 carbon chain. The degree and types of substituents, if any, may have an effect on length as well, the larger the molecule, generally, the higher its temperature of solid/liquid transformation. Therefore, any chain length, any chain content and any chain substitution pattern may be used, as long as the melting point of the resulting diionic liquid salt is less than about 400° C., preferably about 100° C. or less, preferably about 60° C., more preferably about room temperature or less (25° C.).

In addition to the effect of the different length and types of bridges connecting the dications, the anion also played a role in determining the melting point. In nearly very case of the imidazolium dications, the melting points increased in the following order: $NTf_2^-<BF_4^-<PF_6^-<Br^-$ (Tables 1 and 2).

Other anions which can be used to form dicationic ionic liquids include, without limitation, triflates, carboxylates, sulfonates and sulfates (both mono- and poly-anionic species). Dianionic ionic liquids can be produced from any dianion which can form a stable salt, preferably which has a melting point below 400° C., more preferably at or below 100° C., most preferably at or below room temperature (25° C.). These include dicarboxylate, disulfonate and disulfates. Mixed dianions, one made from, for example, a dicarboxylate and a disulfate, are also desirable. Cations or counterions for these include, again without limitation, the dications listed in Tables 1 and 2, as well as their monocationic counterparts. This is as long as they can form a stable diionic salt and have a melting point as described above.

The substituents and their position on the imidazolium ring also affected the melting points of these compounds. These same considerations apply to substituted anions as well. Considering 17-20 which contain the 3-butylimidazolium dications connected by a nonane linkage chain, the melting points were lowered significantly by replacing the methyl group (see 9-12) with a butyl group. In the case of 12, which consists of the 3-methylimidazolium dications connected by a nonane linkage chain with the $PF_6^-$ anion, the melting point is decreased by nearly 60° C. by replacing the methyl groups with butyl groups to form 20. In addition, methylation of the 2-positions of the imidazolium dications significantly increases the melting point of these compounds (see 21-27, Table 1). In the case of 21 which contains the 2,3-dimethyimidazolium dication connected by a propane linkage chain, the melting point is nearly 135° C. higher than the corresponding 3-methylimidazolium dication also connected by a propane linkage chain (1). Ngo et al. have previously reported the melting points for 1-ethyl-3-methylimidazolium bromide to be 79° C. whereas the melting point for 1-ethyl-2,3-dimethylimidazolium bromide was found to be 141° C., a difference of nearly 62° C.[35] While the methyl group on the two position of the imidazolium ring has little effect on the surface tension and density of the geminal dicationic ionic liquids, it is seen to have a profound effect on their melting points, more so for the dicationic ionic liquids than for the traditional 1-alkyl-3-methylimidazolium ionic liquids.

Finally, by replacing the 3-methylimidazolium dication with the 3-benzylimidazolium dication (28-30) and connecting them by a dodecane bridge, the melting points appear higher compared to the 3-methylimidazolium series, especially in the case of the bromide salt.

In general, the melting points of the pyrroldinium-based geminal dicationic compounds are significantly higher than their corresponding imidazolium analogues. Indeed, only two of their $NTf_2^-$ salts can be considered ionic liquids. However, as will be discussed (vide infra), these particular RTILs may have the greatest thermal stability and other highly useful and interesting properties.

The melting points for the pyrrolidinium-based dications show similar trends to the imidazolium-based salts. In the two cases involving the propane and nonane linkage chains, the melting point decreases as the linkage chain becomes longer. However, in contrast to the imidazolium-based dications, the pyrrolidinium-based dications are still relatively high melting solids when separated by a nonane alkyl chain. Additionally, substituting a butyl group instead of a methyl group on the quaternary amine of the pyrrolidinium cation causes a decrease in the melting point for the bromide dication but an increase in the melting point for the dications containing bis(trifluoromethylsulfonyl)imide and hexafluorophosphate anions.

From the data in Tables 1 and 2, it appears that longer alkyl linkage chains and long aliphatic substituents on the quaternary amine produce either low melting salts or room temperature ionic liquids. Further, the $NTf_2^-$ salts have lower melting points than corresponding salts with other anions. The contributions of the linkage chain (bridge), and other substituents on the geminal dicationic salts, to the number of possible conformational states (and possibly crystal polymorphs) will be considered in the crystal structure section of this paper.

Solubility. The solubility behavior of all thirty-nine geminal dicationic ionic liquids in water and heptane also was explored. None of the dicationic ionic liquids were soluble in heptane. However, most of the ionic liquids containing bromide and tetrafluoroborate anions were soluble in water. Nevertheless, for the tetrafluoroborate ionic liquids, it was found that by using a long linkage chain and a more hydrophobic alkyl substituent on the three position of the imidazole ring (see compounds 15 and 19), the solubility of the salt in water decreases. In general, the solubility behavior of the geminal dicationic ionic liquids in both water and heptane was quite similar to the monocationic ionic liquids with $NTf_2^-$ and $PF_6^-$ salts being immiscible with water and Br⁻ and $BF_4^-$ salts being miscible with water. Indeed, the monoionic counterparts of the diionic liquid salts of the present invention are a good predicator of the solubility of a diionic liquid salt.

In the case of the dicationic ionic liquid 28 which consists of the 3-benzylimidazolium dication separated by a dodecane linkage chain and bromide anion, the hydrophobicity of the dication evidently overrides the coordinating nature of the bromide anion to make this particular ionic liquid insoluble in water. This is a good example that the properties of the individual cations and anions can be balanced and changed in order to produce ionic liquids (or solids) with the desired properties and characteristics.

Thermal Stability. The thermal stabilities of the geminal dicationic ionic liquids were found to be significantly higher than what has been observed for many traditional imidazolium-based ionic liquids. Thermal stabilities were measured by immobilizing an approximate 0.15-0.20 microns film of the ionic liquid on the inner wall of a fused silica capillary. The capillary was then heated slowly in an oven and a very sensitive flame ionization detector (or mass spectrometer) used to detect any volatilization or decomposition of the ionic liquid. There are several advantages of using this set-up to measure the thermal stabilities of ionic liquids. The thermal stability is measured in the absence of oxygen by purging the capillary with a continuous flow of an inert gas such as helium, hydrogen, or nitrogen. In addition, the detection limit of the detector is very low (~10 ppm to 10 ppb, depending on the compound) allowing for very sensitive detection of any thermally induced decomposition/volatilization products from the ionic liquid. Finally, this approach can use mass spectrometry detection to determine the likely volatilization/decomposition products.

Figure 3:
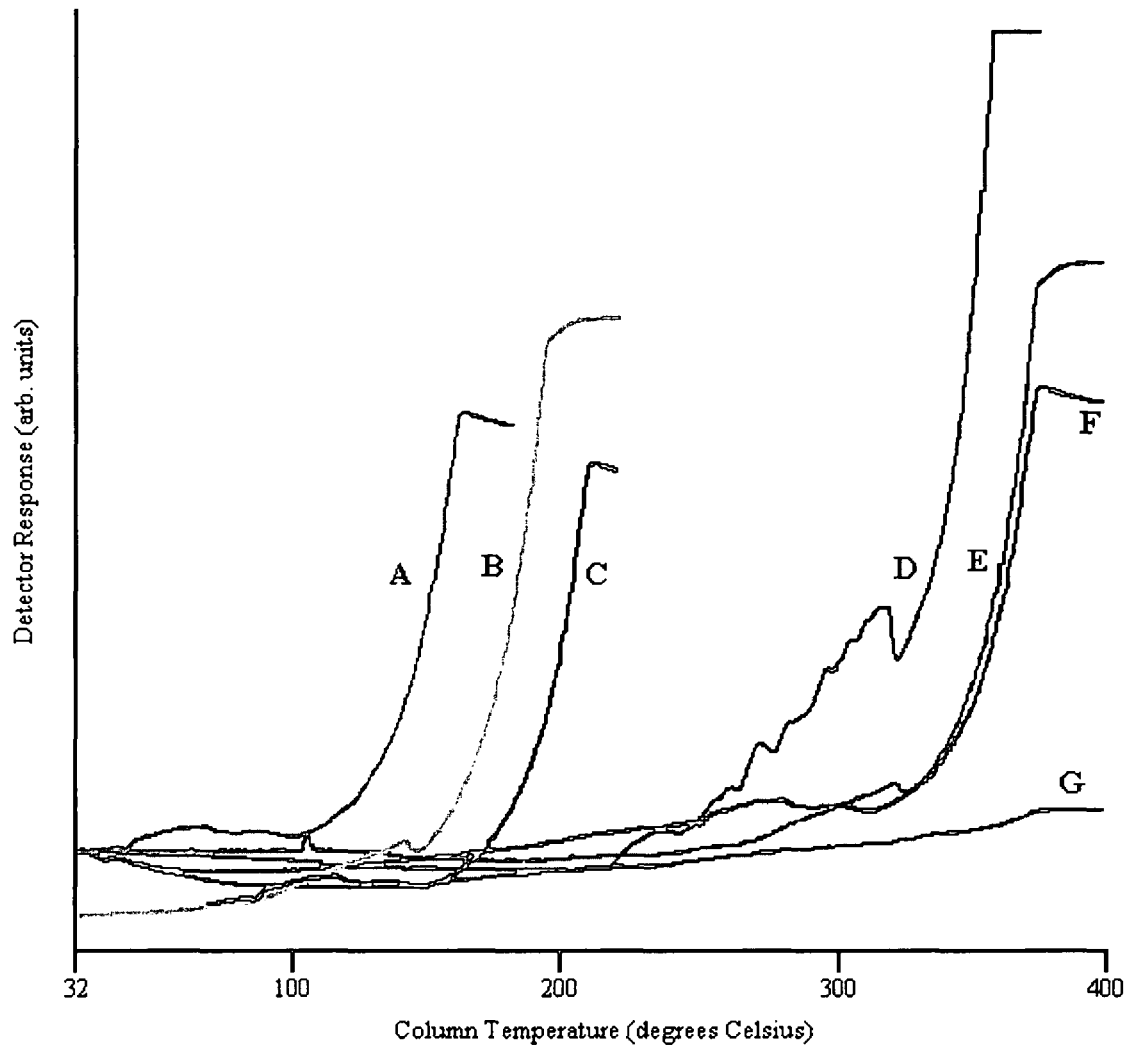
FIG. 3 is a thermal stability diagram showing the decomposition/volatilization of thin films coated on the walls of fused silica capillaries, heated under a constant flow of helium, using an ultra-sensitive flame ionization detector. The plot illustrates the fact that the geminal dicationic ionic liquids (D-G) have much higher thermal stabilities, and/or lower volatilities, than conventional ionic liquids (A-C). A, 1-butyl-3-methylimidazolium chloride (BMIM-Cl); B, BMIM-PF$_6$; C, BMIM-NTf$_2$; D, C$_9$(bpy)$_2$-NTf$_2$, 38; E, C$_9$(mim)$_2$-NTf$_2$, 10; F, C$_{12}$(benzim)$_2$-NTf$_2$, 29; G, C$_9$(mpy)$_2$-NTf$_2$, 35.

FIG. 3 shows a thermal stability diagram containing three traditional ionic liquids and four dicationic ionic liquids. The traditional ionic liquids have thermal stabilities ranging from 145° C. (1-butyl-3-methylimidazolium chloride) to 185° C. (1-butyl-3-methylimidazolium bis(trifluoromethylsulfonyl) imide). However, the thermal stabilities of the geminal dicationic ionic liquids are observed to range from 330° C. to 400° C., depending on the cation used. The highest thermal stability (>400° C.) was obtained with the $C_9(mpy)_2$-$NTf_2$ (35) ionic liquid (1-methylpyrrolidinium dication separated by a nonane linkage chain) while the lowest volatilization/decomposition temperature (330° C.) was observed for the $C_9$(bpy)$_2$-$NTf_2$ (38, 1-butylpyrrolidinium dication separated by a nonane linkage chain) ionic liquid. The maximum thermal stabilities of $C_9$(mim)$_2$-$NTf_2$ (10, 1-methylimidazolium dication) and $C_{12}$(benzim)$_2$-$NTf_2$ (29, 3-benzylimidazolium dication separated by a dodecane linkage chain) were observed to be nearly identical (350-360° C.). In most cases, slight to moderate decomposition/volatilization of the dicationic ionic liquids were observed at these high temperatures. However, due to charring of the polyimide coating on the outside of the fused silica capillary tubing at these high temperatures, the ionic liquids were only tested up to 400° C.

While the physical and thermal properties of the dicationic ionic liquids are quite impressive, another interesting fact is that some of these compounds possess useful liquid ranges in excess of 400° C. and one of these ($C_9$(mpy)$_2$-$NTf_2$) 35 has a stable liquid range of ~−4° C. to >400° C. This property will undoubtedly ensure their use for a wide variety of applications in which this large liquid range and high thermal stability can be exploited. In accordance with one aspect of the present invention, the ionic liquids of the present invention, which are salts of a dianion or dication, are stable. Stability in the context of the present invention means that they will neither substantially decompose nor volatilize at a temperature of under about 200° C. when measured by inverse gas chromatography as described herein. More preferably, the stable ionic liquids of the present invention which are dianionic or dicationic salts, are stable in that they will not substantially decompose or volatilize at a temperature of under about 300° C.

In FIG. 3, it is believed that the detector response shown for compounds D, E and F, between approximately 200 and approximately 300° C. are from impurities and not from the compounds tested. Still, less than 10% of the weight of the material tested decomposes or volatilizes when exposed to 200° C. or in preferred embodiments, 300° C., for an hour, they can be said to be stable in accordance with the present invention.

In particularly preferred embodiments in accordance with the present invention, dianionic or dicationic ionic liquid salts are provided, which are stable in that they will neither substantially decompose nor substantially volatilize at a temperature of under 200° C. and will have a temperature of solid/liquid transformation of 400° C. or less. More preferably will have a temperature of solid/liquid transformation of 100° C. or less, most preferably will have a temperature of solid/liquid transformation of 25° C. or less.

As mentioned previously, the diionic liquids (salts of dianions and dications as described herein) have an important use because of their stability at wide ranges of temperature and unique liquid properties. Many of these liquids have unexpectedly low temperatures of solid-liquid transformation, which from a fundamental standpoint depends upon the energy of their crystal lattice. There are well-known and rather crucial barriers to precisely calculating these energies, i.e., the true determination of atom-atom potentials. On the other hand, the accurate measurement (required for comparison) of solid-liquid transformation temperatures for this family of ionic compounds also have difficulties. The transformation is not sharp in time and the peaks on DSC curves become very broad. Formally speaking, the temperature of this transformation can be very different from the true melting point which is the temperature of thermodynamic equilibrium between solid and liquid states.

Solvation Characteristics We have previously reported that the Abraham solvation model, a linear free energy approach that utilizes inverse gas-liquid chromatography to describe the solvation properties of a liquid, can be used to characterize room temperature ionic liquids.[31] Described by equation 1, the model provides the so-called "interaction parameters" (r, s, a, b, l) by using multiple linear regression analysis to fit the retention factor (k, determined chromatographically) to the solute descriptors ($R_2$, $\pi_2^H$, $\alpha_2^H$, $\beta_2^H$, log $L^{16}$) for a wide variety of probe solute molecules.

$$\log k = c + rR_2 + s\pi_2^H + b\beta_2^H + l \log L^{16} \quad [1]$$

The solvation properties of four dicationic ionic liquids (see Table 4) were evaluated and the interaction parameters compared to those obtained for their traditional monocationic analogues 1-butyl-3-methylimidazolium and 1-butyl-1-methylpyrrolidinium ionic liquids.

TABLE 4

Comparison of interaction parameters between monocationic and dicationic ionic liquids.

| Temp (° C.) $C_4(mim)_2$-$NTf_2$ | c | r | s | a | b | l | n | $R^2$ | F |
|---|---|---|---|---|---|---|---|---|---|
| 40 | −2.94 | 0.25 | 2.01 | 2.11 | 0.50 | 0.56 | 33 | 0.99 | 356.70 |
|  | (0.13) | (0.09) | (0.12) | (0.11) | (0.13) | (0.03) |  | (0.11) |  |
| 70 | −2.91 | 0.22 | 1.78 | 1.77 | 0.45 | 0.44 | 32 | 0.99 | 370.42 |
|  | (0.11) | (0.10) | (0.11) | (0.09) | (0.14) | (0.03) |  | (0.09) |  |
| 100 | −3.06 | 0.20 | 1.69 | 1.57 | 0.33 | 0.37 | 31 | 0.98 | 253.79 |
|  | (0.13) | (0.09) | (0.10) | (0.08) | (0.13) | (0.03) |  | (0.09) |  |
| $C_9(mim)_2$-$NTf_2$ (10) | | | | | | | | | |
| 40 | −2.86 | 0.16 | 1.81 | 1.83 | 0.47 | 0.62 | 32 | 0.98 | 257.15 |
|  | (0.14) | (0.11) | (0.14) | (0.10) | (0.17) | (0.04) |  | (0.12) |  |
| 70 | −2.95 | 0.11 | 1.76 | 1.75 | 0.20 | 0.51 | 33 | 0.99 | 644.20 |
|  | (0.09) | (0.07) | (0.08) | (0.07) | (0.10) | (0.02) |  | (0.07) |  |
| 100 | −3.06 | 0.11 | 1.64 | 1.50 | 0.15 | 0.43 | 32 | 0.99 | 545.32 |
|  | (0.08) | (0.06) | (0.07) | (0.06) | (0.09) | (0.02) |  | (0.07) |  |
| BMIM-$NTf_2$[a] (1-butyl-3-methylimidazolium bis[(trifluoromethylsulfonyl)imide] | | | | | | | | | |
| 40 | −2.87 | 0 | 1.89 | 2.02 | 0.36 | 0.63 | 33 | 0.99 | 459.64 |
|  | (0.10) | (0.08) | (0.10) | (0.10) | (0.12) | (0.03) |  | (0.09) |  |
| 70 | −3.03 | 0 | 1.67 | 1.75 | 0.38 | 0.56 | 35 | 0.99 | 413.65 |
|  | (0.09) | (0.08) | (0.09) | (0.09) | (0.11) | (0.02) |  | (0.09) |  |
| 100 | −3.13 | 0 | 1.60 | 1.55 | 0.24 | 0.49 | 32 | 0.98 | 240.13 |
|  | (0.12) | (0.09) | (0.10) | (0.10) | (0.12) | (0.03) |  | (0.09) |  |
| $C_9(mpy)_2$-$NTf_2$ (35) | | | | | | | | | |
| 40 | −2.83 | 0.27 | 1.71 | 1.98 | 0.32 | 0.62 | 30 | 0.99 | 377.84 |
|  | (0.12) | (0.10) | (0.12) | (0.10) | (0.15) | (0.03) |  | (0.10) |  |
| 70 | −2.85 | 0.34 | 1.52 | 1.65 | 0.35 | 0.48 | 32 | 0.99 | 419.32 |
|  | (0.11) | (0.09) | (0.11) | (0.08) | (0.13) | (0.03) |  | (0.09) |  |
| 100 | −2.99 | 0.23 | 1.49 | 1.48 | 0.15 | 0.42 | 30 | 0.99 | 339.79 |
|  | (0.10) | (0.09) | (0.10) | (0.08) | (0.14) | (0.03) |  | (0.08) |  |
| BMPY-$NTf_2$[b] (1-butyl-1-methylpyrrolidinium bis[(trifluoromethylsulfonyl)imide] | | | | | | | | | |
| 40 | −2.78 | 0 | 1.69 | 2.08 | 0.16 | 0.68 | 34 | 0.98 | 321.99 |
|  | (0.11) | (0.09) | (0.11) | (0.12) | (0.14) | (0.03) |  | (0.11) |  |
| 70 | −2.80 | 0 | 1.53 | 1.78 | 0 | 0.56 | 34 | 0.99 | 393.23 |
|  | (0.10) | (0.08) | (0.09) | (0.08) | (0.11) | (0.02) |  | (0.09) |  |
| 100 | −2.92 | 0 | 1.44 | 1.55 | 0 | 0.48 | 32 | 0.99 | 358.08 |
|  | (0.09) | (0.07) | (0.08) | (0.07) | (0.09) | (0.02) |  | (0.08) |  |
| $C_{12}(benzim)_2$-$NTf_2$ (29) | | | | | | | | | |
| 40 | −2.94 | 0.11 | 1.65 | 1.96 | 0.84 | 0.66 | 33 | 0.99 | 522.89 |
|  | (0.11) | (0.08) | (0.11) | (0.08) | (0.13) | (0.03) |  | (0.08) |  |
| 70 | −3.07 | 0.07 | 1.62 | 1.75 | 0.57 | 0.56 | 30 | 0.99 | 888.94 |
|  | (0.08) | (0.05) | (0.08) | (0.06) | (0.09) | (0.02) |  | (0.06) |  |
| 100 | −3.12 | 0 | 1.47 | 1.44 | 0.52 | 0.46 | 30 | 0.99 | 478.94 |
|  | (0.09) |  | (0.09) | (0.06) | (0.10) | (0.02) |  | (0.07) |  |

[a] r = interaction via nonbonding and □-electrons, s = dipolarity/polarizability, a = hydrogen bond basicity, b = hydrogen bond acidity, l = dispersion forces, n = number of probe molecules subjected to multiple linear regression analysis, $R^2$ = statistical correlation coefficient, F = Fisher coefficient. Values in parenthesis are the standard deviations for each interaction parameter.
[b] Values taken from reference 31

Nearly all interaction parameters of the dicationic ionic liquids $C_4(mim)_2$-$NTf_2$ and $C_9(mim)_2$-$NTf_2$ (10) are similar to the corresponding monomer-type ionic liquids, 1-butyl-3-methylimidazolium bis(trifluoromethylsulfonyl)imide. This is also observed for the pyrrolidinium dication, $C_9(mpy)_2$-$NTf_2$ (35), as it differs from the monomer-type analogue (1-butyl-1-methylpyrrolidinium bis(trifluoromethylsulfonyl)imide). This indicates that the well-known and highly useful solvation properties of traditional RTILs are very similar to those of the geminal dicationic RTILs. The only interaction parameter that is statistically different between the three ionic liquids is the "r" interaction parameter, namely the ability of the ionic liquid to undergo π-π and n-π interactions with probe solute molecules. Because the pyrroldinium cation is not aromatic, the higher r values may be due to the anion as each anion contains two sulfone groups that are capable of undergoing such interactions. However, this was not observed for the traditional ionic liquids evaluated previously in our study.[31]

Finally, the interaction parameters for the 3-benzylimidazolium geminal dication separated by a dodecane linkage chain with the $NTf_2^-$ anion (29) appear similar to those observed previously for 1-benzyl-3-alkyl-imidazolium ionic liquids. However, the hydrogen bond acidity term, b, is larger for the geminal dicationic ionic liquid. This may be due to the increased acidity of the proton at the 2-position of the imidazolium ring induced by the electron withdrawing benzyl group.[4]

As noted earlier, the viscosity of some diionic salts decreases sharply with increasing temperature. Consequently at high temperatures, previously uniform coated capillaries, particularly ones that are prepared by adsorption or absorption, rather than immobilization, can experience film disruption (due to flow, etc.). When a uniformly coated GC capillary, for example, slowly changes to a nonuniformly coated entity, the analyte retention times and efficiency tend to decrease.

To overcome these issues, where necessary, and in accordance with another aspect of the present invention, there is provided a process which includes the free radical reaction of ionic liquid monomers to provide a more durable and robust stationary phase, as well as the cross-linked and/or immobilized stationary phases and the columns that include same. By partially crosslinking the ionic liquid stationary phase using a small percentage of free radical initiator, high efficiency capillary columns are produced that are able to endure high temperatures with little column bleed. It was found that low to moderate temperature separations (30° C.-280° C.) can be carried out with high selectivity and efficiency using special partially cross-linked ionic liquid stationary phase mixtures. These stationary phases retain their "gelatinous," "semi liquid," amorphous state. For separations conducted at higher temperatures (300° C.-400° C.), more highly cross-linked/immobilized stationary phases are well-suited to provide high selectivity and efficient separations with low column bleed. The effect of different functionalized ionic liquid salt mixtures and initiator concentrations is studied for these two types of stationary phases. The accomplished goal is to maximize their separation efficiency, thermal stability, and column lifetime, without sacrificing the unique selectivity of the stationary phase.

The following materials were used to illustrate the unique advantages of cross-linked stationary phases comprising diionic liquid salts in accordance with the present invention: 1-vinylimidazole, 1-bromohexane, 1-bromononane, 1-bromododecane, 1,9-dibromononane, 1,12-dibromododecane, 1-bromo-6-chlorohexane, 1-methylimidazole, N-Lithiotrifluoromethanesulfonimide, 2,2'-Azobisisobutyronitrile (AIBN), dichloromethane, ethyl acetate, and all test solutes were purchased from Aldrich (Milwaukee, Wis.). Untreated fused silica capillary tubing (0.25-mm inner diameter) and a fatty acid methyl ester (FAME) kit containing 19 standards was purchased from Supelco (Bellafonte, Pa.). Structures and physico-chemical properties of the monocation monomers and the dication crosslinkers used are shown in Table A. Monomers 1, 2, and 3 were synthesized by reacting one molar equivalent of 1-vinylimidazole with a slight molar excess of 1-bromohexane, 1-bromononane, and 1-bromododecane, respectively. These reactions were performed at room temperature in round bottom flasks lined with aluminum foil to prevent thermal/photo-induced polymerization. Care should be taken when synthesizing and purifying these compounds to minimize excess heat/light during reaction or roto-evaporation to prevent unwanted reaction of the ionic liquid. The resulting bromide salt was evaporated under vacuum to remove the excess 1-bromoalkane. Three 15 mL aliquots of ethyl acetate were used to wash the ionic liquid to remove any other impurities. After evaporating the ethyl acetate under vacuum, the bromide salt was dissolved in water and mixed with one molar equivalent of N-Lithiotrifluoromethane-sulfonimide, also dissolved in water. After stirring for 12 hours, the water was removed and the remaining ionic liquid thoroughly washed with water using three 50 mL aliquots of water. A portion of the third aliquot of water was subjected to the silver nitrate test to ensure the absence of silver bromide precipitate. The monomers were then dried under vacuum and then placed under a $P_2O_5$ vacuum in the absence of light.

Figure 4:
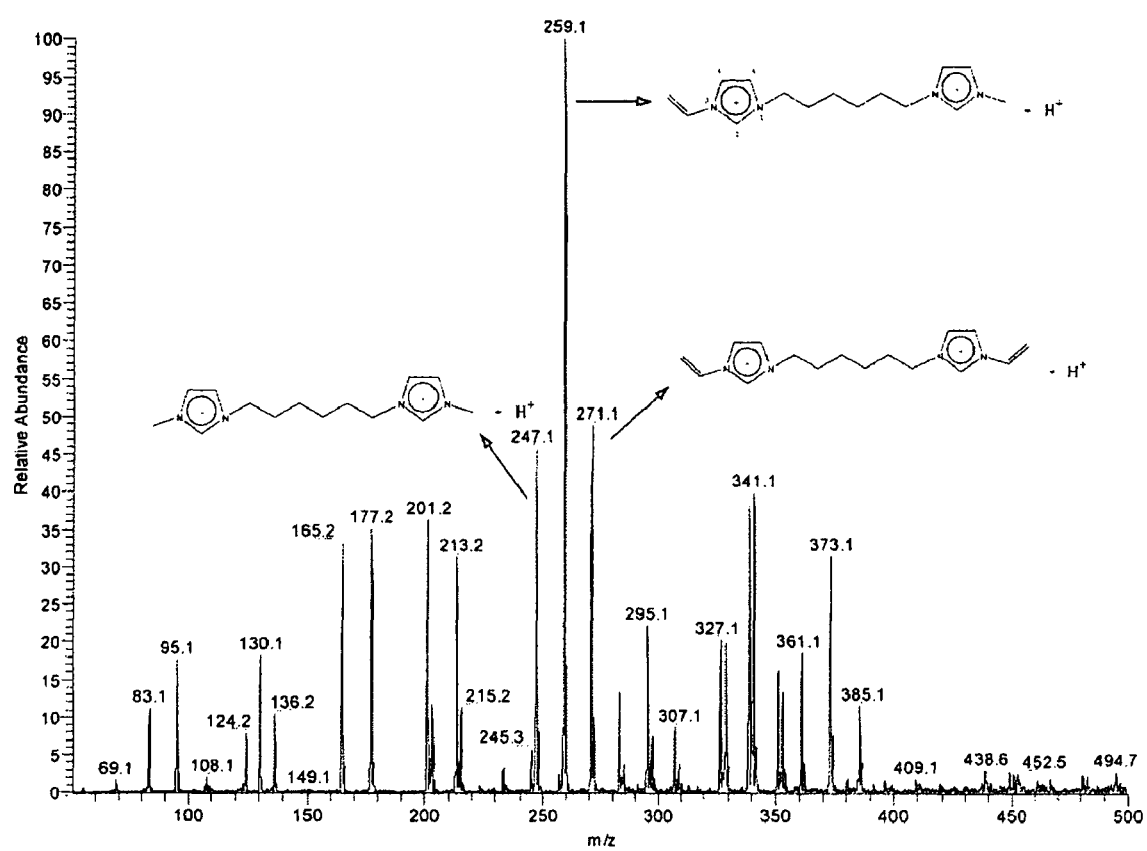
FIG. 4 is a positive ion electrospray mass spectrum of mixture 4 indicating the relative abundance of the three substituted dications as well as the loss of a proton on the imidazolium ring thereby allowing the formation of the +1 ion.

The dication crosslinkers were synthesized using a modified procedure recently reported for a series of geminal dicationic ionic liqids.[40] Compound 4 in Table A is a mixture of $C_6(vim)_2^{2+}$ (m/z=272.1), $C_6vm(im)_2^{2+}$ (m/z=260.1), and $C_6(mim)_2^{2+}$ (m/z=248.1) in a 1:2:1 molar mixture, respectively, as indicated in the electrospray mass spectrum in FIG. 4. When acquired in positive ion mode, the most dominant ions for these three structurally similar compounds appear to be the +1 ion minus a proton. Further experiments conducted in our group in which the C-2 proton on the imidazolium ring (see FIG. 4 for numbering of ring system) is deuterated indicates that this proton is lost and causes one of the positive charged aromatic rings to neutralize charge and give rise to the +1 ion (data not shown). This mixture was synthesized by reacting one molar equivalent of 1-bromo-6-chlorohexane with one molar equivalent of 1-methylimidazole in an ice bath overnight. Subsequently, one molar equivalent of 1-vinylimidazole was added dropwise over a period of 30 minutes and the temperature of the mixture increased to 55° C. for 3 hours. Three 15 mL aliquots of ethyl acetate were used to extract any excess starting material and the bromide anion was exchanged for the bis[(trifluoromethane)sulfonyl]imide ($NTf_2^-$) anion by reaction of two equivalents of N-Lithiotrifluoromethanesulfonimide dissolved in water for every one equivalent of the crosslinker salt.

In an analogous manner, the remaining crosslinkers 5, 6, 7, and 8 were prepared by reacting one molar equivalent of the dibromoalkane with two molar equivalents of 1-vinylimidazole. Compound 9 was prepared by reacting one molar equivalent of 1-methylimidazole with molar equivalent of 1-bromononane at 100° C. for 5 hours. Clean-up and metathesis exchange for the $NTf_2^-$ anion was performed as described above for the synthesis of the monomer ionic liquids.

Capillaries were coated using the static coating method at 40° C. Coating solutions of the monomer and/or crosslinker ionic liquids were prepared at concentrations of 0.20% (w/v) in dichloromethane. Prior to adding the dichloromethane to the monomer and/or crosslinker mixture, 0.7 mg of AIBN (~3.5% by weight) was added. AIBN is known to undergo decomposition to form cyanoisopropyl radicals which subsequently produce several products by dimerization, disproportionation reactions, or chain reactions.[42] The thermal decomposition kinetics of AIBN have been well studied using a variety of spectroscopic and polarographic techniques.[43] Based on an Arrhenius plot, Van Hook and co-workers have proposed a rate expression for the decomposition of AIBN in solution to be: $k_d=1.58\times10^{15} \exp(-30.8 \text{ kcal.}/RT)$.[42] For a temperature of 40° C. in which the capillaries are coated with the initiator present in the coating solution, this yields a decomposition rate constant of ~$5.07\times10^{-7}$ sec$^{-1}$. Due to the fact that this rate constant is so small and that the coating rate is relatively fast, there should be very little polymerization of the monomer/crosslinker mixture during the coating of the capillary.

After coating, the ends of the capillary were flame sealed and the capillary placed in a GC oven and heated from 40° C.-80° C. at 1° C./min. The capillary was then held at 80° C. for 5 hours to ensure complete polymerization. Helium carrier gas was then flushed through the capillary at a rate of 1 mL/min and the capillary conditioned from 30° C. to 120° C. at 3° C./min and held at 120° C. for two hours.

Solvation thermodynamics can be determined chromatographically by recognizing that the Gibbs free energy change, $\Delta G°$, of a solute between the mobile phase and the stationary phase can be described by equation 1:

$$\Delta G° = -RT \ln\left(\frac{k}{\Phi}\right) \quad [1]$$

where k is the solute retention factor and $\Phi$ is the column phase ratio. An expression shown in equation 2 can then be derived and illustrates the dependence of enthalpy, ΔH°, and entropy, ΔS°, on the change of the retention factor with temperature:

$$\ln k = -\left(\frac{\Delta H°}{R}\right)\frac{1}{T} + \left[\frac{\Delta S°}{R} + \ln \Phi\right] \quad [2]$$

A van't Hoff plot of in k versus 1/T provides the entropy (intercept) and enthalpy (slope) and describes a solute's transfer from the gas phase to the ionic liquid stationary phase. In this work, the solvation thermodynamics were determined for seven different probe molecules, listed in Table D, on two cross-linked ionic liquid phases and one ionic liquid stationary phase. As Table D illustrates, the probe molecules evaluated in this study differ in terms of size and the types of functional groups that they possess. For each probe molecule on each stationary phase, three separate van't Hoff plots were constructed so that changes in the probe molecule retention factor could be used to provide an error for each thermodynamic parameter. The probe molecule retention factors were determined at six different temperatures to obtain the highest possible correlation coefficient (>0.989).

Previously we characterized a large number of room temperature ionic liquids in terms of multiple solvation interactions using the solvation parameter model, shown in equation 3.[44]

$$\log k = c + rR_2 + s\pi_2^H + a\alpha_2^H + b\beta_2^H + l \log L^{16} \quad [3]$$

This approach utilizes inverse gas-liquid chromatography and allows the use of a large number of probe molecules to deconvolute solute retention in terms of the type and magnitude of individual solvation interactions. The solute descriptors ($R_2$, $\pi_2^H$, $\alpha_2^H$, $\beta_2^H$, $\log L^{16}$) from Equation 3 are obtained from the literature for many probe molecules containing a variety of functional groups.[45] The retention factor is determined chromatographically. The solute descriptors and retention factors are subjected to multiple linear regression analysis to obtain the interaction parameter coefficients (r, s, a, b, l), which ultimately characterize the stationary phase: r is the ability of the diionic liquid containing-stationary phase to interact with π0 and n electrons of the solute, s is a measure of the dipolarity/polarizability of the diionic liquid containing-stationary phase, a defines the diionic liquid containing-stationary phase hydrogen bond basicity, b is a measure of the hydrogen bond acidity, and l refers to the ability of the diionic liquid containing-stationary phase to separate adjacent members of a homologous series.[46]

Test solutes used to determine interaction parameters and solvation thermodynamics were dissolved in dichloromethane. A Hewlett-Packard model 5890 gas chromatograph and a Hewlett-Packard 6890 series integrator were used for all separations. Split injection and flame ionization detection were utilized with injection and detection temperatures of 250° C. Helium was used as the carrier gas with a column inlet pressure of 3.1 psi and flow rate of 1.0 mL/min. Methane was used to determine the dead volume of the column. Multiple linear regression analysis and statistical calculations were performed using the program Analyze-it (Microsoft).

Figure 5:
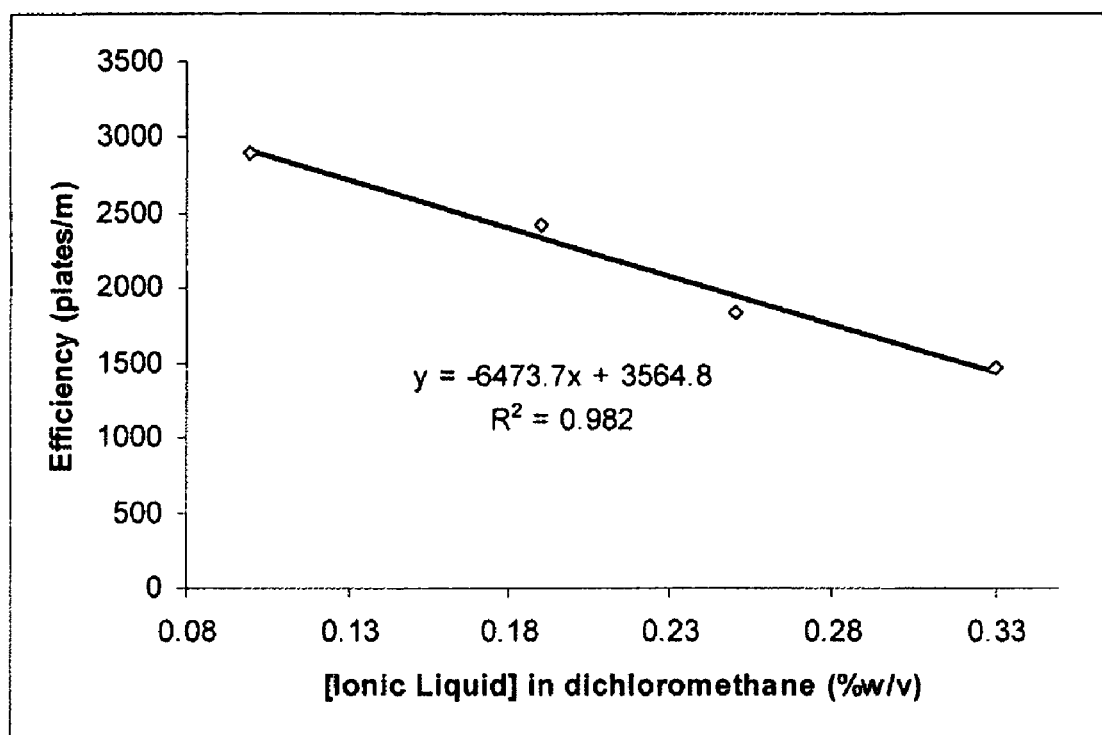
FIG. 5 is a plot illustrating the effect of 1-hexyl-3-vinylimidazolium bis[(trifluoromethane)sulfonyl]imidate film thickness on the peak efficiency (theoretical plates/meter) of naphthalene at 100° C.

Equation 4 can be used to approximate the stationary phase film thickness for gas chromatographic capillaries coated by the static coating method,[47]

$$d_f = \frac{d_c \times c}{400} \quad [4]$$

where: $d_f$ is the film thickness of the ionic liquid stationary phase in micrometers, $d_c$ is the diameter of the capillary (in micrometers), and c is the percentage by weight concentration of the stationary phase dissolved in an appropriate solvent. FIG. 5 shows the effect of 1-hexyl-3-vinylimidazolium bis[(trifluoromethane)sulfonyl]imidate film thickness on the peak efficiency of naphthalene at 100° C. As the plot clearly demonstrates, the highest efficiency separations were carried out with a film thickness of ~0.07 μm (0.10% w/v of ionic liquid in dichloromethane) while the worst efficiency separations were obtained on columns with a film thickness of ~0.21 μm (0.33% w/v). In this work, all capillaries were coated with a 0.20% (w/v) coating solution yielding a film thickness of approximately 0.125 μm.

Using the ionic liquids in Table A, a variety of free radical cross-linking experiments were carried out in chloroform following the method of Muldoon and co-workers[48] to determine which ratios of monocationic/crosslinker monomers result in copolymers that possess the ideal properties for a GC stationary phase. For example, some copolymers (i.e., formed from monomers 1 and 5) containing only a few percent by weight crosslinker resemble gum-like polysiloxane phases. However, other highly cross-linked copolymers formed hard plastics and are therefore undesirable for gas-liquid chromatographic separations.

Monocationic monomer ionic liquids 1, 2, and 3 contain the 1-vinylimidazolium cation with hexyl, nonyl, and dodecyl alkyl chains, respectively. When polymerized, these ionic liquids form linear polymer chains, as demonstrated previously by Marcilla and co-workers.[49] As illustrated in Table B, these stationary phases exhibited a range of initial separation efficiencies, ranging from 2813 plates/meter for ionic liquid 1 and ~1900 plates/meter for ionic liquid 3 when conditioned to 120° C. While it appears that the hexyl substituted vinylimidazolium cation produces a more efficient stationary phase coating, subsequent evaluation of the stationary phases using higher conditioning temperatures revealed that the efficiencies of these capillaries decrease rapidly. After conditioning up to 350° C., volatilization of the ionic liquids resulted in efficiencies that dropped to several hundred plates/meter. No retention of naphthalene was observed after conditioning the capillaries to 380° C., indicating an insufficient amount of ionic liquid remained on the capillary wall.

To produce a more thermally robust ionic liquid matrix, geminal dicationic vinylimidazolium crosslinkers with different length alkyl chains separating the dications were mixed with the monocationic monomers. These mixtures are shown in Table B under the heading "partially/fully crosslinked matrices." From our previous solution-based polymerization experiments, it was found that the concentration of crosslinker is crucial for the formation of a matrix exhibiting ideal stationary phase properties (data not shown). Compound 4 (see Table A), is a mixture of three dicationic ionic liquids separated by a six carbon linkage chain. Electrospray mass spectrometry indicated that for every one of the 1,6-di (3-methylimidazolium)hexane[$C_6(mim)_2^{2+}$] dications and 1.6-di(3-vinylimidazolium)hexane [$C_6(vim)_2^{2+}$] dications, there are two of the 1-(3-vinylimidazolium)-6-(3'-methylimidazolium)hexane [$C_6vm(im)_2^{2+}$] dications. When a column was prepared by polymerizing/immobilization only this mixture, the initial efficiency after conditioning to 120° C. was nearly 3000 plates/meter (Table B). Moreover. The efficiency dropped much less after conditioning the capillary at higher temperatures. For example, the efficiency of 4 after conditioning at 350° C. was 1365 plates/meter whereas the efficiencies of the monocationic ionic liquids without crosslinker ranged from 120 to 197 plates/meter after the same conditioning step. Clearly, by crosslinking the ionic liquids, the efficiency and thermal stability of the stationary phase is preserved at higher temperatures.

A series of different crosslinked ILs were also synthesized using various ratios of 1-vinyl-3-hexylimidazolium bis[(trifluoromethane)sulfonyl]imidate (1) and the dication mixture 4, described above. The highest efficiencies were obtained with crosslinking mixtures formed with equal percentages of the monocationic and crosslinking monomers whereas copolymers formed with a higher concentration of crosslinker exhibited lower efficiencies (see Table B). The effect of the alkyl side chain of the monocationic monomer was investigated by preparing equal molar ratios of the crosslinking mixture 4 with two other monocationic monomers, 1-vinyl-3-nonylimidazolium bis[(trifluoromethane)sulfonyl]imidate (2) and 1-vinyl-3-dodecylimidazolium bis[(trifluoromethane)sulfonyl]imidate (3). As Table B illustrates, there is very little difference between these different composition crosslinked matrices in terms of separation efficiency and loss of efficiency at high temperatures. Recall that previously it was noted that when the monocationic monomers were polymerized without crosslinker, the length of the alkyl group appeared to have an effect on the separation efficiency/thermal stability of the stationary phase at higher temperatures. This demonstrates that the length of the alkyl group on the monocationic monomer plays less of a role in the loss of separation efficiency at high temperatures when it is part of a crosslinked stationary phase.

Ionic liquid stationary phases based only on crosslinking monomers were also evaluated. As shown in Table B, one mixture was based on the crosslinking of vinylimidazolium dications separated by a nonane linkage chain (0.20% 5) while the second mixture consisted of ionic liquids 5, 6, 7, and 8, namely dicationic ionic liquid monomers separated by a nonane, decane, undecane, and dodecane linkage chain, respectively. This mixture of four crosslinkers, abbreviated as $C_{9-12}(vim)_2$-$NTf_2$ in Table 4, was made due to the fact that compounds 6 and 8 are supercooled solids at room temperature and, therefore, are not ideal monomers for creating "gummy" or "waxy" stationary phases. This mixture consists of 10.88% by weight of 5, 9.29% of 6, 19.59% of 7, and 60.24% of 8.

A couple of interesting trends were observed for the highly crosslinked ionic liquid stationary phases that were not observed for the monocationic linear or partially crosslinked materials. First, although the separation efficiency of the completely crosslinked stationary phases was low after conditioning to 380° C., the ionic liquid stationary phase was still present as a thin film in the capillary when viewed under microscope after prolonged exposure to this temperature. In contrast, only a few partially crosslinked stationary phases (see Table B) provided retention of naphthalene after high temperature conditioning. All stationary phases formed using monocationic monomers alone appeared to have decomposed and/or volatilized completely from the capillary wall after conditioning to 380° C.

The most impressive and interesting characteristic of the completely crosslinked ionic liquid stationary phases is their apparent ability to exhibit a substantial increase in efficiency after conditioning at high temperatures. Examples of this are found in Table B under the heading "Crosslinked Ionic Liquid Matrix." In one such example, a crosslinked matrix previously described containing a mixture of four dicationic crosslinkers, $C_{9-12}(vim)_2$-$NTf_2$ was formed and the efficiency of this stationary phase was observed to undergo a 200%-250% increase in efficiency when the column was conditioned from 300° C. to 350° C. (see Table B). This trend was observed on all highly crosslinked stationary phases examined and appears to be independent of the initial AIBN concentration in the coating solution (see Table C).

The fact that the efficiencies of the highly crosslinked stationary phases increase in this narrow temperature range is not well understood, but certainly makes them very useful for high temperature separations. Clearly, by exhibiting this behavior, these stationary phases appear to exhibit the smallest decrease in efficiency up to temperatures around 350° C. For low to moderate temperature separations (25° C. to 285° C.), the partially crosslinked stationary phases, particularly those containing equal weight percentages of ionic liquids 2 and 5, provide the highest efficiency separations up to 285° C. with little column bleed at temperatures at and above 250° C. Meanwhile, the completely crosslinked stationary phases provides the highest efficiency separations with little column bleed up to temperatures around 300° C.-380° C. Therefore, these two optimized types of immobilized ionic liquid stationary phases are specifically proposed for normal GC temperature ranges and higher GC temperatures, respectively. Low to moderate temperature separations are optimal with partial crosslinking of the stationary phase whereas high temperature separations require more extensive crosslinking to maintain acceptable efficiency and low column bleed.

The two optimized crosslinked stationary phases chosen for the moderate (0.10% 2 and 0.10% 5) and high temperature (0.20% $C_{9-12}(vim)_2$-$NTf_2$) separations, wer further studied to determine the effect of AIBN initiator concentration on their separation efficiency and thermal stability. As shown in Table B, each copolymer was formed using a different concentration of AIBN in the coating solution. These concentrations ranged from 10.0% (w/w of AIBN to ionic liquid) to 0.5%. For the partially crosslinked stationary phase, a higher weight percentage of initiator results in a slightly more efficient stationary phase (i.e., 3296 plates/meter for 0.5% AIBN to 3817 plates/meter for 10.0% AIBN). In addition, the efficiencies of the 7.0% and 10.0% by weight initiator copolymers decrease less rapidly at higher temperatures (>250° C.) compared to those ionic liquid matrices produced with lower initiator concentrations. After the stationary phase is subjected to a temperature ramp up to 385° C., only the two copolymers formed with 7.0% and 10.0% initiator provide retention of naphthalene, however with very low efficiency. The other two crosslinked stationary phases were no longer observed in the capillary after high temperature conditioning (385° C.) and therefore provided no retention.

In the case of the highly crosslinked stationary phase (0.20% $C_{9-12}(vim)_2$-$NTf_2$), a nearly opposite trend to that observed for the partially crosslinked ionic liquids was observed (Table B). The efficiencies of the columns after the first conditioning step are higher for the copolymers formed with lower AIBN concentration. However, it was still found that a higher weight percentage of AIBN results in a smaller decrease of efficiency at higher temperatures compared to the copolymers formed with lower percentages of AIBN. All of the highly crosslinked stationary phases were found to retain naphthalene after conditioning at 385° C. As discussed previously, the highly crosslinked stationary phases exhibit an increase in the separation efficiency for naphthalene after being conditioned to 350° C. as compared to being conditioned at only 300° C. The magnitude of this increase does not appear to be directly related to the initiator concentration. For example, the efficiency increase exhibited by the copolymer formed with 3.5% AIBN is ~171% higher after the 350° C. program compared to the 300° C. program whereas that for the 10% AIBN is ~250% higher. As previously observed for the partially crosslinked ionic liquids, the overall decrease in efficiency is lowest for copolymers formed with higher AIBN concentrations.

This indicates that at high temperatures the most efficient stationary phases appear to be those that are crosslinked with a weight percentage of AIBN greater than 7.0%. In contrast, for lower/normal temperature separations, the choice of the monocationic monomer and crosslinker plays a more important role in the stationary phase efficiency and higher initiator concentration tends to prevent large decreases in efficiency with increasing temperature (see Table B).

It has been demonstrated previously that room temperature ionic liquids act as broadly applicable, superb gas chromatographic stationary phases in that they exhibit a dual nature retention behavior.[44, 50, 51] Consequently, ionic liquid stationary phases have been shown to separate, with high efficiency, both polar and nonpolar molecules on a single column. By producing stationary phases that are either partially or highly crosslinked, it is of interest to ensure that the solvation thermodynamics and solvation interactions inherent to ionic liquids are still retained by their immobilized analogues.

The thermodynamics (Table D) and solvation interactions (Table E) for the two optimized crosslinked and a neat ionic liquid were determined as previously described in the Experimental Section. As can be seen from the data in these tables, both the free energy of transfer of solute and particularly their interaction parameters are similar for both the crosslinked and neat monomeric ionic liquid stationary phases. While the enthalpies of solvation for all probe molecules differed only slightly between the three ionic liquids, a larger difference was observed for the entropies of solvation on the highly crosslinked stationary phase for certain solutes, i.e., 2-chloroaniline, ethyl phenyl ether, and decane. The entropies of solvation were somewhat more negative for these molecules indicating that they are part of a more ordered environment with the highly crosslinked stationary phase. These results also indicate that solvation by these three ionic liquid-based stationary phases has a substantial entropic component that contributes to large differences in solute free energy of transfer (see values for 2-chloroaniline and decane in Table D).

The solvation interaction parameters given in Table E indicate that the neat and two crosslinked ionic liquids are very similar in terms of selectivity. All three stationary phases interact weakly via nonbonding and π-electrons (r-term). The hydrogen bond basicity (a) and dispersion forces (l) were the same within experimental error for all three stationary phases. The partially crosslinked and neat ionic liquids possessed the same magnitude of dipolar interactions which were somewhat lower than those exhibited by the highly crosslinked ionic liquid (see Table E). Within experimental error, all three ionic liquids possessed the same ability to undergo hydrogen bond acidity (b) interactions.

Figure 6:
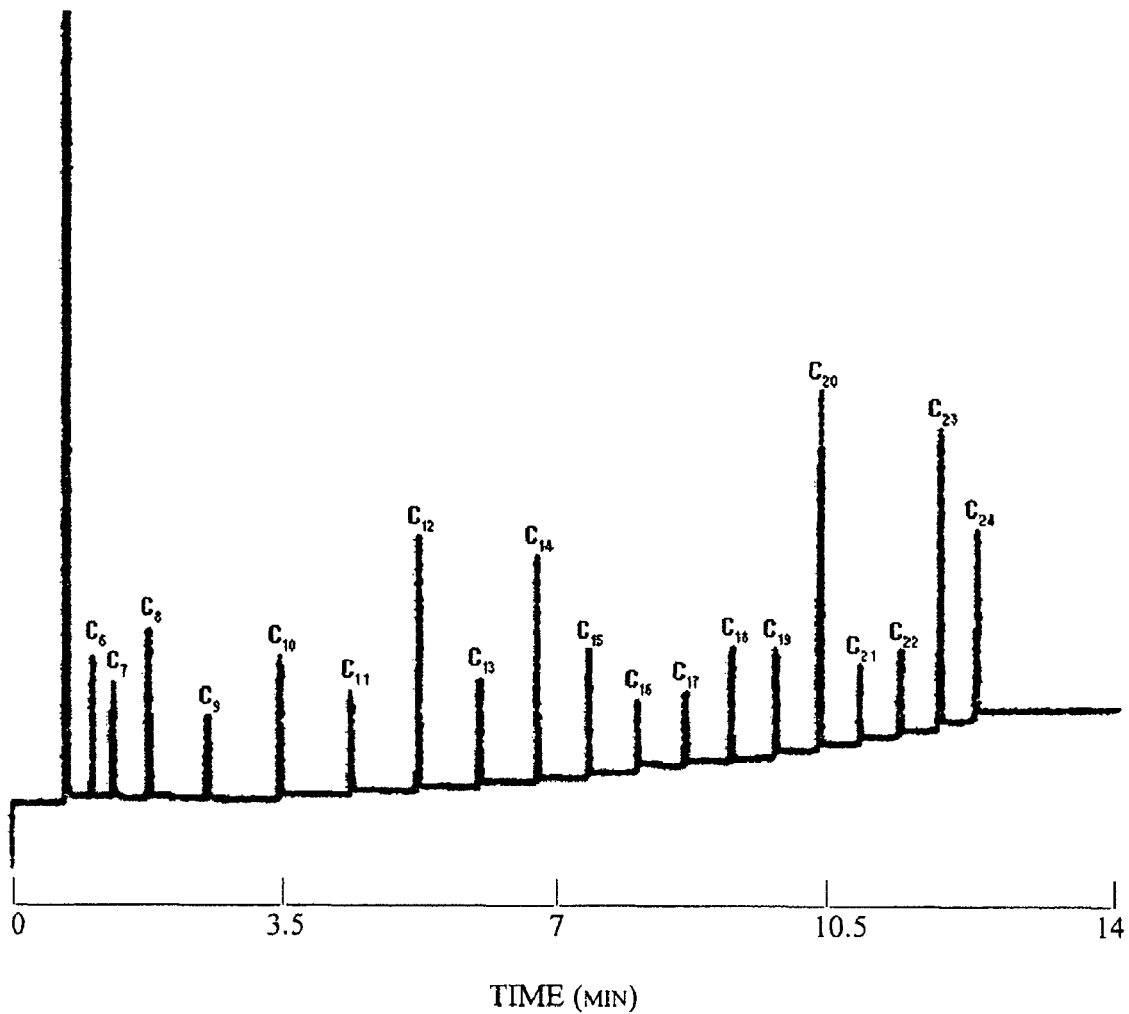
FIG. 6 is a chromatogram showing the separation of fatty acid methyl esters (C$_6$-C$_{24}$) on a 15 meter partially cross-linked ionic liquid stationary phase (0.10% nvim-NTf$_2$ (2)/10% C$_9$(vim)2-NTf$_2$ (5) with 7.5% AIBN). Conditions: 100° C. hold 2 minutes, 15° C./min to 260° C.
Figure 7:
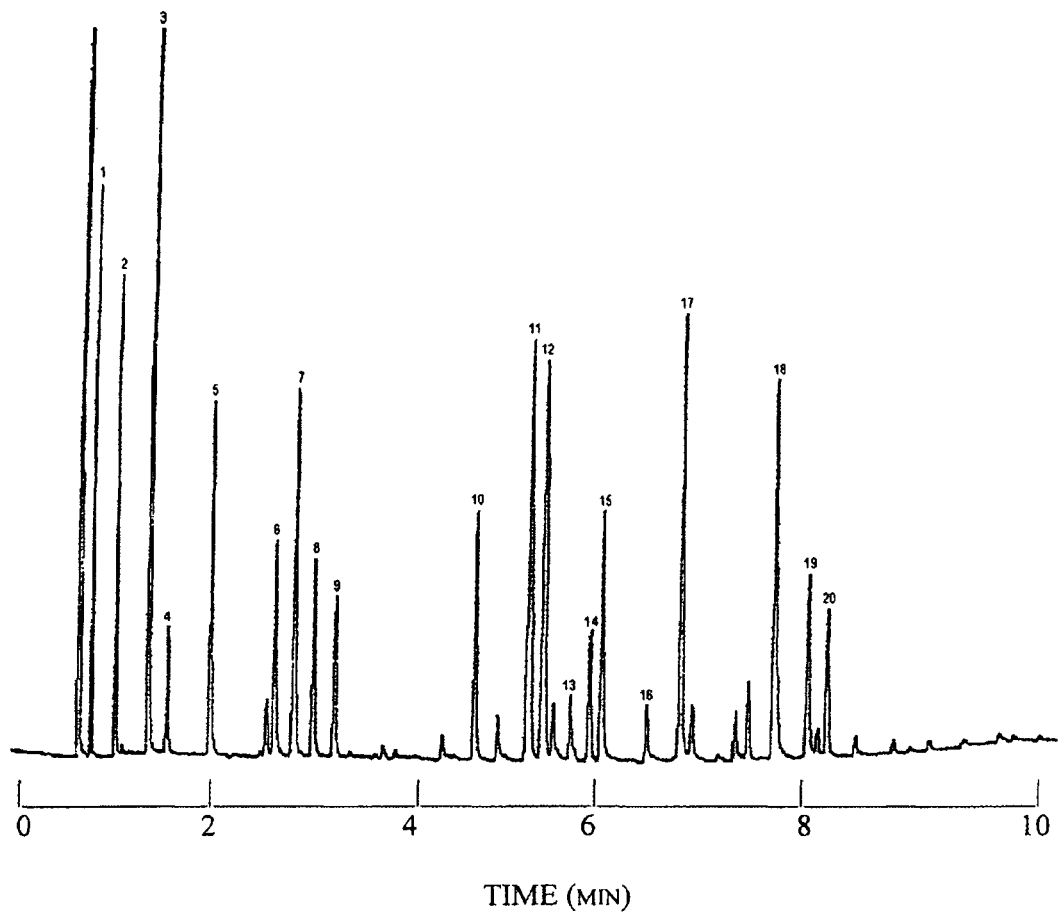
FIG. 7 is a chromatogram showing the Separation of PAH and chlorinated pesticide mixture on a 13 meter C$_9$(vim)$_2$-NTf$_2$ (7.5% AIBN) more likely cross-linked ionic liquid stationary phase. 1, indene; 2, naphthalene; 3, biphenyl; 4, azulene; 5, acenaphthene; 6, acenaphthylene; 7, heptachlor; 8, fluorene; 9, BHC; 10, dibenzothiophene; 11, DDE; 12; endosulfan; 13, anthracene; 14, dieldrin; 15, 4H-cyclopenta[def]phenanthrene; 16, fluoranthene; 17, DDT; 18, lindane; 19, pyrene; 20, carbazole. Conditions: 175° C. for 1 min; 20° C./min to 335° C. The smaller, unnumbered peaks in this chromatogram are impurities contained in numbered standard materials.

The unique selectivity of ionic liquid stationary phases in the separation of a wide variety of analyte molecules including alcohols, alkanes, polycyclic aromatic hydrocarbons (PAHs), polychlorinated biphenyls (PCBs), and chlorinated pesticides have been demonstrated.[51] The fact that the selectivity of the ionic liquid stationary phases is preserved after crosslinking the matrix is demonstrated in FIGS. 6 and 7. FIG. 6 shows a separation of 19 fatty acid methyl esters (FAMEs) on a 15 meter column coated with a partially crosslinked IL stationary phase. This separation is performed in 12 minutes using the temperature ramp described. FIGS. 7 illustrates the separation of a mixture of PAHs and chlorinated pesticides on a 12 meter highly crosslinked stationary phase. The 9 minute, high temperature GC separation is carried out using a temperature program up to 335° C. with little observed column bleed. While the selectivity of these ionic liquids is little different from that observed previously with the neat ionic liquids,[51] the fact that separations can now be accomplished at higher temperatures with little column bleed, high efficiency, and little shifting of the retention time after exposure to extreme temperatures further demonstrates the effectiveness of the immobilized ionic liquid.

This work addresses the fundamental issues relating to the use of ionic liquid stationary phases at high temperatures and column ruggedness. Specifically, it was demonstrated that by employing ionic liquid monocationic monomers and dicationic crosslinkers, an immobilized GC stationary phase can be developed. The cross-linked stationary phases retain the dual nature selectivity behavior inherent to all ionic liquid stationary phases. In addition, the columns can be used at high temperatures with low column bleed while simultaneously providing high efficiency separations. Two types of stationary phases were identified in this work and differ in terms of their maximum/minimum operating temperatures. Partially crosslinked stationary phases are best for separations conducted at temperatures from ambient to 280° C. while a mostly crosslinked stationary phase is best suited for temperatures over 300° C. While the moderate to high temperature range of the mostly crosslinked stationary phase may overlap with the partially crosslinked matrix, lower efficiency separations were observed with the mostly crosslinked stationary phase at low temperatures. Moreover, a dramatic increase in efficiency of the mostly crosslinked stationary phase at high temperatures further adds to its effectiveness and usefulness for a variety of applications in high temperature gas chromatography studies.

Of course, ionic liquids and in particular the diionic liquid salts of the present invention can be used in other separation and analytical techniques. Their range of applicability is in no way limited to chromatography. One technique in which these materials can be used in Solid Phase Extraction ("SPE"). In SPE, a sample contains an impurity or some other element to be separated, identified and/or quantified. This sample can be placed into a container in which diionic liquid salts of the present invention can be present in, and more broadly, ionic liquids in an immobilized form. Ionic liquid materials can be bound (immobilized) to the walls of the container, adsorbed, absorbed onto a bead or other structure so as to form a bead or other structure which may rest at the bottom of the container or be packed throughout the container much as a liquid chromatography column can be packed with stationary phase. Alternatively, the ionic liquids and in particular diionic liquid salts of the present invention can be immobilized by cross-linking or an analogous immobilization reaction as described herein on some sort of other solid support such as a bead used in chromatography. These beads can also be placed at the bottom of, or can fill a container, much as a packed column used for liquid chromatography. Of course, the solid support can be any structure placed any where within the container.

In a particularly preferred embodiment, the container is actually a syringe where the ionic liquid and/or diionic liquid salts are affixed or disposed in one fashion or another at the base of the syringe, much as a filter. When the needle of the syringe is placed in a sample and the plunger is withdrawn, vacuum is formed drawing sample up into the barrel of the syringe. This material would pass through at least one layer of ionic liquid and, in particular, diionic liquid salts in accordance with the present invention, which would bind at least one of the components of the liquid. The sample liquid could then be spilled out or the plunger depressed to eject it, the latter forcing the sample back through the ionic liquid or diionic liquid salts positioned at the bottom of the barrel.

The liquid can be analyzed either for the presence of certain materials or the absence of the material retained by the ionic liquid or diionic liquid salts of the present invention. Alternatively, the retained materials can be removed (such as by placing the materials in a different solvent) or not and analyzed analytically by other means. The same technique may be used in a preparative fashion and/or as a means of bulk purification as well.

Another technique in which immobilized ionic liquids and diionic liquid salts of the present invention may be used is solid phase microextraction or SPME. Broadly speaking, in these techniques, a separation material (in this case an ionic liquid or in particular a diionic liquid salt in accordance with the present invention) is absorbed, adsorbed or immobilized in one way or another on a fiber generally attached to a plunger in a microsyringe such as usually used in gas chromatography. In the case of the invention, immobilized ionic liquids and absorbed, adsorbed and immobilized diionic liquid salts are contemplated. The plunger is depressed, exposing the fiber and the fiber is then dipped into the sample of interest. The plunger can then be withdrawn to pull the fiber back into the barrel of the syringe, or at least the barrel of the needle for protection and transport. The syringe can then be injected through the septum of a gas chromatograph or some other device and the fiber thereby inserted into the column by redepressing the plunger of the microsyringe. The heat used in GC then volatilizes or otherwise drives the bound sample off where it is carried by the mobile phase through the GC column, allowing for separation and/or identification. It can also be eluted by a liquid mobile phase in an HPLC injector or unbuffer capillary electrophoresis.

More specifically, solid phase microextraction is a technique in which a small amount of extracting phase (in this case an ionic liquid and preferably a diionic liquid salt in accordance with the present invention) is disposed on a solid support, which was then exposed to a sample for a period of time. In situations where the sample is not stirred, a partitioning equilibrium between a sample matrix and the extraction phase is reached. In cases where convection is constant, a short time pre-equilibrium extraction is realized and the amount of analyte extracted is related to time. Quantification can then be performed based on the timed accumulation of analysis in the coating. These techniques are usually performed using open bed extraction concepts such as by using coated fibers (e.g., fused silica similar to that used in capillary GC or capillary electrophoresis, glass fibers, wires, metal or alloy fibers, beads, etc.), vessels, agitation mechanism discs and the like. However, in-tube approaches have also been demonstrated. In-tube approaches require the extracting phase to be coated on the inner wall of the capillary and the sample containing the analyte of interest is subject to the capillary and the analytes undergo partitioning to the extracting phase. Thus, material can be coated on the inner wall of a needle, for example, and the needle injected without the need for a separate solid support.

Figure 8:
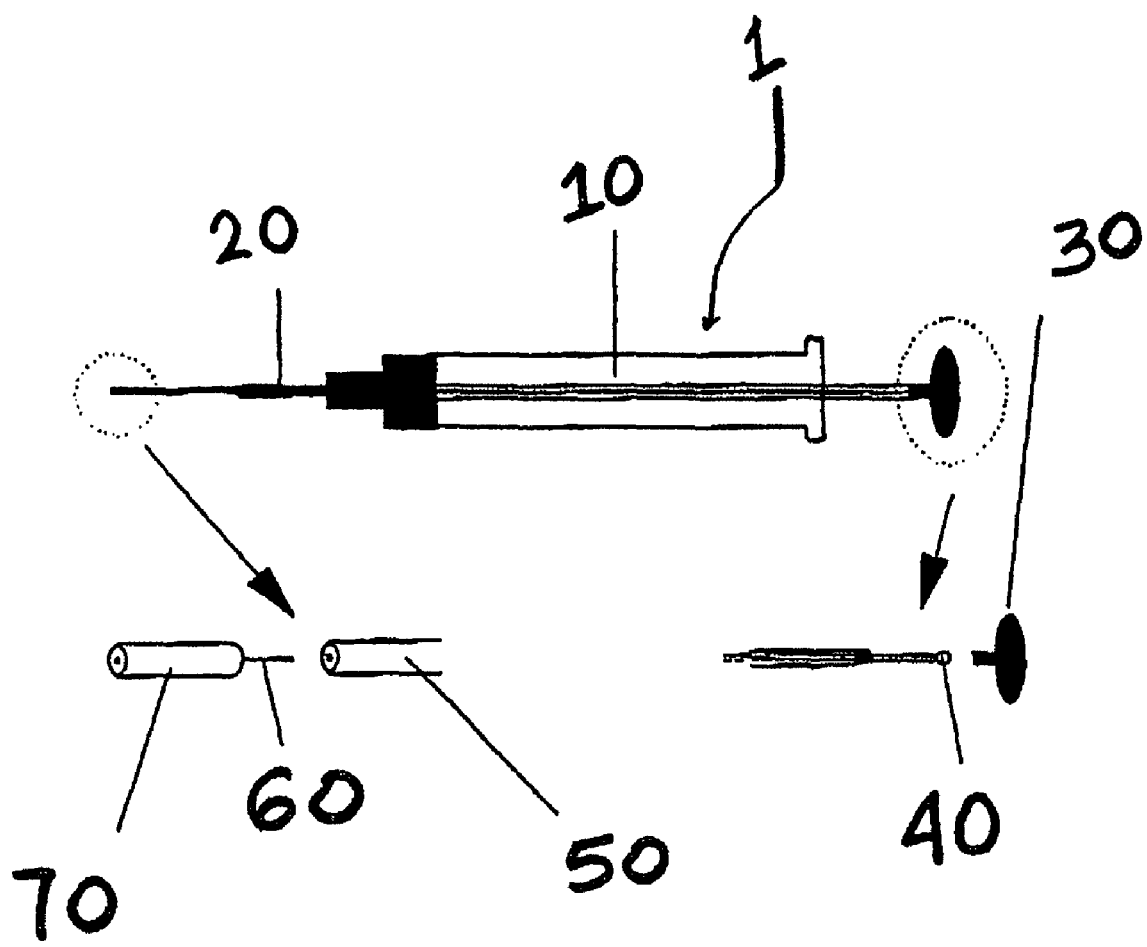
FIG. 8 is a syringe useful for SPME and SPME/MALDI mass spectrometry.
Figure 9:
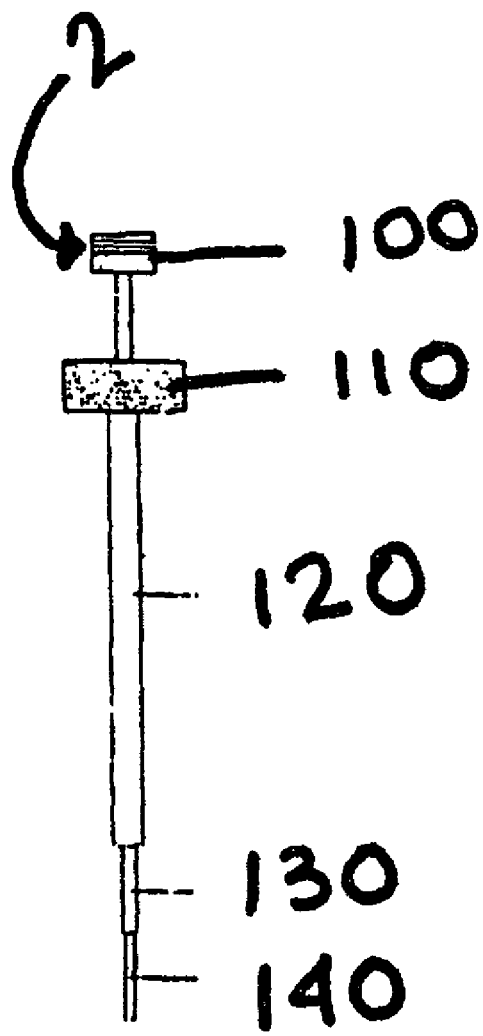
FIG. 9 is another syringe useful for SPME and SPME/MALDI mass spectrometry.

FIG. 8 shows an example of an SPME device (1). A stainless steel microtube 40 having an inside diameter slightly larger than the outside diameter of, for example, a fuse silica rod 60 is used. Typically, the first 5 mm is removed from a 1.5 cm long fiber, which is then inserted into the microtubing. High temperature epoxy glue is used to permanently mount the fiber. Sample injection is then very much like standard syringe injection. Movement of the plunger 30 allows exposure of the fiber 60 during extraction and desorption and its protection in the needle 20 during storage and penetration of the septum. 10 shows the barrel of the microsyringe, 50 shows the extreme end of the stainless steel microtube in which the silicon fiber is mounted. Another version of a syringe useful for SPME in accordance with the present invention is illustrated in FIG. 9. Syringe 2 can be built from a short piece of stainless steel microtubing 130 to hold the fiber. Another piece of larger tubing 120 works as the needle. A septum 110 is used to seal the connection between the microtubing 130 and the needle 120. The silica fiber 140 is exposed through one end of the microtubing 130 and the other end is blocked by a plunger 100. Withdrawing plunger 100 retracts microtubing 130 and the fiber 140 into the barrel of the device, the needle 120. Depressing plunger 100 reverses this process. These are but exemplary structures and any syringe device, including those containing a needle or tube with the ionic liquid immobilized on the inner surface thereof are also contemplated.

Any monoionic liquid or diionic liquid salt may be used in accordance with the present invention. Diionic liquids such as those shown immediately below can be absorbed or adsorbed onto a solid support as previously described.

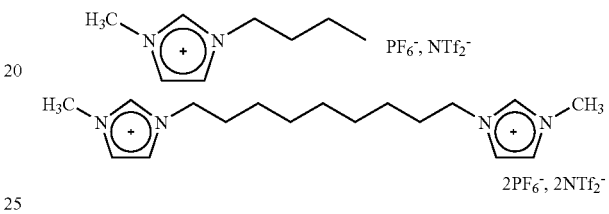

In addition, ionic liquids, both monoionic and diionic liquid salts in accordance with the present invention can be immobilized by being bound or cross-linked to themselves and to a solid support as previously discussed in connection with manufacturing capillary GC columns. To do so, however, the species used should have at least one unsaturated group disposed to allow reaction resulting in immobilization. See for example the monocationic and dicationic species immediately below.

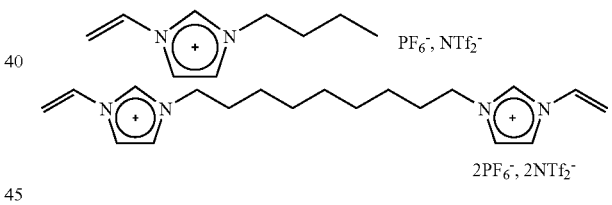

Another type of SPME technique is known as task specific SPME or TSSPME. Task specific SPME allows for the separation or removal, and therefore the detection of particular species. These can include, for example, mercury and cadmium, although the technique is equally applicable to other materials. The concept is exactly the same as previously described with regard to SPME. However, in this instance, the ionic liquids or diionic liquids used are further modified such that they will specifically interact with a particular species. Those shown below, for example, may be used in the detection of cadmium and mercury ($Cd^{2+}$ or $Hg^{2+}$). The first monocationic material can be coated, absorbed or adsorbed onto a fiber as previously discussed. A diionic liquid salt can also be absorbed or adsorbed in known fashion. The second and third ionic liquid materials illustrated below, the first monoionic and the second dicationic, by virtue of the presence of unsaturated groups, can be more easily immobilized on a solid support using techniques analogous to those described previously with regard to cross-linking in connection with manufacturing capillary GC columns.

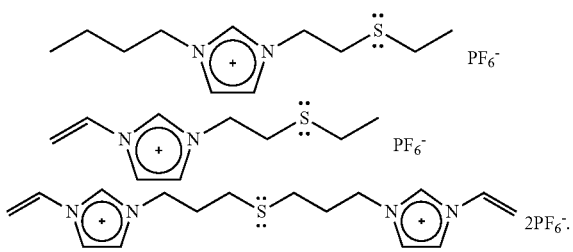

Finally, a particular sample can be suspended in a matrix that includes ionic liquids and preferably diionic liquid salts in accordance with the present invention. This matrix can be loaded or immobilized on the fiber of an SPME syringe as described above and then injected into a mass spectrometer to practice a technique known as SPME/MALDI mass spectrometry.[55] The matrix is exposed to a UV laser. This causes the volatilization or release of the sample much as heat does in a GC. This allows the sample to enter mass spectrometer where it can be analyzed. Ionic materials which can be used as a matrix include, without limitation:

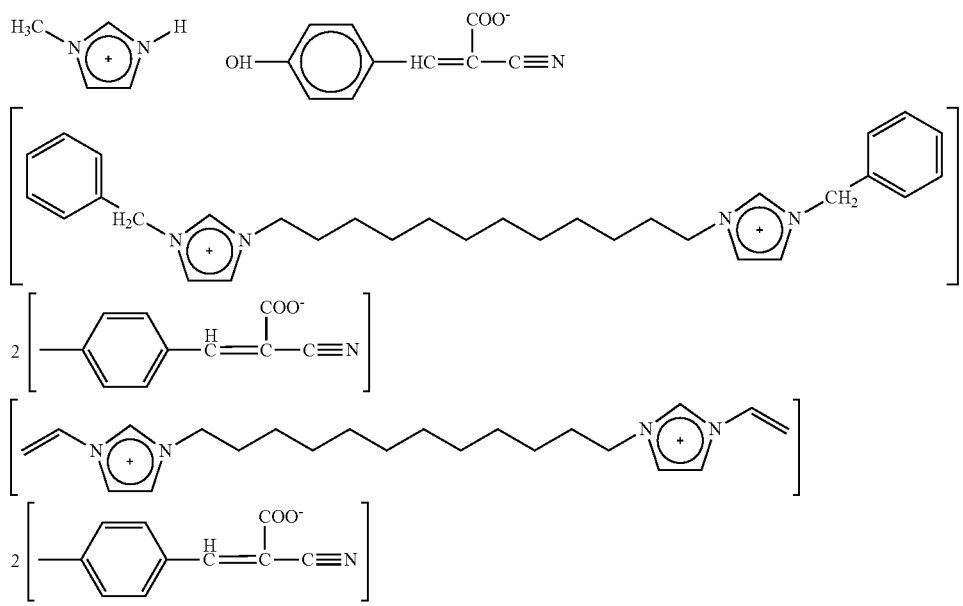

TABLE A

Structure and physico-chemical properties of the monomers/crosslinkers used in this study.

| # | Ionic Liquid | Molecular Weight (g/mol) | Density (g/cm³) | Refractive Index |
|---|---|---|---|---|
| 1 | hvim-NTf₂[a] | 459.1 | 1.36 | 1.443 |
| 2 | nvim-NTf₂[b] | 501.2 | 1.28 | 1.445 |
| 3 | dvim-NTf₂[c] | 543.3 | 1.23 | 1.448 |

TABLE A-continued

Structure and physico-chemical properties of the monomers/crosslinkers used in this study.

| # | Ionic Liquid | Molecular Weight (g/mol) | Density (g/cm³) | Refractive Index |
|---|---|---|---|---|
| 4 | 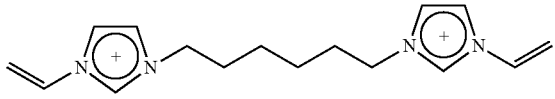<br>2NTf$_2^-$<br>C$_6$(vim)$_2$-NTf$_2$$^d$ | 832.1 | | |
|   | 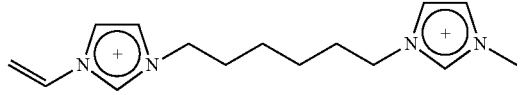<br>2NTf$_2^-$<br>C$_6$vm(im)$_2$-NTf$_2$$^e$ | 820.1 | 1.53 | 1.449 |
|   | 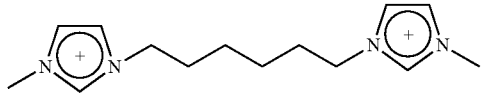<br>2NTf$_2^-$<br>C$_6$(mim)$_2$-NTf$_2$$^f$ | 808.1 | | |
|   | C$_6$(vim)$_2$-NTf$_2$:C$_6$vm(im)$_2$-NTf$_2$:C$_6$(mim)$_2$-NTf$_2$<br>1:2:1 | | | |
| 5 | 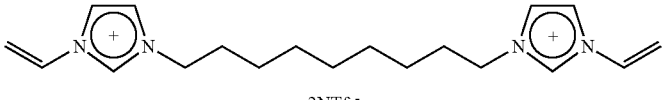<br>2NTf$_2^-$<br>C$_9$(vim)$_2$-NTf$_2$$^g$ | 874.3 | 1.47 | 1.457 |
| 6 | 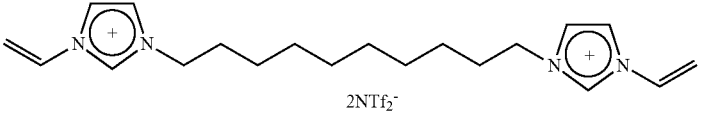<br>2NTf$_2^-$<br>C$_{10}$(vim)$_2$-NTf$_2$$^{h,*}$ | 888.3 | — | — |
| 7 | 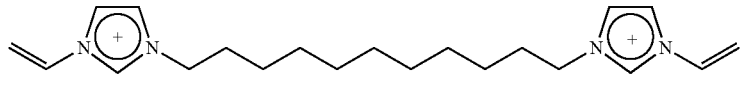<br>2NTf$_2^-$<br>C$_{11}$(vim)$_2$-NTf$_2$$^i$ | 902.3 | 1.44 | 1.457 |
| 8 | 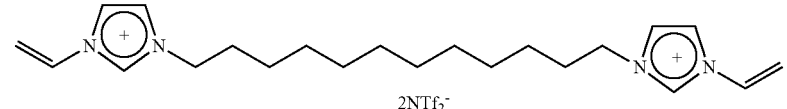<br>2NTf$_2^-$<br>C$_{12}$(vim)$_2$-NTf$_2$$^{j,*}$ | 916.3 | 1.42 | 1.458 |
| 9 | 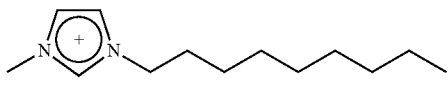<br>NTf$_2^-$<br>nmim-NTf$_2$$^k$ | 489.3 | 1.30 | 1.434 |

TABLE B

Effect of monomer structure and degree of crosslinking on stationary phase efficiency (theoretical plates/mater) as a function of conditioning temperature.

| | Monocationic Linear Ionic Liquid Polymers[a] | | | Partially Crosslinked Ionic Liquid Matrix[a] | | | | | |
|---|---|---|---|---|---|---|---|---|---|
| | | | | | 0.10% 1 | 0.15% 1 | 0.05% 1 | 0.10% 1 | 0.10% 2 |
| | 0.20% 1 | 0.20% 2 | 0.20% 3 | 0.20% 4 | 0.10% 4 | 0.05% 4 | 0.15% 4 | 0.10% 5 | 0.10% 4 |
| 30° C.-120° C. 3° C./min Hold 2 hours | 2813 | 2429 | 1860 | 2926 | 2916 | 2714 | 1768 | 3660 | 2938 |
| 100° C.-200° C. 3° C./min Hold 5 hours | 2415 | 2322 | 1694 | 2426 | 2769 | 2085 | 1679 | 3301 | 2775 |
| 150° C.-250° C. 3° C./min Hold 3 hours | 2172 | 2026 | 1706 | 1945 | 2639 | 2156 | 1827 | 2743 | 2449 |
| 200° C.-285° C. 3° C./min Hold 2 hours | 1778 | 1677 | 1100 | 1710 | 2180 | 2047 | 1623 | 2088 | 2302 |
| 200° C.-300° C. 3° C./min Hold 1 hour | 1542 | 1432 | 1090 | 1517 | 1835 | 1626 | 1226 | 1419 | 2058 |
| 200° C.-350° C. 3° C./min Hold 1 hour | 197 | 142 | 120 | 1365 | 417 | 433 | 719 | 1119 | 523 |
| 200° C.-380° C. 3° C./min Hold 20 min | — | — | — | 193 | — | — | — | 291 | — |

| | Partially Crosslinked Ionic Liquid Matrix[a] | | | Crosslinked Ionic Liquid Matrix[a] | |
|---|---|---|---|---|---|
| | | | | | 0.10% 1 |
| | 0.10% 2 0.10% 5 | 0.10% 3 0.10% 4 | 0.20% 5 | 0.20% $C_{9-12}(vim)_2$-$NTf_2$ | 0.10% $C_{9-12}(vim)_2$-$NTf_2$ |
| 30° C.-120° C. 3° C./min Hold 2 hours | 3566 | 2957 | 3206 | 3189 | 3155 |
| 100° C.-200° C. 3° C./min Hold 5 hours | 3277 | 2872 | 3019 | 2634 | 2379 |
| 150° C.-250° C. 3° C./min Hold 3 hours | 3016 | 2787 | 2469 | 1963 | 1598 |
| 200° C.-285° C. 3° C./min Hold 2 hours | 2536 | 2361 | 1554 | 898 | 771 |
| 200° C.-300° C. 3° C./min Hold 1 hour | 2024 | 2157 | 1334 | 941 | 554 |
| 200° C.-350° C. 3° C./min Hold 1 hour | 146 | 340 | 2101 | 1891 | 950 |
| 200° C.-380° C. 3° C./min Hold 20 min | — | — | 503 | 269 | 239 |

[a] Ionic liquid polymer formed using 3.5% AIBN

TABLE C

Effect of AIBN initiator concentration on efficiency (theoretical plates/meter) as a function of conditioning of the crosslinked stationary phase. The percentage of AIBN initiator indicated is based on the weight percent of the ionic liquid.

| | Partially Crosslinked Ionic Liquid Matrix | | | | Crosslinked Ionic Liquid Matrix | | | |
|---|---|---|---|---|---|---|---|---|
| | 0.10% 2 0.10% 5 0.5% AIBN | 0.10% 2 0.10% 5 3.5% AIBN | 0.10% 2 0.10% 5 7.0% AIBN | 0.10% 2 0.10% 5 10.0% AIBN | 0.20% $C_{9-12}(vim)_2$-$NTf_2$ 0.5% AIBN | 0.20% $C_{9-12}(vim)_2$-$NTf_2$ 3.5% AIBN | 0.20% $C_{9-12}(vim)_2$-$NTf_2$ 7.0% AIBN | 0.20% $C_{9-12}(vim)_2$-$NTf_2$ 10.0% AIBN |
| 30° C.–120° C. 3° C./min Hold 2 hours | 3296 | 3566 | 3831 | 3817 | 3426 | 3155 | 2792 | 2905 |
| 100° C.–200° C. 3° C./min Hold 5 hours | 3215 | 3277 | 3703 | 3529 | 2697 | 2379 | 2275 | 2309 |
| 150° C.–250° C. 3° C./min Hold 3 hours | 3090 | 3016 | 3069 | 3027 | 1723 | 1598 | 1682 | 1398 |
| 200° C.–285° C. 3° C./min Hold 2 hours | 2210 | 2536 | 2375 | 2559 | 950 | 771 | 865 | 649 |
| 200° C.–300° C. 3° C./min Hold 1 hour | 1317 | 2024 | 2298 | 2009 | 676 | 554 | 768 | 603 |
| 200° C.–350° C. 3° C./min Hold 1 hour | 112 | 146 | 598 | 1214 | 1593 | 950 | 1664 | 1506 |
| 285° C.–385° C. 3° C./min Hold 20 min | — | — | 140 | 68 | 178 | 239 | 490 | 453 |

TABLE D

Comparsion of solvation thermodynamics of one neat and two crosslinked ionic liquids.

| | Temp. Range (° C.) | | Partially Crosslinked IL 0.10% nvim-$NTf_2$ (2) 0.10% $C_9(vim)_2$-$NTf_2$ (5) 3.5% AIBN | | | Neat Monomeric IL 0.20% nmim-$NTf_2$(9) | | | Mostly Crosslinked IL 0.20% $C_{9-12}(vim)_2$-$NTf_2$[a] 3.5% AIBN | | |
|---|---|---|---|---|---|---|---|---|---|---|---|
| Probe Molecule | Min | Max | ΔG (J/mol) | $\Delta H_{AV}$ (J/mol) | $\Delta S_{AV}$ (J/mol *K) | ΔG (J/mol) | $\Delta H_{AV}$ (J/mol) | $\Delta S_{AV}$ (J/mol *K) | ΔG (J/mol) | $\Delta H_{AV}$ (J/mol) | $\Delta S_{AV}$ (J/mol *K) |
| Fluorophenol | 40 | 100 | −6071 (70° C.) | −49308 ± 31.0 | −126 ± 2.3 | −6583 (70° C.) | −48104 ± 79.5 | −121 ± 0.25 | −5429 (70° C.) | −48323 ± 482.7 | −125 ± 1.52 |
| Naphthalene | 40 | 100 | −10087 (70° C.) | −54353 ± 23.7 | −129 ± 0.67 | −10209 (70° C.) | −53789 ± 91.0 | −127 ± 0.31 | −8902 (70° C.) | −52825 ± 52.3 | −128 ± 0.15 |
| 2-Chloroaniline | 40 | 100 | −11320 (70° C.) | −56616 ± 18.1 | −132 ± 0.06 | −11670 (70° C.) | −57652 ± 57.5 | −134 ± 0.17 | −10064 (70° C.) | −57075 ± 63.4 | −137 ± 0.21 |
| Ethyl Phenyl Ether | 35 | 75 | −7058 (50° C.) | −46482 ± 140 | −122 ± 0.52 | −7420 (50° C.) | −46521 ± 69.0 | −121 ± 0.21 | −5622 (50° C.) | −46662 ± 409 | −127 ± 1.31 |
| 1-Octanol | 35 | 75 | −10433 (50° C.) | −59229 ± 50.7 | −151 ± 0.23 | −10481 (50° C.) | −59277 ± 58.2 | −151 ± 0.44 | −8213 (50° C.) | −56039 ± 58.1 | −148 ± 0.15 |
| Decane | 35 | 75 | −4457 (50° C.) | −45497 ± 363 | −127 ± 1.5 | −4349 (50° C.) | −45389 ± 138 | −127 ± 0.46 | −1813 (50° C.) | −46408 ± 98.7 | −138 ± 3.52 |
| Nitropropane | 27 | 50 | −5220 (35° C.) | −38808 ± 49.5 | −109 ± 0.17 | −5422 (35° C.) | −39010 ± 312 | −109 ± 1.0 | −4367 (35° C.) | −38263 ± 198 | −110 ± 0.60 |

[a]This mixture consists of a combination of a homologous series of ionic liquids that are 10.88% by weight 5, 9.29% of 6, 19.59% of 7, and 60.24% of 8.

TABLE E

Comparison of interaction parameters of one neat and two crosslinked ionic liquids.

| Temp (° C.) 0.20% nmim-NTf$_2$(9) | c | r | s | a | b | l | n | $R^2$ | F |
|---|---|---|---|---|---|---|---|---|---|
| 40 | −2.98 (0.11) | 0 (0.09) | 1.62 (0.10) | 1.91 (0.10) | 0.36 (0.13) | 0.75 (0.03) | 32 | 0.99 (0.10) | 477.86 |
| 70 | −3.05 (0.08) | 0 (0.07) | 1.54 (0.07) | 1.57 (0.07) | 0.18 (0.10) | 0.63 (0.02) | 32 | 0.99 (0.07) | 660.78 |
| 100 | −3.47 (0.11) | 0 (0.09) | 1.52 (0.10) | 1.43 (0.09) | 0.12 (0.13) | 0.60 (0.03) | 30 | 0.99 (0.09) | 304.17 |
| 0.10% C$_9$(vim)-NTf$_2$ (2); 0.10% C$_9$(vim)$_2$-NTf$_2$ (5); 3.5% AIBN | | | | | | | | | |
| 40 | −2.95 (0.11) | 0 (0.10) | 1.60 (0.11) | 1.84 (0.10) | 0.45 (0.15) | 0.71 (0.03) | 32 | 0.99 (0.10) | 404.82 |
| 70 | −3.05 (0.08) | 0 (0.07) | 1.57 (0.08) | 1.53 (0.07) | 0.37 (0.10) | 0.60 (0.02) | 32 | 0.99 (0.07) | 639.52 |
| 100 | −3.49 (0.12) | 0 (0.09) | 1.54 (0.11) | 1.41 (0.09) | 0.31 (0.14) | 0.54 (0.03) | 30 | 0.98 (0.09) | 299.60 |
| 0.20% C$_{9-12}$(vim)$_2$-NTf$_2$[b]; 3.5% AIBN | | | | | | | | | |
| 40 | −3.31 (0.10) | 0 (0.09) | 1.92 (0.10) | 1.94 (0.09) | 0.59 (0.13) | 0.68 (0.03) | 32 | 0.99 (0.09) | 573.26 |
| 70 | −3.55 (0.12) | 0 (0.10) | 1.88 (0.11) | 1.71 (0.09) | 0.46 (0.15) | 0.59 (0.03) | 32 | 0.99 (0.10) | 305.25 |
| 100 | −3.65 (0.13) | 0 (0.11) | 1.73 (0.13) | 1.46 (0.12) | 0.32 (0.18) | 0.48 (0.04) | 30 | 0.98 (0.11) | 254.83 |

[a] r = interaction via nonbonding and π-electrons, s = dipolarity/polarizability, a = hydrogen bond basicity, b = hydrogen bond acidity, l = dispersion forces, n = number of probe molecules subjected to multiple linear regression analysis, $R^2$ = statistical correlation coefficient, F = Fisher coefficient. Values in parenthesis are the standard deviations for each interaction parameter.
[b] This mixture consists of a combination of a homologous series of ionic liquids that are 10.88% by weight of 5, 9.29% of 6, 19.59% of 7, and 60.24% of 8.

TABLE F

Names of Compounds Found in Tables 1 and 2

| | |
|---|---|
| C$_3$(mim)$_2$-Br | 1,3-di(3-methylimidazolium)propane di-bromide |
| C$_3$(mim)$_2$-NTf$_2$ | 1,3-di(3-methylimidazolium)propane di-bis[(trifluoromethyl)sulfonyl]imidate |
| C$_3$(mim)$_2$-BF$_4$ | 1,3-di(3-methylimidazolium)propane di-tetrafluoroborate |
| C$_3$(mim)$_2$-PF$_6$ | 1,3-di(3-methylimidazolium)propane di-hexafluorophosphate |
| C$_6$(mim)$_2$-Br | 1,6-di(3-methylimidazolium)hexane di-bromide |
| C$_6$(mim)$_2$-NTf$_2$ | 1,6-di(3-methylimidazolium)hexane di-bis[(trifluoromethyl)sulfonyl]imida |
| C$_6$(mim)$_2$-BF$_4$ | 1,6-di(3-methylimidazolium)hexane di-tetrafluoroborate |
| C$_6$(mim)$_2$-PF$_6$ | 1,6-di(3-methylimidazolium)hexane di-hexafluorophosphate |
| C$_9$(mim)$_2$-Br | 1,9-di(3-methylimidazolium)nonane di-bromide |
| C$_9$(mim)$_2$-NTf$_2$ | 1,9-di(3-methylimidazolium)nonane di-bis[(trifluoromethyl)sulfonyl]imidate |
| C$_9$(mim)$_2$-BF$_4$ | 1,9-di(3-methylimidazolium)nonane di-tetrafluoroborate |
| C$_9$(mim)$_2$-PF$_6$ | 1,9-di(3-methylimidazolium)nonane di-hexafluorophosphate |
| C$_{12}$(mim)$_2$-Br | 1,12-di(3-methylimidazolium)dodecane di-bromide |
| C$_{12}$(mim)$_2$-NTf$_2$ | 1,12-di(3-methylimidazolium)dodecane di-bis[(trifluoromethyl)sulfonyl]imidate |
| C$_{12}$(mim)$_2$-BF$_4$ | 1,12-di(3-methylimidazolium)dodecane di-tetrafluoroborate |
| C$_{12}$(mim)$_2$-PF$_6$ | 1,12-di(3-methylimidazolium)dodecane di-hexafluorophosphate |
| C$_9$(bim)$_2$-Br | 1,9-di(3-butylimidazolium)nonane di-bromide |
| C$_9$(bim)$_2$-NTf$_2$ | 1,9-di(3-butylimidazolium)nonane di-bis[(trifluoromethyl)sulfonyl]imidate |
| C$_9$(bim)$_2$-BF$_4$ | 1,9-di(3-butylimidazolium)nonane di-tetrafluoroborate |
| C$_9$(bim)$_2$-PF$_6$ | 1,9-di(3-butylimidazolium)nonane di-hexafluorophosphate |
| C$_3$(m$_2$im)$_2$-Br | 1,3-di(2,3-dimethylimidaolium)propane di-bromide |
| C$_3$(m$_2$im)$_2$-NTf$_2$ | 1,3-di(2,3-dimethylimidazolium)propane di-bis[(trifluoromethyl)sulfonyl]imidate |
| C$_3$(m$_2$im)$_2$-PF$_6$ | 1,3-di(2,3-dimethylimidazolium)propane di-hexafluorophosphate |
| C$_9$(m$_2$im)$_2$-Br | 1,9-di(2,3-dimethylimidazolium)nonane di-bromide |
| C$_9$(m$_2$im)$_2$-NTf$_2$ | 1,9-di(2,3-dimethylimidazolium)nonane di-bis[(trifluoromethyl)sulfonyl]imidate |
| C$_9$(m$_2$im)$_2$-BF$_4$ | 1,9-di(2,3-dimethylimidazolium)nonane di-tetrafluoroborate |
| C$_9$(m$_2$im)$_2$-PF$_6$ | 1,9-di(2,3-dimethylimidazolium)nonane di-hexafluorophosphate |
| C$_{12}$(benzim)$_2$-Br | 1,12-di(3-benzylimidazolium)dodecane di-bromide |
| C$_{12}$(benzim)$_2$-NTf$_2$ | 1,12-di(3-benzylimidazolium)dodecane di-bis[(trifluoromethyl)sulfonyl]imidate |
| C$_{12}$(benzim)$_2$-PF$_6$ | 1,12-di(3-benzylimidazolium)dodecane di-hexafluorophosphate |
| C$_3$(mpy)$_2$-Br | 1,3-di(methylpyrrolidinium)propane di-bromide |
| C$_3$(mpy)$_2$-NTf$_2$ | 1,3-di(methylpyrrolidinium)propane di-bis[(trifluoromethyl)sulfonyl]imidate |
| C$_3$(mpy)$_2$-PF$_6$ | 1,3-di(methylpyrrolidinium)propane di-hexafluorophosphate |
| C$_9$(mpy)$_2$-Br | 1,9-di(methylpyrrolidinium)nonane di-bromide |
| C$_9$(mpy)$_2$-NTf$_2$ | 1,9-di(methylpyrrolidinium)nonane di-bis[(trifluoromethyl)sulfonyl]imidate |
| C$_9$(mpy)$_2$-PF$_6$ | 1,9-di(methylpyrrolidinium)nonane di-hexafluorophosphate |
| C$_9$(bpy)$_2$-Br | 1,9-di(butylpyrrolidinium)nonane di-bromide |
| C$_9$(bpy)$_2$-NTf$_2$ | 1,9-di(butylpyrrolidinium)nonane di-bis[(trifluoromethyl)sulfonyl]imida |
| C$_9$(bpy)$_2$-PF$_6$ | 1,9-di(butylpyrrolidinium)nonane di-hexafluorophosphate |

EXAMPLES

Example 1

Compound #2

Synthesis of 2 involved adding 15.0 mL (0.148 mol) of 1,3-dibromopropane dropwise to 23.5 mL (0.295 mol) of 1-methylimidazole in a round bottom flask under constant stirring at room temperature. The reaction was complete within 2 hours. The bromide salt was dissolved in 100 mL water and extracted with three 25 mL aliquots of ethyl acetate. Water was removed under vacuum heating and the remaining salt was dried under a $P_2O_5$ vacuum. Synthesis of the $NTf_2^-$ salt consisted of dissolving 10 grams (0.03 mol) of the bromide salt in 100-150 mL water. Two molar equivalents (0.06 mol, 3.92 grams) of N-lithiotrifluoromethylsulfonimide were dissolved in 50 mL of water in a separate beaker and added directly to the bromide salt. The solution was allowed to stir for 12 hours. The top water layer was removed to leave the ionic liquid. Three additional 30 mL aliquots of water were added and extracted with the ionic liquid until the ionic liquid passed the silver nitrate test. The ionic liquid was then dried using rotary evaporation and then further dried under a $P_2O_5$ vacuum.

Example 2

Compound #7

Synthesis of 7 involved adding 15.0 mL (0.098 mol) of 1,6-dibromohexane dropwise to 15.6 mL (0.196 mol) of 1-methylimidazole in a round bottom flask under constant stirring at room temperature. The reaction was complete within 2 hours. The bromide salt was dissolved in 100 mL water and extracted with three 25 mL aliquots of ethyl acetate. Water was removed under vacuum heating and the remaining salt was dried under a $P_2O_5$ vacuum. Anions were exchanged by dissolving 10 grams (0.024 mol) of the bromide salt in ~150 mL acetone. Two molar equivalents of sodium tetrafluoroborate (0.049 mol, 5.38 grams) were then directly added to the acetone mixture. After allowing 24 hours for complete mixing, sodium bromide was filtered off to leave the pure ionic liquid. The sample was then subjected to silver nitrate to ensure no silver bromide precipitate was present. Acetone was removed under vacuum and the remaining ionic liquid dried under a $P_2O_5$ vacuum.

Example 3

Compound #17

Synthesis of 17 involved adding 15.0 mL (0.074 mol) of 1,9-dibromononae dropwise to 19.4 mL (0.148 mol) of 1-butylimidazole in a round bottom flask under constant stirring at room temperature. The reaction was complete after 5 hours. The resulting viscous liquid was dissolved in 100 mL water and extracted with three 35 mL aliquots of ethyl acetate. Water was removed under vacuum heating and the remaining salt was dried under a $P_2O_5$ vacuum.

Example 4

Compound #25

Synthesis of 25 involved dissolving 13.1 mL (0.148 mol) of 1,2-dimethylimidazole in 125 mL 2-propanol and adding 15.0 mL (0.074 mol) of 1,9-dibromononane dropwise in a round bottom flask equipped with a condenser and refluxing at 95° C. for 24 hours. After removal of 2-propanol under vacuum, the bromide salt was dissolved in 100 mL water and extracted with three 35 mL aliquots of ethyl acetate. Water was removed under vacuum heating and the remaining salt was dried under a $P_2O_5$ vacuum. Synthesis of the $NTf_2^-$ salt consisted of dissolving 10 grams (0.02 mol) of the bromide salt in 100-150 mL water. Two molar equivalents (0.04 mol, 11.48 grams) of N-lithiotrifluoromethylsulfonimide were dissolved in 50 mL of water in a separate beaker and added directly to the bromide salt. The solution was allowed to stir for 12 hours. The top water layer was removed to leave the ionic liquid. Three additional 30 mL aliquots of water were added and extracted with the ionic liquid until the ionic liquid passed the silver nitrate test. The ionic liquid was then dried using rotary evaporation and then further dried under a $P_2O_5$ vacuum.

Example 5

Compound #29

Synthesis of 29 involved dissolving 25.0 g (0.158 mol) of 1-benzylimidazole in 100 mL 2-propanol and adding 25.9 grams (0.079 mol) of 1,12-dibromododecane in a round bottom flask equipped with a condenser and refluxing at 95° C. for 24 hours. Due to the hydrophobicity of the salt, it was found to be quite insoluble in water. Therefore, it was washed with ethyl acetate (~75 mL) and then dried under $P_2O_5$. Because the bromide salt as not soluble in water, 10.0 grams (0.016 mol) was dissolved in methanol with stirring. To another beaker was added 8.9 grams (0.031 mol) of N-lithiotrifluoromethylsulfonimide with approximately 50 mL of water. The two contents were mixed the mixture allowed to stir for nearly 5 hours. The methanol-water solution was then removed and the liquid washed with water and then further dried under vacuum and under $P_2O_5$.

Example 6

Compound #31

Synthesis of 31 involved dissolving 13.0 mL (0.128 mol) of 1,3-dibromopropane in 100 mL 2-propanol and adding 26.6 mL (0.256 mol) of 1-methylpyrrolidine in a round bottom flask equipped with a condenser and refluxing at 95° C. for 24 hours. After removal of 2-propanol under vacuum, the bromide salt was dissolved in 100 mL water and extracted with three 35 mL aliquots of ethyl acetate. Water was removed under vacuum heating and the remaining salt was dried under a $P_2O_5$ vacuum.

Example 7

Compound #35

Synthesis of 35 involved dissolving 12.0 mL (0.059 mol) of 1,9-dibromononane in 100 mL 2-propanol and adding 12.3 mL (0.118 mol) of 1-methylpyrrolidine in a round bottom flask equipped with a condenser and refluxing at 95° C. for 24 hours. After removal of 2-propanol under vacuum, the bromide salt was dissolved in 100 mL water and extracted with three 35 mL aliquots of ethyl acetate. Water was removed under vacuum heating and the remaining salt was dried under a $P_2O_5$ vacuum. Synthesis of the $NTf_2^-$ salt consisted of dissolving 10 grams (0.02 mol) of the bromide salt in 100-150 mL water. Two molar equivalents (0.04 mol, 11.48 grams) of N-lithiotrifluoromethylsulfonimide were dissolved in 50 mL of water in a separate beaker and added directly to the bromide salt. The solution was allowed to stir for 12 hours. The top water layer was removed to leave the ionic liquid. Three additional 30 mL aliquots of water were added and extracted with the ionic liquid until the ionic liquid passed the silver nitrate test. The ionic liquid was then dried using rotary evaporation and then further dried under a $P_2O_5$ vacuum.

Example 8

Compound #38

Synthesis of 38 involved dissolving 13.0 mL (0.064 mol) of 1,9-dibromononane in 100 mL 2-propanol and adding 20.0 mL (0.128 mol) of 1-butylpyrrolidine in a round bottom flask equipped with a condenser and refluxing at 95° C. for 24 hours. After removal of 2-propanol under vacuum, the bromide salt was dissolved in 100 mL water and extracted with three 35 mL aliquots of ethyl acetate. Water was removed under vacuum heating and the remaining salt was dried under a $P_2O_5$ vacuum. Synthesis of the $NTf_2^-$ salt consisted of dissolving 10 grams (0.019 mol) of the bromide salt in 100-150 mL water. Two molar equivalents (0.037 mol, 10.62 grams) of N-lithiotrifluoromethylsulfonimide were dissolved in 50 mL of water in a separate beaker and added directly to the bromide salt. The solution was allowed to stir for 12 hours. The top water layer was removed to leave the ionic liquid. Three additional 30 mL aliquots of water were added and extracted with the ionic liquid until the ionic liquid passed the silver nitrate test. The ionic liquid was then dried using rotary evaporation and then further dried under a $P_2O_5$ vacuum.

REFERENCES

1. Welton, T. *Chem. Rev.* 1999, 99, 2071-2083.
2. Cadena, C.; Anthony, J. L.; Shah, J. K.; Morrow, T. I.; Brennecke, J. F.; Maginn, E. J. *J. Am. Chem. Soc.* 2004, 126, 5300-5308.
3. Visser, A. E.; Swatloski, R. P.; Reichert, W. M.; Mayton, R.; Sheff, S.; Wierzbicki, A.; Davis, J. H.; Rogers, R. D. *Environ. Sci. Technol.* 2002, 36, 2523-2529.
4. Anderson, J. L.; Armstrong, D. W., *Anal. Chem.* 2003, 75, 4851-4858.
5. Anderson, J. L.; Pino, V.; Hagberg, E. C.; Sheares, V. V.; Armstrong, D. W., *Chem. Commun.* 2003, 2444-2445.
6. Fletcher, K. A.; Pandey, S. *Langmuir* 2004, 20, 33-36.
7. Zhou, Y.; Antonietti, M., *J. Am. Chem. Soc.* 2003, 125, 14960-14961.
8. Luo, H.; Dai, S.; Bonnesen, P. V.; Buchanan, A. C.; Holbrey, J. D.; Bridges, N. J.; Rogers, R. D. *Anal. Chem.* In press
9. Wu, J.; Zhang, J.; Zhang, H.; He, J.; Ren, Q.; Guo, M., *Biomacromolecules* 2004, 5, 266-268.
10. Vijayaraghavan, R.; MacFarlane, D. R., *Chem. Commun.* 2004, 700-701.
11. Boxall, D. L.; Osteryoung, R. A., *J. Electrochem. Soc.* 2004, 151, E41-E45
12. Earle, M. J.; Katdare, S. P.; Seddon, K. R., *Org. Lett.* 2004, 6, 707-710.
13. Carter, E. B.; Culver, S. L.; Fox, P. A.; Goode, R. D.; Ntai, I.; Tickell, M. D.; Traylor, R. K.; Hoffman, N. W.; Davis, J. H. *Chem. Commun.* 2004, 630-631.
14. Wasserscheid, P.; Hilgers, C.; Keim, W., *Journal of Molecular Catalysis A* 2004, 214, 83-90.
15. Gao, H.; Jiang, T.; Han, B.; Wang, Y.; Du, J.; Liu, Z.; Zhang, J., *Polymer* 2004, 45, 3017-3019
16. Kaar, J. L.; Jesionowski, A. M.; Berberich, J. A.; Moulton, R.; Russell, A. J., *J. Am. Chem. Soc.* 2003, 125, 4125-4131.
17. Zhao, H.; Malhotra, S. V. *Biotechnology Letters* 2002, 24, 1257-1260.
18. Lee, J. K.; Kim, M-J., *J. Org. Chem.* 2002, 67, 6845-6847.
19. Wilkes, J. S., *Journal of Molecular Catalysis A: Chemical* 2004, 214, 11-17.
20. Bonhote, P.; Dias, A.-P.; Papageorgiou, N.; Kalyanasundaram, K.; Gratzel, M. *Inorg Chem.* 1996, 35, 1168.
21. Wei, G-T.; Yang, Z.; Lee, C-Y.; Yang, H-Y.; Wang, C. R., *J. Am. Chem. Soc.* 2004, 126, 5036-5037.
22. Itoh, H.; Naka, K.; Chujo, Y., *J. Am. Chem. Soc.* 2004, 126, 3026-3027.
23. Katritzky, A. R.; Jain, R.; Lomaka, A.; Petrukhin, R.; Karelson, M.; Visser, A. E.; Rogers, R. D, *J. Chem. Inf. Comput. Sci.* 2002, 42, 225-231.
24. Eike, D.; Brennecke, J. F.; Maginn, E. J., *Green Chem.* 2003, 5, 323.
25. Forsyth, S. A.; Pringle, J. M.; MacFarlane, D. R., *Aust. J. Chem.* 2004, 57, 113-119.
26. Dzyuba, S. V.; Bartsch, R. A., *Chem. Phys. Phys. Chem.* 2002, 3, 161-166.
27. Seddon, K. R.; Stark, A.; Torres, M-J., ACS Symposium Series 2002, 819 (Clean Solvents: Alternative Media for Chemical Reactions and Processing), 34-49.
28. Carda-Broch, S.; Berthod, A.; Armstrong, D. W., *Anal. Bioanal. Chem.* 2003, 375, 191.
29. Baranyai, K. J.; Deacon, G. B.; MacFarlane, D. R.; Pringle, J. M.; Scott, J. L., *Aust. J. Chem.* 2004, 57, 145-147.
30. Van Valkenburg, M. E.; Vaughn, R. L.; Williams, M.; Wilkes, J. S. Proceedings—Electrochemical Society 2002, 2002-19 (Molten Salts XIII), 112-123.
31. Anderson, J. L.; Ding, J.; Welton, T.; Armstrong, D. W., *J. Am. Chem. Soc.* 2002, 124, 14247-14254.
32. Blessing, R. H., *Acta Cryst.* 1995, A51, 33-38.
33. All software and sources of the scattering factors are contained in the SHELXTL (version 5.1) program library (G. Sheldrick, Bruker Analytical X-Ray Systems, Madison, Wis.).
34. Law, G.; Watson, P. R., *Langmuir* 2001, 17, 6138-6141.
35. Ngo, H. L.; LeCompte, K.; Hargens, L.; McEwen, A. B., *Thermochimica Acta* 2000, 357-358, 97-102
36. Hu, X.; Tang, Y.; Gantzel, P.; Meyer, K., *Organometallics* 2003, 22, 612-614.
37. Bryce, M. R., *Chem. Soc. Rev.* 1991, 20, 355-390.
38. Holbrey, J. D.; Reichert, W. M.; Nieuwenhuyzen, M.; Johnston, S.; Seddon, K. R.; Rogers, R. D., *Chem. Commun.* 2003, 1636-1637.
39. Dearden, J. C., *Sci. Total Environ.* 1991, 59, 109-110.
40. Bondi, A.-J., *J. Phys. Chem.* 1964, 68, 441-453.
41. Anderson, J. L.; Ding, R.; Ellern, A,; Armstrong, D. W. *J. Am. Chem. Sac.* 2005, 127, 593-604.
42. Terazima, M.; Nogami, Y.; Tominaga, T. *Chemical Physical Letters* 2000,332, 503-507.
43. Van Hook, J. P.; Tobolsky, A. V. *J. Am. Chem. Soc.* 1958,80,779-782.
44. Anderson, J. L.; Ding, J.; Welton, T.; Armstrong, D. W. *J. Am. Chem. Soc.* 2002, 124, 14247-14254.
45. Abraham, M. H. *Chem. Soc. Rev.* 1993, 22, 73,
46. Abraham, M. H.; Whiting, G. S.; Doherty, R. M.; Shuely, W. J. *J Chromatogr.* 1991,587,229-236.
47. Bouche, J.; Verzele, M. *J Gas Chromatogr.* 1968, 6, 501.

48. Muldoon, M. J.; Gordon, C. M. *J Polym. Sci. Part A. Polym. Chem.* 2004, 42, 3865-3869.

49. Marcilla, R.; Blazquez, J. A.; Rodriguez, J.; Pomposo, J. A.; Mecerreyes, D. *J Polym. Sci. Part A: Polym. Chem.* 2004,42,208-212.

50. Armstrong, D. W.; He, L.; Liu, L.-S. *Anal. Chem.* 1999, 71,3873-3876

51. Anderson, J. L.; Armstrong, D. W. *Anal. Chem.* 2003, 75,4851-4858.

52. Lord & Pawliszym, *J. Chromatogr. A* 885 (2000) 153-193.

53. Visser et al. "Task-Specific Ionic Liquids Incorporation Novel Cations for the Coordination and Extraction of Hg2+ and Cd2+: Synthesis, Characterization, and Extraction Studies," *Environ. Sci. Technol.* (2002) 36, 2523-29.

54. Liu et al. "Disposable ionic liquid coating for headspace solid-phase microextraction of benzene, toluene, ethyl benzene, and xylenes in plants followed by gas chromatography—flame ionization detection," *J. Chromatogr. A* (2005), 1066 (1-2), 27-32.

55. Vas, G.; Vekey, K., J. Mass Spectrometery (2004) 39, 233-254.

The invention claimed is:

1. A method of separating one chemical from a mixture of chemicals comprising the steps of: providing a mixture of at least one first and at least one second chemical, exposing said mixture to at least one
   capillary column and at least one diionic liquid salt adsorbed, absorbed or immobilized thereon, wherein the diionic liquid salt comprises at least one di-cation of the formula:

A-B-A' and at least one counter anion; wherein:
   A and A' are mono-cationic groups independently selected from the group consisting of optionally substituted imidazolium, and pyrrolidinium; wherein when A and A' are both substituted imidazolium, at least one of A and A' is substituted with a group that facilitates cross-linking and/or immobilization; and
   bridging group, B, is an optionally substituted $C_2$-$C_{40}$ hydrocarbon backbone, wherein the hydrocarbon backbone optionally contains, in addition to carbon and hydrogen atoms, at least one heteroatom selected from the group consisting of nitrogen, oxygen, sulfur and/or silicon atom;
   and retaining at least a portion of said first chemical on said solid support capillary column for some period of time.

2. The method of claim 1, further comprising at least one monoionic liquid mixed with said diionic liquid salt and wherein said mixture is immobilized on said solid support.

3. The method of claim 1, wherein said mixture is passed through said column such that elution of said first chemical is prevented or delayed.

4. The method of claim 1, wherein said mixture is carried in a gaseous mobile phase.

5. The method of claim 1, wherein said solid support is attached to a microsyringe having a hollow needle defining an inner space, said needle being disposed at an end of a barrel and a plunger disposed within said barrel, said solid support being attached to said microsyringe such that it may be retracted into said inner space of said needle when said plunger is retracted from said barrel and exposed from within said needle when said plunger is inserted into said barrel, exposing said solid support from within said needle into said mixture, and retracting said solid support from said mixture, wherein it includes at lease some amount of said first chemical.

6. The method of claim 1, wherein said capillary column is useful in gas chromatography.

7. The method of claim 1, wherein said capillary column further comprises a syringe having a hollow needle defining an inner space, said needle being disposed at an end of a barrel and a plunger disposed within said barrel, a solid support being attached to said syringe such that it may be retracted into said inner space of said needle when said plunger is retracted from said barrel and exposed from within said needle when said plunger is inserted into said barrel.

8. The method of claim 1, wherein said diionic liquid salt is immobilized on said capillary column and wherein said diionic liquid salt includes at least one unsaturated group which can facilitate cross-linking or immobilization.

9. The method of claim 7, wherein said syringe is a microsyringe.

10. The method of claim 1, wherein the diionic liquid salt has a solid/liquid transition temperature of about 100° C. or less.

11. The method of claim 1, wherein the diionic liquid salt has a solid/liquid transition temperature of about 25° C. or less.

12. The method of claim 1, wherein the bridging group, B, has a length about equivalent to a $C_3$-$C_{30}$ carbon chain.

13. The method of claim 1, wherein the bridging group, B, contains at least one unsaturated group which can facilitate cross-linking or immobilization.

14. The method of claim 1, wherein the bridging group, B, contains at least one heteroatom selected from the group consisting of nitrogen, oxygen, sulfur, and/or silicon.

15. The method of claim 1, wherein A and A' are both substituted imidazolium and, at least one of A and A' is substituted with a group that facilitates cross-linking and/or immobilization.

16. The method of claim 1, wherein the at least one counter anion is a diionic counter anion.

17. The method of claim 16, wherein the diionic counter anion is selected from the group consisting of carboxylate, sulfate and sulfonate.

18. The method of claim 1, wherein the diionic liquid salt comprises two mono-ionic counter anions.

19. The method of claim 18, wherein the two mono-ionic counter anions are independently selected from the group consisting of Br⁻, mono-sulfonate, mono-sulphate, $NTf_2^-$, $BF_4^-$, triflate and $PF_6^-$.

20. The method of claim 1, wherein A and A' are pyrrolidinium.

21. The method of claim 1, wherein the diionic liquid salt comprises,

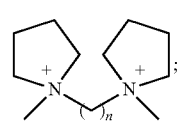

wherein n is 3 to 30.

22. The method of claim 1, wherein the diionic liquid salt comprises,

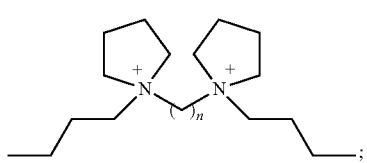

wherein n is 3 to 30.

23. The method of claim 1, wherein the diionic liquid salt is selected from the group consisting of

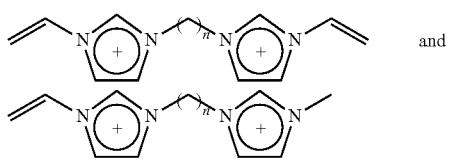

and wherein n is 3 to 30.

24. The method of claim 23, wherein the at least one di-cation is selected from the group consisting of:

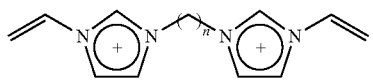

wherein n is 6, 9, 10, 11, or 12; and

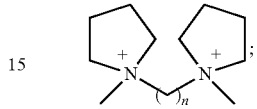

wherein n is 6.

25. The method of claim 21, wherein the at least one di-cation is of the formula:

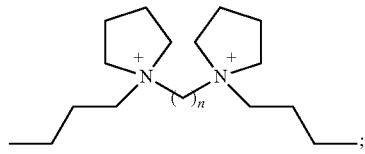

wherein n is 3 or 9.

26. The method of claim 22, wherein the at least one di-cation is of the formula:

wherein n is 9.

* * * * *

UNITED STATES PATENT AND TRADEMARK OFFICE
CERTIFICATE OF CORRECTION

| | | |
|---|---|---|
| PATENT NO. | : 8,182,581 B2 | Page 1 of 1 |
| APPLICATION NO. | : 11/187389 | |
| DATED | : May 22, 2012 | |
| INVENTOR(S) | : Armstrong et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1200 days.

Signed and Sealed this
Seventeenth Day of March, 2020

Andrei Iancu
*Director of the United States Patent and Trademark Office*